(12) United States Patent
Hedrick et al.

(10) Patent No.: US 8,598,320 B2
(45) Date of Patent: Dec. 3, 2013

(54) ANTI-PCSK9 AND METHODS FOR TREATING LIPID AND CHOLESTEROL DISORDERS

(75) Inventors: Joseph A. Hedrick, South River, NJ (US); Frederick James Monsma, Jr., Summit, NJ (US); Tatyana Churakova, Sunnyvale, CA (US); Diane Hollenbaugh, Mountain View, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 477 days.

(21) Appl. No.: 12/739,761

(22) PCT Filed: Oct. 27, 2008

(86) PCT No.: PCT/US2008/081311
§ 371 (c)(1),
(2), (4) Date: Oct. 6, 2010

(87) PCT Pub. No.: WO2009/055783
PCT Pub. Date: Apr. 30, 2009

(65) Prior Publication Data
US 2011/0033465 A1 Feb. 10, 2011

Related U.S. Application Data

(60) Provisional application No. 60/982,922, filed on Oct. 26, 2007.

(51) Int. Cl.
*C12P 21/08* (2006.01)
(52) U.S. Cl.
USPC ........................................ 530/387.3
(58) Field of Classification Search
None
See application file for complete search history.

(56) References Cited

U.S. PATENT DOCUMENTS

2001/0025026 A1* 9/2001 Heartlein et al. ............ 514/12

FOREIGN PATENT DOCUMENTS

| WO | WO2008/057457 | 5/2008 |
| WO | WO2008/057458 | 5/2008 |
| WO | WO2008/057459 | 5/2008 |
| WO | WO2008/125623 | 10/2008 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
MacCallum et al. (J. Mol. Biol. Oct. 11, 1996; 262 (5): 732-745).*
Holm et al. (Mol. Immunol. Feb. 2007; 44 (6): 1075-1084).*
Lagace, Thomas, et al.; "Secreted PCSK9 decreases the number of LDL receptors in hepatocytes and in livers of parabiotic mice"; Journal of Clinical Investigation, American Society for Clinical Investigation; 116(11):2995-3005 (2006).
Benjannet, Suzanne, et al.; "The proprotein convertase (PC) PCSK9 is inactivated by furin and/or PC5/6A: functional consequences of natural mutations and post-translational modifications"; Journal of Biological Chemistry, American Society of Biochemical Biologists; 281(40:30561-30572 (2006).
Cayman Chemical Company; "Product Information PCSK9 (murine) Polyclonal Antibody Catalog No. 10008811"; internet citation (www.caymaneurope.com); pp. 1-2 (Dec. 12, 2007).
Cayman Chemical Company; "Product Information PCSK9 Polyclonal Antibody Catalog No. 10007185"; internet citation (www.caymaneurope.com); pp. 1-2 (Dec. 10, 2007).
Cayman Chemical Company; "Material Safety Data Sheet PCSK9 (murine) Polyclonal Antibody"; internet citation (www.caymaneurope.com); pp. 1-4 (Sep. 5, 2007).
Cayman Chemical Company, "Material Safety Data Sheet PCSK9 (human) Polyclonal Antibody"; internet citation (www.caymaneurope.com); pp. 1-3 (Jul. 26, 2007).
Horton, et al.; "Molecular biology of PCSK9: its role in LDL metabolism"; Trends in Biochemical Sciences; 32(2):71-77 (2007).
International Search Report for International Application No. PCT/US2008/081311 dated Jul. 31, 2009.

* cited by examiner

*Primary Examiner* — Brad Duffy
(74) *Attorney, Agent, or Firm* — Sheela Mohan-Peterson

(57) ABSTRACT

The present invention provides compositions and methods for treating disorders of cholesterol and lipid metabolism by administration of an anti-PCSK9 antibody or a peptide inhibitor of PCSK9.

9 Claims, 4 Drawing Sheets

Residue numbering according to Kabat
HEAVY CHAINS

```
                                                              -----CDR-H1-----
11B5   (SEQ ID NO: 10)   E V Q L Q Q S G A E L V K P G A S V T L S C T A S G F N I K D T Y M H
75B9   (SEQ ID NO: 18)   E V Q L Q Q S G A D L V K P G A S V K L S C T A S G F N I K D T Y I H
77D10  (SEQ ID NO: 26)   E V Q L Q Q S G A E L V R S G A S V R L S C T T S G F N I K D T Y Y H
29C10  (SEQ ID NO: 34)   E V L L Q Q S V A E L V R P G A S V R L S C T A S G F N I K D T Y I H
22D11  (SEQ ID NO: 42)   E V Q L V D S G G G L V Q P G G S L K L S C A A S G F T F S N H D M A
1F11   (SEQ ID NO: 50)   E V Q L Q Q S G P E L V K P G A S V K I S C K V S G Y T F T D Y Y M N
1G11   (SEQ ID NO: 50)   E V Q L Q Q S G P E L V K P G A S V K I S C K V S G Y T F T D Y Y M N
                         1                   10                  20      26        30        35

-----CDR-H2-----
11B5   (SEQ ID NO: 10)   W V N Q R P E Q G L V W I G R I D P A N G H T E Y D P K F Q D
75B9   (SEQ ID NO: 18)   W V K Q R P E Q G L E W I G R I D P A N G H T E Y D P K F Q G
77D10  (SEQ ID NO: 26)   W V K Q R P E Q G L E W I G W I D P E N G D T E Y A P K F Q G
29C10  (SEQ ID NO: 34)   W V R Q A P G Q G L E W I G W I D P A N G Y T K Y A P N F Q G
22D11  (SEQ ID NO: 42)   W V R Q A P T K G L E W V A S I T P S G G T T Y Y R D S V E G
1F11   (SEQ ID NO: 50)   W V K Q S H G K S L E W I G D I N P N N G A I Y N Q K F K G
1G11   (SEQ ID NO: 50)   W V K Q S H G K S L E W I G D I N P N N G A I Y N Q K F K G
                                         40                  50   a           60        65
```

FIG. 1A

```
                              ------CDR-H3------
11B5  (SEQ ID NO: 10)  K A T I T T D T S S N T A Y L H L S S L T S G D T A V Y Y C A R
75B9  (SEQ ID NO: 18)  R A T L T T D T S S N T A Y L Q L F S L T S E D S A V Y F C A R
77D10 (SEQ ID NO: 26)  K A T M T A D T S S N T A Y L H L S S L T S A D T A V Y Y C N A
29C10 (SEQ ID NO: 34)  K A T L T T D T S S N T A Y L H L S S L T S E D S A I Y Y C A R
22D11 (SEQ ID NO: 42)  R F T V S R D N V K S S L H L Q M D S L T S E D T A T Y Y C A R
1F11  (SEQ ID NO: 50)  K A T L T V D K S S S I A Y M E L R S L T S E D S A V Y Y C T S
1G11  (SEQ ID NO: 50)  K A T L T V D K S S S I A Y M E L R S L T S E D S A V Y Y C T S
                                 70              80                    90

------CDR-H3------
11B5  (SEQ ID NO: 10)  S Y F G S I           F A Y W G Q G T L V T V S A
75B9  (SEQ ID NO: 18)  S Y Y G S I           F A Y W G Q G T L V T V S A
77D10 (SEQ ID NO: 26)  Y Y R Y D D G T W     F P Y W G Q G T S V T V S S
29C10 (SEQ ID NO: 34)  G Y Y R Y Y S         L D Y W G Q G T S V T V S S
22D11 (SEQ ID NO: 42)  Q N Y Y D G SYYYGLYY  F D Y W G Q G V M V T V S S
1F11  (SEQ ID NO: 50)  G I I T E I A         E D F W G Q G T T L T V S S
1G11  (SEQ ID NO: 50)  G I I T E I A         E D F W G Q G T T L T V S S
                       95               a b c        102             110
```

FIG. 1B

LIGHT CHAINS

```
                              -----------------L1--------
11B5   (SEQ ID NO: 14)  Q I V L T Q S P A I M S A S P G E K V T I S C S A S S S
75B9   (SEQ ID NO: 22)  Q I H V L T Q S P A I M S A S P G E K V T I S C S A S S S
77D10  (SEQ ID NO: 30)  D I Q L T Q S P A S L S A S V G E T V T I T C R A S G N I
29C10  (SEQ ID NO: 38)  D I Q M T Q S P T T L S A S L G D R V T I S C R A S Q D I
22D11  (SEQ ID NO: 46)  D V L M T Q T P V S L P V S L G Q V S H I S C R S S Q SLVYS D G
1F11   (SEQ ID NO: 54)  D I V M T Q S Q K F M S T S V G D R V S V T C K A S Q N V
1G11   (SEQ ID NO: 54)  D I V M T Q S Q K F M S T S V G D R V S V T C K A S Q N V
                        1                             10                    20              24

-L1------                                       -----L2-------
11B5   (SEQ ID NO: 14)  V S Y L Y W Y Q Q K P G S S S P K P W I F R S S H R A S G V P
75B9   (SEQ ID NO: 22)  V S Y L F W Y Q Q K P G S S S P K P W I F R T S Y L A S G V P
77D10  (SEQ ID NO: 30)  H S Y L A W Y Q Q K P G K Q K S P Q F L L L I Y Y D N A K T L P D G V P
29C10  (SEQ ID NO: 38)  S N Y L N W Y Q Q K P D G T V K L L I Y Y S S R L H S G V P
22D11  (SEQ ID NO: 46)  N T Y L H W Y L Q K P G Q S P Q L L I Y R V S N R F S G V P
1F11   (SEQ ID NO: 54)  G T N V V W Y Q Q K P G Q S P K P K A L I H S A S Y R Y S G V P
1G11   (SEQ ID NO: 54)  G T N V V W Y Q Q K P G Q S P K P K A L I H S A S Y R Y S G V P
                        30          34                    40                    50              56
```

```
11B5   (SEQ ID NO: 14)  A R F S G S G S G T S Y S L T I S S M E A E D A A T Y Y C
75B9   (SEQ ID NO: 22)  A R F S G S G S G T S F S L T I S S M E A E D A A T Y Y C
77D10  (SEQ ID NO: 30)  S R F S V S G R G T Q Y S L K I N S L Q P E D F G T A T Y F C
29C10  (SEQ ID NO: 38)  S R F S G R G S G T D Y S L T I S T L E Q E D D I A T Y F C
22D11  (SEQ ID NO: 46)  D R F S G S G S G T D F T L T I S R V E P E D L G L Y Y C
1F11   (SEQ ID NO: 54)  D R F K G S G S G T D F T L T I T N V Q S E D L A G F F C
1G11   (SEQ ID NO: 54)  D R F K G S G S G T D F T L T I T N V Q S E D L A G F F C
                        60                            70                          80

|---------L3---------|
11B5   (SEQ ID NO: 14)  H Q Y Q S Y P P T F G G G T K L E I H K R A
75B9   (SEQ ID NO: 22)  H Q Y H T Y P P T F G G G T K L E I H K R A
77D10  (SEQ ID NO: 30)  Q H F W N T P W T F G G G T K L E I K K R A
29C10  (SEQ ID NO: 38)  Q Q G K T L P L T F G A G T K L E I K K R A
22D11  (SEQ ID NO: 46)  L Q S T H F P P T F G G G S G T K L E I K K R A
1F11   (SEQ ID NO: 54)  Q Q Y K T Y P Y T F G G G T Q L E I K R R A
1G11   (SEQ ID NO: 54)  Q Q Y K T Y P Y T F G G G T Q L E I K R R A
                        89                  97        100
```

ANTI-PCSK9 AND METHODS FOR TREATING LIPID AND CHOLESTEROL DISORDERS

This application claims the benefit of U.S. patent application No. 60/982,922, filed Oct. 26, 2007, which is herein incorporated by reference in its entirety.

FIELD OF THE INVENTION

The field of the present invention relates to methods and compositions for treating disorders of cholesterol homeostasis by administering an anti-PCSK9 antibody or antigen-binding fragment thereof.

BACKGROUND OF THE INVENTION

Atherosclerotic coronary heart disease (CHD) represents the major cause for death and cardiovascular morbidity in the western world. Risk factors for atherosclerotic coronary heart disease include hypertension, diabetes mellitus, family history, male gender, cigarette smoke, high serum cholesterol, high low density lipoprotein (LDL) cholesterol levels and low high density lipoprotein (HDL) cholesterol levels. In general, a total cholesterol level in excess of about 225-250 mg/dl is associated with significant elevation of risk of CHD.

A variety of clinical studies have demonstrated that elevated levels of total cholesterol or LDL cholesterol promote human atherosclerosis. Epidemiologic investigations have established that cardiovascular morbidity and mortality vary directly with the level of total cholesterol and LDL cholesterol.

One method for lowering LDL cholesterol levels is by administration of HMG-CoA reductase inhibiting drugs. These drugs antagonize HMG-CoA reductase and cholesterol synthesis in the liver and increase the number of hepatic LDL receptors on the cell-surface to enhance uptake and catabolism of LDL, A drawback of such an approach is that these drugs commonly suffer from a disadvantageous side-effect profile, including, for example, liver toxicity. An alternate approach is to modulate the LDL receptor pathway directly.

PCSK9 (proprotein convertase subtilisin/kexin type 9) serine protease family member that binds to and regulates LDL receptor expression on the surface of cells. Inhibition of the LDL receptor-PCSK9 interaction is an attractive approach to the treatment of cholesterol disorders. Inhibition of interactions between large proteins (i.e., protein-protein interactions or PPI) by the use of antibodies or small molecule inhibitors is, however, generally regarded as being particularly difficult and challenging. Large proteins such as PCSK9, with a molecular weight of about 74 KDa, and LDLR, with a molecular weight of about 160 KDa (glycosylated on cell surface; 115 KDa in immature form), are likely to exhibit extensive intermolecular contacts over a large area. The existence of extensive contacts makes it unlikely that a given antibody or small molecule inhibitor will successfully block their binding.

SUMMARY OF THE INVENTION

The present invention surprisingly has overcome the technical difficulties associated with the blocking of intermolecular interactions between large proteins and has demonstrated that blockage of the PCSK9-LDLR interaction with an antibody or peptide is possible. As discussed in detail herein, this, in turn, provides a novel method by which to treat cholesterol disorders.

The present invention provides, in part, a method for reducing total cholesterol level, low density lipoprotein cholesterol level, apolipoprotein B level, total cholesterol/high density lipoprotein ratio or low density lipoprotein/high density lipoprotein ratio, in a subject (e.g., a human), comprising administering, to said subject, a therapeutically effective amount of an antibody or antigen-binding fragment thereof (e.g., monoclonal antibody, polyclonal antibody or recombinant antibody) or EGF-A polypeptide that binds specifically to PCSK9 which antibody or fragment or polypeptide inhibits binding between PCSK9 and LDL receptor; optionally in association with a further chemotherapeutic agent (e.g., ezetimibe and/or simvastatin). In an embodiment of the invention, the antibody or fragment or EGF-A polypeptide binds specifically to a PCSK9 catalytic domain or to a domain of PCSK9 which interacts with an LDL receptor EGF-A domain.

The present invention further provides, in part, a method for treating or preventing hypercholesterolernia, hyperlipidemia, hypertriglyceridaemia, sitosterolemia, atherosclerosis, arteriosclerosis, coronary heart disease, vascular inflammation or xanthoma, in an subject, comprising administering, to said subject, a therapeutically effective amount of an antibody or antigen-binding fragment thereof (e.g., monoclonal antibody, polyclonal antibody or recombinant antibody) or EGF-A polypeptide that binds specifically to PCSK9, which antibody or fragment or polypeptide inhibits binding between PCSK9 and LDL receptor; optionally in association with a further therapeutic agent (e.g., ezetimibe and/or simvastatin). In an embodiment of the invention, the antibody or fragment or EGF-A polypeptide binds specifically to a PCSK9 catalytic domain or to a domain of PCSK9 which interacts with an LDL receptor EGF-A domain.

The present invention also provides, in part, a pharmaceutical composition comprising an antibody or antigen-binding fragment thereof (e.g., monoclonal antibody, polyclonal antibody or recombinant antibody) or EGF-A polypeptide which binds specifically to PCSK9, which antibody or fragment or polypeptide inhibits binding between PCSK9 and LDL receptor, and a pharmaceutically acceptable carrier; optionally in association with a further chemotherapeutic agent (e.g., ezetimibe and/or simvastatin).

The present invention also provides an isolated polypeptide comprising an amino acid sequence comprising about 90% or more amino acid sequence similarity to a fragment of the human LDL receptor which fragment consists of amino acids beginning at about amino acid position 314 and ending at about amino acid position 355 of said receptor wherein said polypeptide; wherein said polypeptide optionally comprises one or more properties selected from the group consisting of: (i) binds to PCSK9; (ii) competes with LDL receptor or an anti-PCSK9 antibody or antigen-binding fragment thereof for binding to PCSK9; (iii) reduces total cholesterol level when administered to an animal; (iv) reduces low density lipoprotein cholesterol level when administered to an animal; (v) reduces apolipoprotein B level when administered to an animal; (vi) reduces total cholesterol/high density lipoprotein ratio when administered to an animal; and (vii) reduces low density lipoprotein/high density lipoprotein ratio when administered to an animal; or a pharmaceutical composition thereof comprising a pharmaceutically acceptable carrier. In an embodiment of the invention, the polypeptide consists of the amino acid sequence of SEQ ID NO: 3; or a pharmaceutical composition thereof comprising a pharmaceutically acceptable carrier.

The present invention provides an isolated antibody or antigen-binding fragment thereof comprising one or more members selected from the group consisting of:
(i) CDR-H1, CDR-H2 and CDR-H3 of the variable region the 11B5 heavy chain immunoglobulin which comprises the amino acid sequence of SEQ ID NO: 10;
(ii) CDR-H1, CDR-H2 and CDR-H3 of the variable region the 75B9 heavy chain immunoglobulin which comprises the amino acid sequence of SEQ ID NO: 18;
(iii) CDR-H1, CDR-H2 and CDR-H3 of the variable region the 77D10 heavy chain immunoglobulin which comprises the amino acid sequence of SEQ ID NO: 26;
(iv) CDR-H1, CDR-H2 and CDR-H3 of the variable region the 29C10 heavy chain immunoglobulin which comprises the amino acid sequence of SEQ ID NO: 34;
(v) CDR-H1, CDR-H2 and CDR-H3 of the variable region the 22D11 heavy chain immunoglobulin which comprises the amino acid sequence of SEQ ID NO: 42;
(vi) CDR-H1, CDR-H2 and CDR-H3 of the variable region the 1F11/1G11 heavy chain immunoglobulin which comprises the amino acid sequence of SEQ ID NO: 50;
(vii) CDR-H1, CDR-H2 and CDR-H3 of the variable region the 11B5 light chain immunoglobulin which comprises the amino acid sequence of SEQ ID NO: 14;
(viii) CDR-H1, CDR-H2 and CDR-H3 of the variable region the 75B9 light chain immunoglobulin which comprises the amino acid sequence of SEQ ID NO: 22;
(ix) CDR-H1, CDR-H2 and CDR-H3 of the variable region the 77D10 light chain immunoglobulin which comprises the amino acid sequence of SEQ ID NO: 30;
(x) CDR-H1, CDR-H2 and CDR-H3 of the variable region the 29C10 light chain immunoglobulin which comprises the amino acid sequence of SEQ ID NO: 38;
(xi) CDR-H1, CDR-H2 and CDR-H3 of the variable region the 22D11 light chain immunoglobulin which comprises the amino acid sequence of SEQ ID NO: 46; and
(xii) CDR-H1, CDR-H2 and CDR-H3 of the variable region the 1F11/1G11 light chain immunoglobulin which comprises the amino acid sequence of SEQ ID NO: 54. The present invention also provides an isolated antibody or antigen-binding fragment thereof comprising one or more members selected from the group consisting of:
(i) HCDR1 comprising the amino acid sequence G F N I K D T Y M H (SEQ ID NO: 11), HCDR2 comprising the amino acid Sequence R I D P A N G H T E Y D P K F Q D (SEQ ID NO: 12) and HCDR3 comprising the amino acid sequence S Y F G S I F A Y (SEQ ID NO: 13); (ii) HCDR1 comprising the amino acid sequence G F N I K D T Y I H (SEQ ID NO: 19), HCDR2 comprising the amino acid sequence R I D P A N G H T E Y D P K F Q G (SEQ ID NO: 20) and HCDR3 comprising the amino acid sequence S Y Y G S I F A Y (SEQ ID NO: 21); (iii) HCDR1 comprising the amino acid sequence G F N I K D Y Y I H (SEQ ID NO: 27), HCDR2 comprising the amino acid sequence W I D P E N G D T E Y A P K P Q G (SEC) ID NO: 28) and HCDR3 comprising the amino acid sequence Y Y R Y D D G T W F P Y (SEQ ID NO: 29);
(iv) HCDR1 comprising the amino acid sequence G F N I K D T Y I H (SEQ ID NO: 35), HCDR2 comprising the amino acid sequence W I D P A N G Y T K Y A P N F Q G (SEQ ID NO: 36) and HCDR3 comprising the amino acid sequence G Y Y R Y Y S L D Y (SEQ ID NO: 37); (v) HCDR1 comprising the amino acid sequence G F T F S N H D M A (SEQ ID NO: 43), HCDR2 comprising the amino acid sequence S I T P S G G T T Y Y R D S V E G (SEQ ID NO: 44) and HCDR3 comprising the amino acid sequence Q N Y Y D G S Y Y Y G L Y Y F D Y (SEQ ID NO: 45); (vi) HCDR1 comprising the amino acid sequence G Y T F T D Y Y M N (SEQ ID NO: 51), HCDR2 comprising the amino acid sequence D I N P N N G G A I Y N Q K F K G (SEQ ID NO: 52) and HCDR3 comprising the amino acid sequence G I I T E I A E D F (SEQ ID NO: 53); (vii) LCDR1 comprising the amino acid sequence S A S S S V S Y L Y (SEC) ID NO: 15), LCDR2 comprising the amino acid sequence R S S H R A S (SEQ ID NO: 16) and LCDR3 comprising the amino acid sequence H Q Y Q S Y P P T (SEQ ID NO: 17); (viii) LCDR1 comprising the amino acid sequence S A S S S V S Y L F (SEQ ID NO: 23), LCDR2 comprising the amino acid sequence R T S Y L A S (SEQ ID NO: 24) and LCDR3 comprising the amino acid sequence H Q Y H T P P T (SEQ ID NO: 25); (ix) LCDR1 comprising the amino acid sequence R A S G N I H S Y L A (SEQ ID NO: 31), LCDR2 comprising the amino acid sequence N A K T L P D (SEQ ID NO: 32) and LCDR3 comprising the amino acid sequence Q H F W N T P W T (SEQ ID NO: 33);
(x) LCDR1 comprising the amino acid sequence R A S Q D I S N Y L N (SEQ ID NO: 39), LCDR2 comprising the amino acid sequence Y S S R L H S (SEQ ID NO: 40) and LCDR3 comprising the amino acid sequence Q Q G K T L P L T (SEC) ID NO: 41);
(xi) LCDR1 comprising the amino acid sequence R S S Q S L V Y S D G N T Y L H (SEQ ID NO: 47), LCDR2 comprising the amino acid sequence R V S N R F S (SEQ ID NO: 48) and LCDR3 comprising the amino acid sequence L Q S T H F P P T (SEQ ID NO: 49); and (xii) LCDR1 comprising the amino acid sequence K A S Q N V G T N V V (SEQ ID NO: 55), LCDR2 comprising the amino acid sequence S A S Y R Y S (SEC) ID NO: 56) and LCDR3 comprising the amino acid sequence Q Q Y K T Y P V T (SEQ ID NO: 57).

Furthermore, the present invention provides an isolated antibody or antigen-binding fragment thereof of claim xxx comprising one or more members selected from the group consisting of:

```
(a) an immunoglobulin heavy chain comprising
the amino acid sequence:
                                  (SEQ ID NO: 10)
E V Q L Q Q S G A E L V K P G A S V T L S C T A
S G F N I K D T Y M H W V N Q R P E Q G L V W I
G R I D P A N G H T E Y D P K F Q D K A T I T T
D T S S N T A Y L H L S S L T S G D T A V Y Y C
A R S Y F G S I F A Y W G Q G T L V T V S A;

(b) an immunoglobulin light chain comprising
the amino acid sequence:
                                  (SEQ ID NO: 14)
Q I V L T Q S P A I M S A S P G E K V T I S C S
A S S S V S Y L Y W Y Q Q K P G S S P K P W I F
R S S H R A S G V P A R F S G S G S G T S Y S L
T I S S M E A E D A A T Y Y C H Q Y Q S Y P P T
F G G G T K L E I K R A;

(c) an immunoglobulin heavy chain comprising
the amino acid sequence:
                                  (SEQ ID NO: 18)
E V Q L Q Q S G A D L V K P G A S V K L S C T A
S G F N I K D T Y I H W V K Q R P E Q G L E W I
G R I D P A N G H T E Y D P K F Q G R A T L T T
D T S S N T A Y L Q L F S L T S E D S A V Y F C
A R S Y Y G S I F A Y W G Q G T L V T V S A;
```

-continued (d) an immunoglobulin light chain comprising the amino acid sequence:

(SEQ ID NO: 22)
Q I V L T Q S P A I M S A S P G E K V T I S C S
A S S S V S Y L F W Y Q Q K P G S S P K P W I F
R T S Y L A S G V P A R F S G S G S G T S F S L
T I S S M E A E D A A T Y Y C H Q Y H T Y P P T
F G G G T K L E I K R A;

(e) an immunoglobulin heavy chain comprising the amino acid sequence:

(SEQ ID NO: 26)
E V Q L Q Q S G A E L V R S G A S V K L S C T T
S G F N I K D Y Y I H W V K Q R P E Q G L E W I
G W I D P E N G D T E Y A P K F Q G K A T M T A
D T S S N T A Y L Q L S S L T S A D T A V Y Y C
N A Y Y R Y D D G T W F P Y W G Q G T L V T V S
A;

(f) an immunoglobulin light chain comprising the amino acid sequence:

(SEQ ID NO: 30)
D I Q L T Q S P A S L S A S V G E T V T I T C R
A S G N I H S Y L A W Y Q Q K Q G K S P Q F L V
D N A K T L P D G V P S R F S V S G S G T Q Y S
L K I N S L Q P E D F G T Y Y C Q H F W N T P W
T F G G G T K L E I K R A;

(g) an immunoglobulin heavy chain comprising the amino acid sequence:

(SEQ ID NO: 34)
E V L L Q Q S V A E L V R P G A S V R L S C T A
S G F N I K D T Y I H W V R Q R P E Q G L E W F
G W I D P A N G Y T K Y A P N F Q G K A T L T T
D T S S N T A Y L H L S S L T S E D S A I Y Y C
A R G Y Y R Y Y S L D Y W G Q G T S V T V S S;

(h) an immunoglobulin light chain comprising the amino acid sequence:

(SEQ ID NO: 38)
D I Q M T Q T T S S L S A S L G D R V T I S C R
A S Q D I S N Y L N W Y Q Q K P D G T V K L L I
Y Y S S R L H S G V P S R F S G R G S G T D Y S
L T I S T L E Q E D I A T Y F C Q Q G K T L P L
T F G A G T K L E L K R A;

(i) an immunoglobulin heavy chain comprising the amino acid sequence:

(SEQ ID NO: 42)
E V Q L V D S G G G L V Q P G R S L K L S C A A
S G F T F S N H D M A W V R Q A P T K G L E W V
A S I T P S G G T T Y Y R D S V E G R F T V S R
D N V K S S L H L Q M D S L T S E D T A T Y Y C
A R Q N Y Y D G S Y Y Y G L Y Y F D Y W G Q G V
M V T V S S;

(j) an immunoglobulin light chain comprising the amino acid sequence:

(SEQ ID NO: 46)
D V L M T Q T P V S L P V S L G G Q V S I S C R
S S Q S L V Y S D G N T Y L H W Y L Q K P G Q S
P Q L L I Y R V S N R F S G V P D R F S G S G S
G T D F T L K I S R V E P E D L G L Y Y C L Q S
T H F P P T F G S G T K L E I K R A;

(k) an immunoglobulin heavy chain comprising the amino acid sequence:

(SEQ ID NO: 50)
E V Q L Q Q S G P E L V K P G A S V K I S C K V
S G Y T F T D Y Y M N W V K Q S H G K S L E W I
G D I N P N N G G A I Y N Q K F K G K A T S T V
D K S S S I A V M E L R S L T S E D S A V Y Y C
T S G I I T E I A E D F W G Q G T T L T V S S;
and -continued (l) an immunoglobulin light chain comprising the amino acid sequence:

(SEQ ID NO: 54)
D I V M T Q S Q K F M S T S V G D R V S V T C K
A S Q N V G T N V V W Y Q Q K P G Q S P K A L I
H S A S Y R Y S G V P D R F K G S G S G T D F T
L T I T N V Q S E D L A G F F C Q Q Y K T Y P Y
T F G G G T Q L E I K R A.

Embodiments of the invention include, e.g., compositions comprising any of the antibodies or polypeptides of the present invention association with a further chemotherapeutic agent, e.g., a cardiovascular agent, an adrenergic blocker, an antihypertensive agent, an angiotensin system inhibitor, an angiotensin-converting enzyme (ACE) inhibitor, a coronary vasodilator, a diuretic, an adrenergic stimulant or an HMG-CoA reductase inhibitor. In an embodiment of the invention, the further chemotherapeutic agent is ezetimibe, lovastatin, atorvastatin, pravastatin, rosuvastatin, fluvastatin, rivastatin, simvastatin, an azetidinone, bunolol hydrochloride, acebutolol, alprenoloi hydrochloride, atenolol, carteolol hydrochloride, celiprolol hydrochloride; cetamolol hydrochloride, labetalol hydrochloride, esmolol hydrochloride, levobetaxoloi hydrochloride, levobunolol hydrochloride, nadolol, practolol, propranolol hydrochloride, sotalol hydrochloride, timolol, timolol maleate, bisoprolol; bisoprolol fumarate, nebivalol, cicloprolol hydrochloride, dexpropranolol hydrochloride, diacetolol hydrochloride, dilevalol hydrochloride, exaprolol hydrochloride, flestolol sulfate, metalol hydrochloride, metoprolol 2-Propanol, metoprolol tartrate, pamatolol sulfate, penbutolol sulfate, practolol, tiprenolol hydrochloride or tolamolol. Embodiments of the invention also include those wherein the antibody or fragment is a humanized antibody, a monoclonal antibody, a labeled antibody, a bivalent antibody, a polyclonal antibody, a bispecific antibody, a chimeric antibody, a recombinant antibody, an anti-idiotypic antibody, a humanized antibody, a bispecific antibody, a camelized single domain antibody, a diabody, an scfv, an scfv dimer, a dsfv, a (dsfv)$_2$, a dsFv-dsfv', a bispecific ds diabody, an Fv, an Fab, an Fab', an F(ab')$_2$, or a domain antibody. In an embodiment of the invention, the antibody or antigen-binding fragment thereof is linked to an immunoglobulin constant region, e.g., a κ light chain, γ1 heavy chain, γ2 heavy chain, γ3 heavy chain or γ4 heavy chain. The present invention also provides a pharmaceutical composition comprising an antibody or antigen-binding fragment thereof of the present invention in association with a pharmaceutically acceptable carrier.

The present invention also provides a method for reducing total cholesterol level; low density lipoprotein cholesterol level; apolipoprotein B level; total cholesterol/high density lipoprotein ratio; or low density lipoprotein/high density lipoprotein ratio; or for treating hypercholesterolemia; hyperlipidemia; hypertriglyceridaemia; sitosterolemia; atherosclerosis; arteriosclerosis; coronary heart disease; vascular inflammation; or xanthoma, in a subject, comprising administering, to said subject, a therapeutically effective amount of any polypeptide or antibody or antigen-binding fragment thereof of the present invention as set forth herein; or pharmaceutical composition thereof; optionally, in association with a further chemotherapeutic agent, e.g., as set forth herein.

The present invention also provides a method for producing an antibody or antigen-binding fragment thereof of claim 1 comprising introducing one or more polynucleotides into one or more host cells; which polynucleotides encodes and direct expression of said heavy and/or light chain immunoglobulins; and growing said host cells under conditions whereby said heavy and light chain immunoglobulins are expressed; e.g., wherein said polynucleotide encoding and directing expression of said light chain and said polynucleotide encoding and directing expression of said heavy chain are in separate host cells.

BRIEF DESCRIPTION OF THE FIGURES

FIGS. 1A-1D. Mouse anti-human PCSK9 antibody mature variable region amino acid sequences. CDRs are indicated by dashed lines.

DETAILED DESCRIPTION OF THE INVENTION

The present invention includes methods and compositions for an innovative method for treating cholesterol disorders. The methods and compositions of the present invention are useful for treating cholesterol disorders by modulating the LDL receptor pathway. Specifically, the methods and compositions of the present invention antagonize the interaction between PCSK9 and LDLR and thereby lead to increased clearance of LDL from the bloodstream. In spite of formidable technical difficulties associated with blocking PPIs, the present invention provides a method for targeting and blocking this interaction, thus, leading to a beneficial effect with regard to blood cholesterol levels.

The term low density lipoprotein receptor (LDLR) includes any such receptor, e.g., human LDLR along with any allelic variant thereof. In one embodiment of the invention, full-length LDLR comprises the following amino acid sequence (see e.g., GenBank NM_000527.2):

(SEQ ID NO: 1)
MGPWGWKLRWTVALLLAAAGTAVGDRCERNEFQCQDGKCISYKWVCDG

SAECQDGSDESQETCLSVTCKSGDFSCGGRVNRCIPQFWRCDGQVDCD

NGSDEQGCPPKTCSQDEFRCHDGKCISRQFVCDSDRDCLDGSDEASCP

VLTCGPASFQCNSSTCIPQLWACDNDPDCEDGSDEWPQRCRGLYVFQG

DSSPCSAFEHCLSGECIHSSWRCDGGPDCKDKSDEENCAVATCRPDE

FQCSDGNCIHGSRQCDREYDCKDMSDEVGCVNVTLCEGPNKFKCHSGE

CITLDKVCNMARDCRDWSDEPIKECGTNECLDNNGGCSHVCNDLKIGY

ECLCPDGFQLVAQRRCEDIDECQDPDTCSQLCVNLEGGYKCQCEEGFQ

LDPHTKACKAVGSIAYLFFTNRHEVRKMTLDRSEYTSLIPNLRNVVAL

DTEVASNRIYWSDLSQRMICSTQLDRAHGVSSYDTVISRDIQAPDGLA

VDWIHSNIYWTDSVLGTVSVADTKGVKRKTLFRENGSKPRAIVVDPVH

GFMYWTDWGTPAKIKKGGLNGVDIYSLVTENIQWPNGITLDLLSGRLY

WVDSKLHSISSIDVNGGNRKTILEDEKRLAHPFSLAVFEDKVFWTDII

NEAIFSANRLTGSDVNLLAENLLSPEDMVLFHNLTQPRGVNWCERTTL

SNGGCQYLCLPAPQINPHSPKFTCACPDGMLLARDMRSCLTEAEAAVA

TQETSTVRLKVSSTAVRTQHTTTRPVPDTSRLPGATPGLTTVEIVTMS

HQALGDVAGRGNEKKPSSVRALSIVLPIVLLVFLCLGVFLLWKNWRLK

NINSINFDNPVYQKTTEDEVHICHNQDGYSYPSRQMVSLEDDVA

In an embodiment of the invention, a soluble LDLR fragment comprises the following amino acid sequence (Yamamoto et al, Cell (1984) 39:27-38):

(SEQ ID NO: 2)
AVGDRCERNEFQCQDGKCISYKWVCDGSAECQDGSDESQETCLSVTCK

SGDFSCGGRVNRCIPQFWRCDGQVDCDNGSDEQGCPPKTCSQDEFRCH

DGKCISRQFVCDSDRDCLDGSDEASCPVLTCGPASFQCNSSTCIPQLW

ACDNDPDCEDGSDEWPQRCRGLYVFQGDSSPCSAFEFHCLSGECIHSS

WRCDGGPDCKDKSDEENCAVATCRPDEFQCSDGNCIHGSRQCDREYDC

KDMSDEVGCVNVTLCEGPNKFKCHSGECITLDKVCNMARDCRDWSDEP

IKECGTNECLDNNGGCSHVCNDLKIGYECLCPDGFQLVAQRRCEDIDE

CQDPDTCSQLCVNLEGGYKCQCEEGFQLDPHTKACKAVGSIAYLFFTN

RHEVRKMTLDRSEYTSLIPNLRNVVALDTEVASNRIYWSDLSQRMICS

TQLDRAHGVSSYDTVISRDIQAPDGLAVDWIHSNIYWTDSVLGTVSVA

DTKGVKRKTLFRENGSKPRAIVVDPVHGFMYWTDWGTPAKIKKGGLNG

VDIYSLVTENIQWPNGITLDLLSGRLYWVDSKLHSISSIDVNGGNRKT

ILEDEKRLAHPFSLAVFEDKVFWTDIINEAIFSANRLTGSDVNLLAEN

LLSPEDMVLFHNLTQPRGVNWCERTTLSNGGCQYLCLPAPQINPHSPK

FTCACPDGMLLARDMRSCLTEAEAAVATQETSTVRLKVSSTAVRTQHT

TTRPVPDTSRLPGATPGLTTVEIVTMSHQALGDVAGRGNEKKPSSVR

In an embodiment of the invention, the EGF-A domain of LDL receptor comprises the amino acid sequence: GTNECLDNNGGCSHVCNDLKIGYECLCP-DGFQLVAQRRCEDI (SEQ ID NO: 3)

The term "subject" includes any animal, e.g., a mammal such as a human.

PCSK9

The present invention includes compositions and methods comprising antibodies and antigen-binding fragment thereof which bind specifically to PCSK9, for example, human PCSK9. In some embodiments of the invention, specific PCSK9 polypeptide sequences or antigenic fragments thereof from various species set forth below may be used as an antigen:

HUMAN gi|31317307|ref|NP_777596.2| proprotein convertase subtilisin/kexin type 9 preproprotein [*Homo sapiens*]

(SEQ ID NO: 4)
MGTVSSRRSWWPLPLLLLLLLLLGPAGARAQEDEDGDYEELVLALRSE

EDGLAEAPEHGTTATFHRCAKDPWRLPGTYVVVLKEETHLSQSERTAR

RLQAQAARRGYLTKILHVFHGLLPGFLVKMSGDLLELALKLPHVDYIE

EDSSVFAQSIPWNLERITPPRYRADEYQPPDGGSLVEVYLLDTSIQSD

HREIEGRVMVTDFENVPEEDGTRFHRQASKCDSHGTHLAGVVSGRDAG

VAKGASMRSLRVLNCQGKGTVSGTLIGLEFIRKSQLVQPVGPLVVLLP

LAGGYSRVLNAACQRLARAGVVLVTAAGNFRDDACLYSPASAPEVITV

GATNAQDQPVTLGTLGTNFGRCVDLFAPGEDIIGASSDCSTCFVSQSG

TSQAAAHVAGIAAMMLSAEPELTLAELRQRLIHFSAKDVINEAWFPED

QRVLTPNLVAALPPSTHGAGWQLFCRTVWSAHSGPTRMATAVARCAPD

EELLSCSSFSRSGKRRGERMEAQGGKLVCRAHNAFGGEGVYAIARCCL

-continued
LPQANCSVHTAPPAEASMGTRVHCHQQGHVLTGCSSHWEVEDLGTHKP

PVLRPRGQPNQCVGHREASIHASCCHAPGLECKVKEHGIPAPQEQVTV

ACEEGWTLTGCSALPGTSHVLGAYAVDNTCVVRSRDVSTTGSTSEGAV

TAVAICCRSRHLAQASQELQ

CHIMP gi|114556790|ref|XP_001154126.1|PREDICTED: proprotein convertase subtilisin/kexin type 9 [*Pan troglodytes*]

(SEQ ID NO: 5)
MGTVSSRRSWWPLPLLLLLLLLLGPAGARAQEDEDGLAEAPEHGTTAT

FHRCAKDPWRLPGTYVVVLKEETHLSQSERTARRLQAQAARRGYLTKI

LHVFHGLLPGFLVKMSGDLLELALKLPHVDYIEEDSSVFAQSIPWNLE

RITPPRYRADEYQPPDGGSLVEVYLLDTSIQSDHREIEGRVMVTDFEN

HVPEEDGTRFHRQASKCDSHGTHLAGVVSGRDAGVAKGASMRSLRVLN

CQGKGTVSGTLIGLEFIRKSQLVQPVGPLVVLLPLAGGYSRVLNAACQ

RLARAGVVLVTAAGNFRDDACLYSPASAPEVITVGATNAQDQPVTLGT

LGTNFGRCVDLFAPGEDIIGASSDCSTCFVSQSGTSQAAAHVAGIAAM

MLSAEPELTLAELRQRLIHFSAKDVINEAWFPEDQRVLTPNLVAALPP

STHGAGWQLFCRTVWSAHSGPTRMATAVARCAPDEELLSCSSFSRSGK

RRGERMEAQGGKLVCRAHNAFGGEGVYAIARCCLLPQANCSIHTAPPA

EAGMGTRVHCHQQGHVLTGCSSHWEVEDLGTHKPPMLRPRGQPNQCVG

HREASIHASCCRAPGLECKVKEHGIPAPQEQVTVACEEGWTLTGCSAL

PGTSHVLGAYAVDNTCVVRSRDVSTAGSTSEEAVAAVAICCRSRHLAQ

ASQELQ

MOUSE gi|23956352|ref|NP_705793.1| proprotein convertase subtilisin/kexin type 9 [*Mus musculus*]

(SEQ ID NO: 6)
MGTHCSAWLRWPLLPLLPPLLLLLLLLLCPTGAGAQDEDGDYEELMLALPS

QEDGLADEAAHVATATFRRCSKEAWRLPGTYIVVLMEETQRLQIEQTAHR

LQTRAARRGYVIKVLHIFYDLFPGFLVKMSSDLLGLALKLPHVEYIEEDS

FVFAQSIPWNLERIIPAWHQTEEDRSPDGSSQVEVYLLDTSIQGAHREIE

GRVTITDFNSVPEEDGTRFHRQASKCDSHGTHLAGVVSGRDAGVAKGTSL

HSLRVLNCQGKGTVSGTLIGLEFIRKSQLIQPSGPLVVLLPLAGGYSRIL

NAACRHLARTGVVLVAAAGNFRDDACLYSPASAPEVITVGATNAQDQPVT

LGTLGTNFGRCVDLFAPGKDIIGASSDCSTCFMSQSGTSQAAAHVAGIVA

RMLSREPTLTLAELRQRLIHFSTKDVINMAWFPEDQQVLTPNLVATLPPS

THETGGQLLCRTVWSAHSGPTRTATATARCAPEEELLSCSSFSRSGRRRG

DWIEAIGGQQVCKALNAFGGEGVYAVARCCLVPRANCSIHNTPAARAGLE

THVHCHQKDHVLTGCSFHWEVEDLSVRRQPALRSRRQPGQCVGHQAASVY

ASCCHAPGLECKIKEHGISGPSEQVTVACEAGWTLTGCNVLPGASLTLGA

YSVDNLCVARVHDTARADRTSGEATVAAAICCRSRPSAKASWVQ

RAT gi|77020250|ref|NP_954862.2| proprotein convertase subtilisin/kexin type 9 [*Rattus norvegicus*]

(SEQ ID NO: 7)
MGIRCSTWLRWPLSPQLLLLLLLLCPTGSRAQDEDGDYEELMLALPSQEDS

LVDEASHVATATFRRCSKEAWRLPGTYVVVLMEETQRLQVEQTAHRLQTW

AARRGYVIKVLHVFYDLFPGFLVKMSSDLLGLALKLPHVEYIEEDSLNFA

QSIPWNLERIIPAWQQTEEDSSPDGSSQVEVYLLDTSIQSGHREIEGRVT

ITDFNSVPEEDGTRFHRQASKCDSHGTHLAGVVSGRDAGVAKGTSLHSLR

VLNCQGKGTVSGTLIGLEFIRKSQLIQPSGPLVVLLPLAGGYSRILNTAC

QRLARTGVVLVAAAGNFRDDACLYSPASAPEVITVGATNAQDQPVTLGTL

GTNFGRCVDLFAPGKDIIGASSDCSTCYMSQSGTSQAAAHVAGIVAMMLN

RDPALTLAELRQRLILFSTKDVINMAWFPEDQRVLTPNRVATLPPSTQET

GGQLLCRTVWSAHSGPTRTATATARCAPEEELLSCSSFSRSGRRRGDRIE

AIGGQQVCKALNAFGGEGVYAVARCCLLPRVNCSIHNTPAARAGPQTPVH

CHQKDHVLTGCSFHWEVENLRAQQQPLLRSRHQPGQCVGHQEASVHASCC

HAPGLECKIKEHGIAGPAEQVTVACEAGWTLTGCNVLPGASLPLGAYSVD

NVCVARIRDAGRADRTSEEATVAAAICCRSRPSAKASWVHQ

EGF-A

The present invention also provides methods for reducing total cholesterol level, low density lipoprotein cholesterol level, apolipoprotein B level, total cholesterol/high density lipoprotein ratio or low density lipoprotein/high density lipoprotein ratio, in a subject, by administering, to the subject, a polypeptide comprising an LDL receptor EGF-A domain optionally in association with a further chemotherapeutic agent (e.g., as set forth herein) or a pharmaceutical composition thereof which comprises a pharmaceutically acceptable carrier. The EGF-A domain of LDL receptor binds to PCSK9 and, without being bound by any particular theory or mechanism, may reduce the activity of PCSK9 by competing with the full, endogenous LDL receptor for binding to PCSK9.

For example, in an embodiment of the invention, the EGF-A domain comprises or consists of the following amino acid sequence:

(SEQ ID NO: 3)
GTNECLDNNGGCSHVCNDLKIGYECLCPDGFQLVAQRRCEDI.

In an embodiment of the invention, human LDL receptor comprises the following amino acid sequence:

(SEQ ID NO: 1)

```
  1 mgpwgwklrw tvalllaaag tavgdrcern efqcqdgkci sykwvcdgsa ecqdgsdesq
 61 etclsvtcks gdfscggrvn rcipqfwrcd gqvdcdngsd eqgcppktcs gdefrchdgk
121 cisrqfvcds drdcldgsde ascpvltcgp asfqcnsstc ipqlwacdnd pdcedgsdew
181 pqrcrglyvf qgdsspcsaf efhclsgeci hsswrcdggp dckdksdeen cavatcrpde
241 fqcsdgncih gsrqcdreyd ckdmsdevgc vnvtlcegpn kfkchsgeci tldkvcnmar
301 dcrdwsdepi kecgtnecld nnggcshvcn dlkigyeclc pdgfqlvaqr rcedidecqd
361 pdtcsqlcvn leggykcqce egfqldphtk ackavgsiay lfftnrhevr kmtldrseyt
421 slipnlrnvv aldtevasnr iywsdlsqrm icstqldrah gvssvdtvis rdiqapdgla
481 vdwihsniyw tdsvlgtvsv adtkgvkrkr lfrengskpr aivvdpvhgf mywtdwgtpa
541 kikkgglngv diyslvteni qwpngitldl lsgrlywvds klhsissidv nggnrktile
601 dekrlahpfs lavfedkvfw tdiineaifs anrltgsdvn llaenllspe dmvlfhnltq
661 prgvnwcert tlsnggcqyl clpapqinph spkftcacpd gmllardmrs clteaeaava
721 tqetstvrlk vsstavrtqh tttrpvpdts rlpgatpglt tveivtmshq algdvagrgn
781 ekkpssvral sivlpivllv flclgvfllw knwrlknins infdnpvyqk ttedevhich
841 nqdgysypsr qmvsleddva
```

The EGF-A domain is underscored and in bold faced text. See also Genbank accession nos.: NP_000518, EAW84170, BAD92646.1 or AAF24515.1.

The present invention also comprises an isolated polypeptide comprising or consisting of an EGF-A polypeptide, for example, in a pharmaceutical composition which includes a pharmaceutically acceptable carrier. The present invention also provides such a polypeptide optionally fused to any other heterologous polypeptide which is not naturally contiguous with the other, immediately adjacent LDL receptor sequences as well as methods of treatments comprising administration of the fused polypeptide e.g., as discussed herein. Any such polypeptide may be referred to herein as an "EGF-A polypeptide" and a polynucleotide encoding an EGF-A polypeptide may be referred to as an "EGF-A polynucleotide".

For example, in an embodiment of the invention, the EGF-A polynucleotide comprises the following nucleotide sequence:

(SEQ ID NO: 9)
GGTACTAATGAATGTCTTGATAATAATGGTGGTTGTTCTCATGTTTGTAA

TGATCTTAAAATTGGTTATGAATGTCTTTGTCCTGATGGTTTTCAACTTG

TTGCTCAACGTCGTTGTGAAGATATT

As discussed above, the present invention also includes fusions which include the EGF-A polypeptides and polynucleotides of the present invention and a second polypeptide or polynucleotide moiety, which may be referred to as a "tag". The fused polypeptides of the invention may be conveniently constructed, for example, by insertion of a polynucleotide of the invention or fragment thereof into an expression vector. The fusions of the invention may include tags which facilitate purification or detection. Such tags include glutathione-S-transferase (GST), hexahistidine (HisB) tags, maltose binding protein (MBP) tags, haemagglutinin (HA) tags, cellulose binding protein (GBP) tags and myc tags. Detectable tags such as $^{32}P$, $^{35}S$, $^{3}H$, $^{14}C$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

Any isolated polynucleotide encoding such an EGF-A polypeptide of the present invention also forms part of the present invention along with any vector comprising such a polynucleotide and a host cell (e.g., bacterial host cell or eukaryotic cell) comprising such a vector. Such polynucleotides operably associated with an expression control sequence (e.g., a promoter) also form part of the present invention.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42) prokaryotic expression vectors such as the β-lactamase promoter (Villa-Komaroff, et al., (1978) Proc, Natl. Acad. Sci. USA 75; 3727-3731), or the tac promoter (DeBoer, et al., (1983) Proc. Natl, Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell or other expression system when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, of al., Cloning Vectors: A Laboratory Manual, 1985 and Supplements, Elsevier, N.Y., and Rodriguez et al. (eds.), Vectors: A Survey of Molecular Cloning Vectors and Their Uses, 1988, Buttersworth, Boston, Mass.

The term "expression system" includes, for example, a host cell and compatible vector which, under suitable conditions, can express a protein or nucleic acid which is carried by the vector and introduced to the host cell. Common expression systems include E. coli host cells and plasmid vectors, insect host cells and Baculovirus vectors, and mammalian host cells and vectors.

Prokaryotic host-vector systems include a wide variety of vectors for many different species. A representative vector for amplifying DNA is pBR322 or many of its derivatives (e.g., pUC18 or 19), Vectors that can be used to express the EGF-A polypeptides include, but are not limited to, those containing the lac promoter (pUC-series); trp promoter (pBR322-trp); 1 pp promoter (the plN-series); lambda-pP or pR promoters (pOTS); or hybrid promoters such as ptac (pDR540). See Brosius et al., "Expression Vectors Employing Lambda-, trp-, lac-, and Epp-derived Promoters", in Rodriguez and Denhardt (eds.) Vectors: A Survey of Molecular Cloning Vectors and Their Uses, 1988, Buttersworth, Boston, pp. 205-236. Many polypeptides can be expressed, at high levels, in an E. coli/T7 expression system as disclosed in U.S. Pat. Nos. 4,952,496, 5,693,489 and 5,869,320 and in Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.

The present invention comprises methods of expression an EGF-A polypeptide of the present invention comprising introducing a vector comprising a polynucleotide encoding said polypeptide (e.g., operably associated with an expression control sequence such as a promoter) into a suitable host cell and propagating (e.g., growing in a suitable liquid growth medium) the host cell under conditions which are suitable to expression of the polypeptide from the polynucleotide in the vector.

Also part of the present invention is any isolated polypeptide with about 90% or more amino acid sequence similarity or identity to that of SEQ ID NO: 3. In an embodiment of the invention, such a polypeptide must bind to PCSK9 or a functional fragment thereof; or inhibit binding of PCSK9 and LDL receptor or any functional fragment of either; or must exhibit the ability to reduce total cholesterol level, low density lipoprotein cholesterol level, apolipoprotein B level, total cholesterol/high density lipoprotein ratio or low density lipoprotein/high density lipoprotein ratio in a subject, such as an acceptable animal model (e.g., a mammal such as a dog, primate, rabbit, mouse or rat) or a human.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Assubel, et al. (eds.), Current Protocols in Molecular Biology, John Wiley & Sons, Inc. (1994).

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein.

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, in an embodiment of the invention, be an essentially homogeneous composition of molecules but may contain some heterogeneity.

The present invention contemplates any superficial or slight modification to the amino acid or nucleotide sequences which correspond to the EGF-A polypeptides and polynucleotides of the invention. In particular, the present invention contemplates sequence conservative variants of the nucleic acids which encode the EGF-A polypeptides of the invention. "Sequence-conservative variants" of an EGF-A polynucleotide sequence are those in which a change of one or more nucleotides in a given codon results in no alteration in the amino acid encoded at that position. Function-conservative variants of the EGF-A polypeptides of the invention are also contemplated by the present invention. "Function-conservative variants" are those in which one or more amino acid residues in an EGF-A polypeptide have been changed without altering the overall conformation and/or function of the polypeptide (e.g., ability to bind to PCSK9 or inhibit binding of PCSK9 and an LDL receptor or fragment thereof), including, but, by no means limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, praline, tyrosine, phenylalanine, tryptophan and methionine; acidic amino acids which may be interchangeable include aspartic acid and glutamic acid and basic amino acids which may be interchangeable include histidine, lysine and arginine.

The present invention includes polynucleotides encoding EGF-A (e.g., SEQ ID NO: 9) and functional fragments thereof as well as nucleic acids which hybridize to the polynucleotides. In an embodiment of the invention, the nucleic acids hybridize under low stringency conditions, under moderate stringency conditions or under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions are 55° C., 5×SSC, 0.1% SDS, 0.25% milk, and no formamide at 42° C.; or 30% formamide, 5×SSC, 0.5% SDS at 42° C. Typical, moderate stringency hybridization conditions are similar to the low stringency conditions except the hybridization is carried out in 40% formamide, with 5× or 6×SSC at 42° C. High stringency hybridization conditions are similar to low stringency conditions except the hybridization conditions are carried out in 50% formamide, 5× or 6×SSC and, optionally, at a higher temperature (e.g., higher than 42° C.; 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.54 For hybridization with shorter nucleic acids, i.e., oligonucleotides, the position of mismatches becomes more important, and the length of the oligonucleotide determines its specificity (see Sambrook, et al., supra). In an embodiment of the invention, such a polynucleotide encodes a polypeptide that must bind to PCSK9 or a functional fragment thereof; or inhibit binding of PCSK9 and LDL receptor or any functional fragment of either; or must exhibit the ability to reduce total cholesterol level, low density lipoprotein cholesterol level, apolipoprotein B level, total cholesterol/high density lipoprotein ratio or low density lipoprotein/high density lipoprotein ratio in a subject, such as art acceptable animal model (e.g., a mammal such as a dog, primate, rabbit, mouse or rat) or a human.

Also included in the present invention are polynucleotides comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to a reference nucleotide sequence (SEQ ID NO: 9) or reference amino acid sequence (SEQ ID NO: 3), when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference EGF-A amino acid sequence of SEQ ID NO: 3, when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3," M. O. Dayhoff (ed.), pp. 353-358, Natl. Biomed. Res. Found., Washington, D. C.: Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mot Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S.F. "Evaluating the statistical significance of multiple distinct local alignments." in *Theoretical and Computational Methods in Genome Research* (S. Suhai, ed.), (1997) pp. 1-14, Plenum, New York.

Antibodies

The present invention includes methods and compositions comprising anti-PCSK9 antibodies and antigen-binding fragments thereof. The term anti-PCSK9 antibody or the like includes any antibody that binds specifically to PCSK9 (e.g., human PCSK9). The anti-PCSK9 antibodies and antigen-binding fragments thereof used in the present invention include antibodies and fragments which were raised against or bind to the whole PCSK9 protein as well as antibodies raised against or bind to particular short epitopes within PCSK9, e.g., the catalytic domain of PCSK9 or a portion thereof (e.g., binding to an VFAQSIPWNLER epitope (SEQ ID NO: 8)) or a C-terminal domain of PCSK9 (i.e., C-terminal relative to the cat domain of PCSK9)-having amino acids SRSGKRRGERMEA (amino acids 490-502 of SEQ ID NO: 4). In an embodiment of the invention, the anti-PCSK9 antibody or antigen-binding fragment thereof binds to the domain of PCSK9 which interacts with the EGF-A domain of the LDL receptor.

Specific isolated mouse anti-human PCSK9 antibody immunoglobulin sequences of the present invention are set forth below. CDR sequences for each immunoglobulin chain are underscored.

11B5 Immunoglobulin Heavy Chain (SEQ ID NO: 10)
E V Q L Q Q S G A E L V K P G A S V T L S C T A S
G F N I K D T Y M H W V N Q R P E Q G L V W I G R
I D P A N G H T E Y D P K F Q D K A T I T T D T S
S N T A Y L H L S S L T S G D T A V Y Y C A R S Y
F G S I F A Y W G Q G T L V T V S A (SEQ ID NO: 11)
HCDR1: G F N I K D T Y M H (SEQ ID NO: 12)
HCDR2: R I D P A N G H T E Y D P K F Q D (SEQ ID NO: 13)
HCDR3: S Y F G S I F A Y 11B5 Immunoglobulin Light Chain (SEQ ID NO: 14)
Q I V L T Q S P A I M S A S P G E K V T I S C S A
S S S V S Y L Y W Y Q Q K P G S S P K P W I F R S
S H R A S G V P A R F S G S G S G T S Y S L T I S
S M E A E D A A T Y Y C H Q Y Q S Y P P T F G G G
T K L E I K R A (SEQ ID NO: 15)
LCDR1: S A S S S V S Y L Y (SEQ ID NO: 16)
LCDR2: R S S H R A S (SEQ ID NO: 17)
LCDR3: H Q Y Q S Y P P T 75B9 Immunoglobulin Heavy Chain (SEQ ID NO: 18)
E V Q L Q Q S G A D L V K P G A S V K L S C T A S
G F N I K D T Y I H W V K Q R P E Q G L E W I G R
I D P A N G H T E Y D P K F Q G R A T L T T D T S
S N T A Y L Q L F S L T S E D S A V Y F C A R S Y
Y G S I F A Y W G Q G T L V T V S A (SEQ ID NO: 19)
HCDR1: G F N I K D T Y I H (SEQ ID NO: 20)
HCDR2: R I D P A N G H T E Y D P K F Q G (SEQ ID NO: 21)
HCDR3: S Y Y G S I F A Y 75B9 immunoglobulin light chain (SEQ ID NO: 22)
Q I V L T Q S P A I M S A S P G E K V T I S C S A
S S S V S Y L F W Y Q Q K P G S S P K P W I F R T
S Y L A S G V P A R F S G S G S G T S F S L T I S
S M E A E D A A T Y Y C H Q Y H T Y P P T F G G G
T K L E I K R A (SEQ ID NO: 23)
LCDR1: S A S S S V S Y L F (SEQ ID NO: 24)
LCDR2: R T S Y L A S (SEQ ID NO: 25)
LCDR3: H Q Y H T Y P P T 77D10 Immunoglobulin Heavy Chain (SEQ ID NO: 26)
E V Q L Q Q S G A E L V R S G A S V K L S C T T S
G F N I K D Y Y I H W V K Q R P E Q G L E W I G W
I D P E N G D T E Y A P K F Q G K A T M T A D T S
S N T A Y L Q L S S L T S A D T A V Y Y C N A Y Y
R Y D D G T W F P Y W G Q G T L V T V S
A (SEQ ID NO: 27)
HCDR1: G F N I K D Y Y I H (SEQ ID NO: 28)
HCDR2: W I D P E N G D T E Y A P K F Q G (SEQ ID NO: 29)
HCDR3: Y Y R Y D D G T W F P Y 77D10 immunoglobulin light chain (SEQ ID NO: 30)
D I Q L T Q S P A S L S A S V G E T V T I T C R A
S G N I H S Y L A W Y Q Q K Q G K S P Q F L V D N
A K T L P D G V P S R F S V S G S G T Q Y S L K I
N S L Q P E D F G T Y Y C Q H F W N T P W T F G G
G T K L E I K R A (SEQ ID NO: 31)
LCDR1: R A S G N I H S Y L A (SEQ ID NO: 32)
LCDR2: N A K T L P D (SEQ ID NO: 33)
LCDR3: Q H F W N T P W T

29C10 Immunoglobulin Heavy Chain (SEQ ID NO: 34)
E V L L Q Q S V A E L V R P G A S V R L S C T A S G F N I K D T Y I H W V R Q R P E Q G L E W F G W I D P A N G Y T K Y A P N F Q G K A T L T T D T S S N T A Y L H L S S L T S E D S A I Y Y C A R G Y Y R Y Y S L D Y W G Q G T S V T V S S (SEQ ID NO: 35)
HCDR1: G F N I K D T Y I H (SEQ ID NO: 36)
HCDR2: W I D P A N G Y T K Y A P N F Q G (SEQ ID NO: 37)
HCDR3: G Y Y R Y Y S L D Y

29C10 Immunoglobulin Light Chain (SEQ ID NO: 38)
D I Q M T Q T T S S L S A S L G D R V T I S C R A S Q D I S N Y L N W Y Q Q K P D G T V K L L I Y Y S S R L H S G V P S R F S G R G S G T D Y S L T I S T L E Q E D I A T Y F C Q Q G K T L P L T F G A G T K L E L K R A (SEQ ID NO: 39)
LCDR1: R A S Q D I S N Y L N (SEQ ID NO: 40)
LCDR2: Y S S R L H S (SEQ ID NO: 41)
LCDR3: Q Q G K T L P L T

22D11 Immunoglobulin Heavy Chain (SEQ ID NO: 42)
E V Q L V D S G G G L V Q P G R S L K S L C A A S G F T F S N H D M A W V R Q A P T K G L E W V A S I T P S G G T T Y Y R D S V E G R F T V S R D N V K S S L H L Q M D S L T S E D T A T Y Y C A R Q N Y Y D G S Y Y Y G L Y Y F D Y W G Q G V M V T V S S (SEQ ID NO: 43)
HCDR1: G F T F S N H D M A (SEQ ID NO: 44)
HCDR2: S I T P S G G T T Y Y R D S V E G (SEQ ID NO: 45)
HCDR3: Q N Y Y D G S Y Y Y G L Y Y F D Y

22D11 Immunoglobulin Light Chain (SEQ ID NO: 46)
D V L M T Q T P V S L P V S L G G Q V S I S C R S S Q S L V Y S D G N T Y L H W Y L Q K P G Q S P Q L L I Y R V S N R F S G V P D R F S G S G S G T D F T L K I S R V E P E D L G L Y Y C L Q S T H F P P T F G S G T K L E I K R A (SEQ ID NO: 47)
LCDR1: R S S Q S L V Y S D G N T Y L H (SEQ ID NO: 48)
LCDR2: R V S N R F S (SEQ ID NO: 49)
LCDR3: T Q S T H F P P T

1F11/1G11 Immunoglobulin Heavy Chain (SEQ ID NO: 50)
E V Q L Q Q S G P E L V K P G A S V K I S C K V S G Y T F T S Y Y M N W V K Q S H G K S L E W I G D I N P N N G G A I Y N Q K F K G K A T L T V D K S S S I A Y M E L R S L T S E D S A V Y Y C T S G I I T E I A E D F W G Q G T T L T V S S (SEQ ID NO: 51)
HCDR1: G Y T F T D Y Y M N (SEQ ID NO: 52)
HCDR2: D I N P N N G G A I Y N Q K F K G (SEQ ID NO: 53)
HCDR3: G I I T E I A E D F

F11/1G11 Immunoglobulin Light Chain (SEQ ID NO: 54)
D I V M T Q S Q K F M S T S V G D R V S V T C K A S Q N V G T N V V W Y Q Q K P G Q S P K A L I H S A S Y R Y S G V P D R F K G S G S G T D F T L T I T N V Q S E D L A G F F C Q Q Y K T Y P Y T F G G G T Q L E I K R A (SEQ ID NO: 55)
LCDR1: K A S Q N V G T N V V (SEQ ID NO: 56)
LCDR2: S A S Y R Y S (SEQ ID NO: 57)
LCDR3: Q Q Y K T Y P Y T The present invention includes isolated polypeptides (e.g., antibodies and antigen-binding fragments thereof) comprising one or more (e.g., 3) CDRs taken from the light and/or heavy chain immunoglobulin set forth above as defined by the convention set forth in Kabat, "Sequences of Proteins of Immunological Interest" (National Institutes of Health, Bethesda, Md., 1987 and 1991) or in Chothia et al., J. Mol. Biol. 196:901 (1987); Nature 342:878 (1989); and J. Mol. Biol. 186:651 (1989) (Kabat or Chothia) or Al-Lazikani et al., J. Mol. Biol. 273: 927-948 (1997).

Thus, the invention includes any antibody or antigen-binding fragment thereof comprising one or more of the light chain and/or heavy chain immunoglobulin CDRs set forth above, in an embodiment of the invention, the antibody or fragment comprises all 3 light chain and/or all 3 heavy chain CDRs, in the order specified above. Embodiments of the invention include anti-PCSK9 antibodies and antigen-binding fragments thereof, e.g., as set forth above wherein, the antibodies or fragments are monoclonal antibodies, camelized single domain antibodies, polyclonal antibodies, bispecific antibodies, chimeric antibodies, recombinant antibodies, anti-idiotypic antibodies, humanized antibodies, bispecific antibodies, diabodies, single chain antibodies, disulfide Fvs (dsfv), Fvs, Fabs, Fab' s, F(ab')$_2$s and domain antibodies. Thus, the term antibody covers, but is not limited to, monoclonal antibodies, polyclonal antibodies, multispecific antibodies (e.g., bispecific antibodies). The term antigen-binding fragment of an antibody encompasses a fragment or a derivative of an antibody, typically including at least a portion of the antigen-binding or variable regions (e.g., one or more CDRs) of the parental antibody, that retains at least some of the binding specificity of the parental antibody. Examples of antibody antigen-binding fragments include, but are not limited to, Fab, Fab', F(ab')$_2$, and Fv fragments; dsFv; (dsFv)$_2$; ds diabodies; dsFv-dsFv'; single-chain antibody molecules, e.g., sc-Fv, sc-Fv dimers (bivalent diabodies); bispecific diabodies; and multispecific antibodies formed from antibody fragments.

The present invention includes anti-PCSK9 antibodies and antigen-binding fragments thereof which binds specifically to PCSK9, for example, human PCSK9. In an embodiment of the invention an antibody or fragment that binds specifically to human PCSK9 binds preferentially to human PCSK9 as compared to that of rat, mouse or chimp PCSK9. Preferential binding to human PCSK9 means binding with an affinity which is greater than that of rat, mouse or chimp PCSK9 binding to any degree (e.g., 1%, 10%, 50%, 100%, or 10× higher affinity). In an embodiment of the invention, an anti-human PCSK9 antibody binds to human PCSK9 without any detectable binding to any other species of PCSK9 (e.g., no detectable binding to a mouse or rat PCSK9). Specific anti-PCSK9 binding refers to binding of the antibody to PCSK9 or an antigenic fragment thereof with a Kd at least about 100-fold higher than that of any other protein that might be bound and a minimum Kd of about 500 nM.

Any suitable method for generating antibodies may be used. For example, a recipient may be immunized with PCSK9 or an immunogenic fragment thereof. Any suitable method of immunization can be used. Such methods can include adjuvants, other immunostimulants, repeated booster immunizations, and the use of one or more immunization routes. Any suitable source of PCSK9 can be used as the immunogen for the generation of the antibodies and fragments of the compositions and methods disclosed herein. Such forms include, but are not limited whole protein, peptide(s), and epitopes generated through recombinant, synthetic, chemical or enzymatic degradation means known in the art, Any form of the antigen can be used to generate the antibody that is sufficient to generate a biologically active antibody. Thus, the eliciting antigen may be a single epitope, multiple epitopes, or the entire protein alone or in combination with one or more Immunogenicity enhancing agents known in the art. The eliciting antigen may be an isolated full-length protein, a cell surface protein (e.g., immunizing with cells transfected with at least a portion of the antigen), or a soluble protein fragment.

Any suitable method can be used to elicit an antibody with the desired biologic properties to inhibit PCSK9. Monoclonal antibodies (mAbs) may be prepared from various mammalian hosts, such as mice, rats, other rodents, humans, other primates, etc. Description of techniques for preparing such monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or an antigen binding fragment thereof by screening a DNA library from human B cells according, e.g., to the general protocol outlined by Huse et al. (1989) Science 246:1275-1281.

Other suitable techniques involve selection of libraries of antibodies in phage or similar vectors. See, e.g., Huse et al. supra; and Ward et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance that provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) Proc. Nat'l Acad. Sci. USA 86:10029-10033; or made in transgenic mice, see Mendez et al. (1997) Nature Genetics 15:146-156.

Mice which produce human immunoglobulins when immunized with an given antigen are also available in the art. See e.g., Lonberg, N., et al., (1994) Nature 368(6474): 856-859; Lonberg, N. (1994) Handbook of Experimental Pharmacology 113:49-101; Lonberg, N., et al., (1995) Intern. Rev. Immunol. 13:65-93, and Harding, F., et al., (1995) Ann. N.Y. Acad. Sci. 764:536-546); Taylor, L., et al., (1992) Nucleic Acids Research 20:6287-6295; Chen, J., et al., (1993) International Immunology 5: 647-656; Tuaillon, et al., (1993) Proc. Natl. Acad. Sci. USA 90:3720-3724; Choi, et al., (1993) Nature Genetics 4:117-123; Chen, J., et al., (1993) EMBO J. 12: 821-830; Tuaillon, et al., (1994) J. Immunol. 152:2912-2920; Lonberg, et al., (1994) Nature 368(6474): 856-859; Lonberg, N. (1994) Handbook of Experimental Pharmacology 113:49-101; Taylor, L., et al., (1994) International Immunology 6: 579-591; Lonberg, N., et al., (1995) intern. Rev. Immunol. Vol. 13: 65-93; Harding, F., et al., (1995) Ann. N.Y. Acad. Sci. 764:536-546; Fishwild, D., et al., (1996) Nature Biotechnology 14: 845-851 and Harding, et al., (1995) Annals NY Acad. Sci. 764:536-546. See further, U.S. Pat. Nos. 5,545,806; 5,569,825; 5,625,126; 5,633,425; 5,789,650;

5,877,397; 5,661,016; 5,814,318; 5,874,299; 5,770,429 and 5,545,807; and International Patent Application Publication Nos. WO 98/24884; WO 94/25585; WO 93/12227; WO 92/22645 and WO 92/03918.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

"Disulfide stabilized Fv fragments" and "dsFv" include molecules having a variable heavy chain ($V_H$) and/or a variable light chain ($V_L$) which are linked by a disulfide bridge.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the $V_H$ and $V_L$ chains to pair and form a binding site (e.g., 5-12 residues long). For a review of scFv, see Pluckthun (1994) THE PHARMACOLOGY OF MONOCLONAL ANTIBODIES, Vol, 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen-binding sites. In some instances, the two binding sites have the same antigen specificities. However, bivalent antibodies may be bispecific. For example, the present invention comprises scfv dimers and dsfv dimers, each of which scfv and dsfv moieties may have a common or different antigen binding specificity.

In an embodiment of the invention, a $(dsfv)_2$ comprises three peptide chains: two $V_H$ moieties linked by a peptide linker and bound by disulfide bridges to two $V_L$ moieties. In an embodiment of the invention, a bispecific ds diabody comprises a $VH_1$-$VL_2$ (tethered by a peptide linker) linked, by a disulfide bridge between the $VH_1$ and $VL_1$, to a $VL_1$-$VH_2$ moiety (also tethered by a peptide linker). In an embodiment of the invention, a bispecific dsfv-dsfv' also comprises three peptide chains: a $VH_1$-$VH_2$ moiety wherein the heavy chains are linked by a peptide linker (e.g., a long flexible linker) and are bound to $VL_1$ and $VL_2$ moieties, respectively, by disulfide bridges; wherein each disulfide paired heavy and light chain has a different antigen specificity. In an embodiment of the invention, an scfv dimer (a bivalent diabody) comprises a $V_H$-$V_L$ moiety wherein the heavy and light chains are bound to by a peptide linker and dimerized with another such moiety such that $V_H$s of one chain coordinate with the $V_L$s of another chain and form two identical binding sites. In an embodiment of the invention a bispecific diabody comprises $VH_1$-$VL_2$ moiety (linked by a peptide linker) associated with a $VL_1$-$VH_2$ (linked by a peptide linker), wherein the $VH_1$ and Vt., coordinate and the $VH_2$ and $VL_2$ coordinate and each coordinated set has diverse antigen specificities.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made recombinantly or by the hybridoma method first described by Kohler et al. (1975) *Nature* 256: 495, or may be made by recombinant DNA methods (see, e.g., U.S. Pat. No. 4,816, 567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

Monoclonal antibodies include "chimeric" antibodies (immunogiobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984) *Proc. Natl. Acad. Sci. USA* 81: 6851-6855). For example, variable domains are obtained from an antibody from an experimental animal (the "parental antibody"), such as a mouse, and the constant domain sequences are obtained from human antibodies, so that the resulting chimeric antibody will be less likely to elicit an adverse immune response in a human subject than the parental mouse antibody.

A recombinant antibody or antigen-binding fragment thereof of the invention is, in an embodiment of the invention, an antibody which is produced recombinantly, e.g., expressed from a polynucleotide which has been introduced into an organism (e.g., a plasmid containing a polynucleotide encoding the antibody or fragment transformed into a bacterial cell (e.g., *E. coli*) or a mammalian cell (e.g., CHO cell)), followed by isolation of the antibody or fragment from the organism.

The present invention comprises methods for expressing any antibody or antigen-binding fragment thereof or polypeptide of the present invention. For example, an embodiment of the present invention comprises a process for producing an immunoglobulin molecule or an immunologically functional immunoglobulin fragment comprising at least the variable domains of the immunoglobulin heavy and/or light chains, in a host cell (e.g., a single host cell), such as a CHO cell (e.g., CHO-K1 or DXB311 cell), comprising the steps of (i) transforming said host cell with a first polynucleotide encoding at least the variable domain of the immunoglobulin heavy chain and a second polynucleotide encoding at least the variable domain of the immunoglobulin light chain, and (ii) independently expressing said first polynucleotide and said second polynucleotide so that said immunoglobulin heavy and light chains are produced as separate molecules in said transformed host cell. In an embodiment of the invention, the polynucleotides are operably linked to a promoter such as a CMV promoter. The present invention also comprises a process for producing an immunoglobulin molecule or an immunologically functional immunoglobulin fragment comprising introducing transforming a first haploid yeast host cell (e.g., *Pichia* such as *Pichia pastoris*) with a first polynucleotide encoding at least the variable domain of the immunoglobulin heavy chain or light chain and transforming a second haploid yeast host cell (e.g., *Pichia* such as *Pichia pastoris*) with a second polynucleotide encoding the other chain, allowing the haploid cells to form polyploids, such as diploids, (e.g., via mating), selecting the polyploids from the haploids, and growing the polyploids under conditions wherein the heavy and light chains are expressed in the polyploids and, optionally, secreted into the culture medium.

In an embodiment of the invention, polynucleotides introduced into a host cell remain ectopic whereas in another embodiment of the invention, the polynucleotide is integrated into the chromosomal DNA of the host cell.

In an embodiment of the invention, a method for producing an antibody or fragment further comprises isolating the chains that are expressed from the host cell and/or culture medium.

The present invention also includes camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079, which are hereby incorporated by reference in their entireties). Camelidae (camels, dromedaries and llamas) comprise IgG antibodies in which are devoid of light chains and therefore called 'heavy-chain' IgGs or HCAb (for heavy-chain antibody). HCAbs typically have a molecular weight of ~95 kDa since they consist only of the heavy-chain variable domains. Although the HCAbs are devoid of light chains, they have an authentic antigen-binding repertoire (Hamers-Casterman et al., Nature (1993) 363:446-448; Nguyen et al., Adv. Immunol. (2001) 79:261-296; Nguyen et al., Immunogenetics. (2002) 54:39-47). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from both human and non-human (e.g., mouse or rat) antibodies. In general, the humanized antibody will comprise substantially all of at least one, and typically two, variable domains, in which all or substantially all of the hypervariable loops (CDRs) correspond to those of a non-human immunoglobulin, and all or substantially all of the framework (FR) regions are those of a human immunoglobulin sequence. An immunoglobulin light or heavy chain variable region consists of a "framework" region interrupted by three hypervariable regions, also called CDRs. Several public sources for human framework sequence are available including, e.g., V-base (MRC Center for Protein Engineering). The humanized antibody may optionally comprise at least a portion of a human immunoglobulin constant region (Fc). For example, an embodiment of the invention includes humanized anti-PCSK9 (e.g., anti-human PCSK9) antibodies comprising the specific mouse immunoglobulin CDRs and human immunoglobulin framework regions which are set forth herein, e.g., fused to a human immunoglobulin constant region. The following U.S. patents are herein incorporated by reference: U.S Pat. Nos. 5,585,089, 5,693,761, 5,693,762 and 6,180,370. For example, embodiments of the invention include those wherein any of the following groups of CDRs are included within a humanized antibody of the invention:

(i) HCDR1 comprising the amino acid sequence G F N I K D T Y M H (SEQ ID NO: 11), HCDR2 comprising the amino acid sequence R I D P A N G H T E Y D P K S Q D (SEC) ID NO: 12) and HCDR3 comprising the amino acid sequence s Y F G S I F A Y (SEQ ID NO: 13);

(ii) HCDR1 comprising the amino acid sequence G F N I K D T Y I H (SEQ ID NO: 19), HCDR2 comprising the amino acid sequence R I D P A N G H T E Y D P K F Q G (SEC) ID NO: 20) and HCDR3 comprising the amino acid sequence S Y Y G S I F A Y (SEQ ID NO: 21);

(iii) HCDR1 comprising the amino acid sequence G F N I K D Y Y I H (SEQ ID NO: 27), HCDR2 comprising the amino acid sequence W I D P E N G D T E Y A P K F Q G (SEC) ID NO: 28) and HCDR3 comprising the amino acid sequence Y Y R Y D D G T W F P Y (SEQ ID NO: 29);

(iv) HCDR1 comprising the amino acid sequence G F N I K D T Y I H (SEQ ID NO: 35), HCDR2 comprising the amino acid sequence W I D P A N G Y T K Y A P N F Q G (SEQ ID NO: 36) and HCDR3 comprising the amino acid sequence G Y Y R Y Y S L D Y (SEQ ID NO: 37);

(v) HCDR1 comprising the amino acid sequence G F T F S N H D M A (SEQ ID NO: 43), HCDR2 comprising the amino acid sequence S I T P S G G T T Y Y R D S V E G (SEQ ID NO: 44) and HCDR3 comprising the amino acid sequence Q N Y Y D G S Y Y G L Y Y F D Y (SEQ ID NO: 45);

(vi) HCDR1 comprising the amino acid sequence G Y T F T D Y Y M N (SEQ ID NO: 51), HCDR2 comprising the amino acid Sequence D I N P N N G G A I Y N Q K F K G (SEQ ID NO: 52) and HCDR3 comprising the amino acid sequence G I I T E I A E D F (SEQ ID NO: 53);

(vii) LCDR1 comprising the amino acid sequence S A S S S V S Y L Y (SEQ ID NO: 15), LCDR2 comprising the amino acid sequence R S S H R A S (SEQ ID NO: 16) and LCDR3 comprising the amino acid sequence H Q Y Q S Y P P T (SEQ ID NO: 17);

(viii) LCDR1 comprising the amino acid sequence S A S S S V S Y L F (SEQ ID NO: 23), LCDR2 comprising the amino acid sequence R T S Y L A S (SEQ ID NO: 24) and LCDR3 comprising the amino acid sequence H Q Y H T Y P P T (SEQ ID NO: 25);

(ix) LCDR1 comprising the amino acid sequence R A S G N I H S Y L A (SEQ ID NO: 31), LCDR2 comprising the amino acid sequence N A K T L P D (SEQ ID NO: 32) and LCDR3 comprising the amino acid sequence Q H F W N T P W T (SEQ ID NO: 33);

(x) LCDR1 comprising the amino acid sequence R A S Q D I S N Y L N (SEQ ID NO: 39), LCDR2 comprising the amino acid sequence Y S S R L H S (SEQ ID NO: 40) and LCDR3 comprising the amino acid sequence Q Q G K T L P L T (SEQ ID NO: 41);

(xi) LCDR1 comprising the amino acid sequence R S S Q S L V Y S D G N T Y L H (SEQ ID NO: 47), LCDR2 comprising the amino acid sequence R V S N K F S (SEQ ID NO: 48) and LCDR3 comprising the amino acid sequence L Q S T H F P P T (SEQ ID NO: 49); or (xii) LCDR1 comprising the amino acid sequence K A S Q N V G T N V V (SEQ ID NO: 55), LCDR2 comprising the amino acid sequence S A S Y R Y S (SEQ ID NO: 56) and LCDR3 comprising the amino acid sequence Q Q Y K T Y P Y T (SEQ ID NO: 57).

The present invention also includes isolated polypeptides comprising the amino acid sequences of the immunoglobulin chains set forth herein along with isolated polynucleotides encoding said polypeptides, vectors comprising the polynucleotides and isolated host cells comprising the polynucleotides and vectors (e.g., CHO cells, bacterial cells such as *E. coli* and fungal cells such as *S. cerevisiae* and *Pichia* such as *Pichia pastoris*). Methods for making the polypeptides are also included: comprising introducing a polynucleotide or vector into a host cell and culturing the host cell under condition whereby the polypeptide can be expressed and, optionally, secreted and, optionally, isolating the polypeptide.

Therapeutic Methods, Administration and Pharmaceutical Formulations

The present invention provides methods for treating or preventing disorders of cholesterol or lipid homeostasis and disorders associated therewith, e.g., hypercholesterolemia, hyperlipidemia, hypertriglyceridaemia, sitosterolemia, atherosclerosis, arteriosclerosis, coronary heart disease, vascular inflammation and xanthoma by administering a therapeutically effective amount of an anti-PCSK9 antibody (e.g., as set forth herein) or antigen-binding fragment thereof or an EGF-A polypeptide.

The term hypercholesterolemia includes, e.g., familial and non-familial hypercholesterolemia. Familial hypercholesterolemia (FRC) is an autosomal dominant disorder characterized by elevation of serum cholesterol bound to low density lipoprotein (LDL). Familial hypercholesterolemia includes both heterozygous FHC and homozygous FHC.

Hyperlipidemia is an elevation of lipids in the bloodstream. These lipids include cholesterol, cholesterol esters, phospholipids and triglycerides. Hyperlipidemia includes for example, type I, IIa, IIb, III, IV and V.

Sitosterolemia is a rare inherited plant sterol storage disease. In general, the metabolic defect in the affected patient causes hyperabsorption of sitosterol from the gastrointestinal tract, decreased hepatic secretion of sitosterol with subsequent decreased elimination, and altered cholesterol synthesis.

Atherosclerosis includes hardening of arteries associated with deposition of fatty substances, cholesterol, cellular waste products, calcium and fibrin in the inner lining of an artery. The buildup that results is called plaque.

Arteriosclerosis includes the diffuse build-up and deposition of calcium in artery walls which leads to hardening.

The present invention also provides methods for improving blood cholesterol markers associated with increased risk of heart disease. These markers include high total cholesterol, high LDL, high total cholesterol to HDL ratio and high LDL to HDL ratio.

In general, a total cholesterol of less than 200 mg/dL is considered desirable, 200-239 mg/dL is considered borderline high and 240 mg/dL and above is considered high.

In general, a blood LDL level of less than 100 mg/dL is considered optimal; 100-129 mg/dL is considered near optimal/above optimal, 130-159 mg/dL is considered borderline high, 160-189 mg/dL is considered high and 190 mg/dL and above is considered very high.

In general, HDL levels considered normal are at least 35-40 mg/dL.

Another indicator of heart disease risk is the ratio of total cholesterol to HDL. In general, a very low risk of heart disease correlates with a ratio of <3.4 (men) or <3.3 (women); a low risk is associated with a ratio of 4.0 (men) or 3.8 (women), an average risk is associated with a ratio of 5.0 (men) or 4.5 (women), a moderate risk is associated with a ratio of 9.5 (men) or 7.0 (women) and a high risk is associated with a ratio of >23 (men) or >11 (women).

A further indicator of heart disease risk is the ratio of LDL to HDL. In general, a very low risk is associated with a ratio of 1 (men) or 1.5 (women), an average risk is associated with a ratio of 3.6 (men) or 3.2 (women), a moderate risk is associated with a ratio of 6.3 (men) or 5.0 (women) and a high risk is associated with a ratio of 8 (men) or 6.1 (women).

In an embodiment of the invention, anti-PCSK9 antibodies and antigen-binding fragments thereof or EGF-A polypeptides of the invention are formulated into a pharmaceutical formulation which comprises a pharmaceutically acceptable carrier. For general information concerning formulations, see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York, Kenneth A. Walters (ed.) (2002) *Dermatological and Transdermal Formulations (Drugs and the Pharmaceutical Sciences).* Vol 119, Marcel Dekker.

The anti-PCSK9 antibodies and antigen-binding fragments thereof or EGF-A polypeptides of the present invention can be formulated according to known methods to prepare pharmaceutically useful compositions, whereby the antibody or fragment is combined in admixture with a pharmaceutically acceptable carrier. Carriers, excipients or stabilizers are nontoxic to recipients at the dosages and concentrations employed, and include buffers such as phosphate, citrate and other organic acids; antioxidants including ascorbic acid; low molecular weight polypeptides: proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or PEG. The formulations to be used for in vivo administration must be sterile. This is readily accomplished by filtration through sterile filtration membranes, prior to or following lyophilization and reconstitution. Therapeutic or pharmaceutical compositions or formulations herein generally are placed into a container having a sterile access port, for example, an intravenous solution bag or vial having a stopper pierceable by a hypodermic injection needle.

The route of administration of the antibodies and antigen-binding fragments thereof of the invention are, in an embodiment of the invention, by a parenteral route (e.g., intravenous, subcutaneous, intraarterial, intratumoral, intramuscular, intraperitoneal).

Dosages and desired anti-PCSK9 or EGF-A polypeptide concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42 96.

When used to treat a disorder in a subject (e.g., as discussed herein), a therapeutically effective dosage or amount of anti-PCSK9 antibody or antigen-binding fragment thereof or EGF-A polypeptides is administered to the subject. In an embodiment of the invention, a therapeutically effective dosage is a dosage sufficient to decrease total serum cholesterol, decrease blood LDL levels or increase blood HDL levels to any degree whatsoever. In an embodiment of the invention, a therapeutically effective dosage of anti-PCSK9 antibody or antigen-binding fragment thereof (e.g., as set forth herein) for treatment of hypercholesterolemia, hyperlipidemia, hyper-triglyceridaemia, sitosterolemla, atherosclerosis, arteriosclerosis, coronary heart disease, vascular inflammation or xanthoma or for treatment of any blood marker of heart disease risk (e.g., as discussed herein) is about 0.1 mg/kg (body weight)/week to about 1.0 mg/kg/week. A therapeutically effective dosage of soluble PCSK9 EGF-A polypeptide is, in an embodiment of the invention, about 0.25 mg/kg/week to about 25 mg/kg/week, When possible, administration and dosage of an agent (e.g., further therapeutic agents discussed herein) is done according to the schedule listed in the product information sheet of the agents, in the *Physicians' Desk Reference* 2003 (*Physicians' Desk Reference*, 57th Ed); Medical Economics Company; ISBN: 1563634457; 57th edition (November 2002), as well as therapeutic protocols well known in the art.

A physician or clinician may monitor the blood cholesterol levels in a subject being treated or about to be treated with an anti-PCSK9 antibody or antigen-binding fragment thereof or EGF-A polypeptide and make adjustments to the subject's treatment regimen as needed to reach a positive medical outcome.

Further Chemotherapeutic Agents

The present invention provides methods and compositions for treating disorders of lipid and cholesterol metabolism (e.g., any set forth herein) by administration of an anti-PCSK9 antibody or antigen-binding fragment thereof or EGF-A polypeptide. The antibodies may, in an embodiment of the invention, be provided or administered in association with any additional or further chemotherapeutic agent. In an embodiment of the invention, the further chemotherapeutic agent is a cardiovascular agent, an adrenergic blocker, an antihypertensive agent, an angiotensin system inhibitor, an angiotensin-converting enzyme (ACE) inhibitor, a coronary vasodilator, a diuretic or an adrenergic stimulant. In an embodiment of the invention, the further therapeutic agent is a cholesterol lowering medication such as an HMG-CoA reductase inhibitor.

Cardiovascular agents which may used in connection with the present invention include those for treatment or prevention of lipid and/or cholesterol disorders or hypertension and other cardiovascular disorders and diseases. Disorders of lipid or cholesterol metabolism may be caused or aggravated by hypertension. Hypertension is defined as persistently high blood pressure. Generally, adults are classified as being hypertensive when systolic blood pressure is persistently above 140 mmHg or when diastolic blood pressure is above 90 mmHg. Long-term risks for cardiovascular mortality increase in a direct relationship with persistent blood pressure. Examples of antihypertensive agents which may be used in the present invention include e.g., calcium channel blockers, angiotensin-converting enzyme (ACE) inhibitors, angiotensin-II receptor antagonists, diuretics, adrenergic blockers including beta-adrenergic receptor blockers and alpha-adrenergic receptor blockers or diuretics, Other cardiac drugs that may be provided in association with an anti-PCSK9 antibody or antigen-binding fragment thereof includes anti-anginal agents, such as adrenergic stimulants or coronary vasodilators and HMG-CoA reductase inhibitors.

HMG-CoA reductase inhibitors inhibit the HMG-CoA reductase enzyme and, thus, reduce production of cholesterol in the body of a subject. HMG-CoA reductase inhibitors include, e.g., lovastatin, atorvastatin, pravastatin, rosuvastatin, fluvastatin, rivastatin and simvastatin

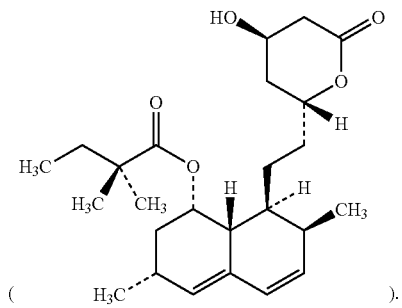

Adrenergic blockers include those compounds which are β-receptor inhibitors and/or α-receptor inhibitors, Adrenergic blockers which are β-receptor inhibitors include a class of drugs that antagonize the cardiovascular effects of catecholamines in hypertension, angina pectoris, and cardiac arrhythmias. β-adrenergic receptor blockers include, but are not limited to, bunolol hydrochloride (1(2H)-Naphthalenone, 5-[3-(1,1-dimethylethyl)amino]-2-hydroxypropoxy]-3,4-dihydro-, hydrochloride, CAS RN 31969-05-8 which can be obtained from Parke-Davis); acebutolol (±N-[3-Acetyl-4-[2-hydroxy-3-[(1 methylethyl)amino]propoxy]phenyl]-butanamide, or (±)-3'-Acetyl-4'-[2-hydroxy-3-(isopropylamino) propoxy]butyranilide); acebutolol hydrochloride (such as N-[3-acetyl-4-[2-hydroxy-3-[1-methyl-ethyl)amino]propoxy]phenyl]-, monohydrochloride, (±-;-3'-Acetyl-4'-[2-hydroxy-3-(isopropylamino)propoxy]butyranilide monohydrochloride, for example, SECTRAL® Capsules available from Wyeth-Ayerst); alprenolol hydrochloride (2-Propanol, 1-[(1-methylethyl)amino]-3-[2-(2-propenyl)phenoxy]-, hydrochloride, CAS RN 13707-88-5 see Netherlands Patent Application No. 6,605,692); atenolol (such as benzeneacetamide 4-[2'-hydroxy-3'-[(1-methylethyl)amino]propoxy]-, for example, TENORMIN® I.V. Injection available from AstraZeneca); carteolol hydrochloride (such as 5-[3-[(1,1-dimethylethyl)amino]-2-hydroxypropoxy]-3,4-dihydro-2(1H)-quinolinone monohydrochloride, for example, Cartrol® Filmtab® Tablets available from Abbott); Celiprolol hydrochloride (3-[3-Acetyl-4-[3-(tert-butylamino)-2-hydroxypropoxyl]phenyl]-1,1-diethylurea monohydrochloride, CAS RN 57470-78-7, also see in U.S. Pat. No. 4,034,009); cetamolol hydrochloride (Acetamide, 2-[2-[3-[(1,1-dimethylethyl) amino]-2-hydroxypropoxy]-phenoxy]-N-methyl-, monohydrochloride, CAS RN 77590-95-5, see also U.S. Pat. No. 4,059,622); labetalol hydrochloride (such as 5-[1-hydroxy-2-[(1-methyl-3-phenylpropyl)amino]ethyl]salicylamide monohydrochloride, for example, NORMODYNE® Tablets available from Schering; esmolol hydrochloride ((±)-Methyl p-[2-hydroxy-3-(isopropylamino)propoxy]hydrocinnamate hydrochloride, for example, BREVIBLOC® Injection available from Baxter); levobetaxolol hydrochloride (such as (S)-1-[p-[2-(cyclopropylmethoxy)ethyl]phenoxy]-3-(isopropylamino)-2-propanol hydrochloride, for example, BETAXON™ Ophthalmic Suspension available from Alcon); levobunolol hydrochloride (such as (−)-5-[3-(tert-Butylamino)-2-hydroxypropoxy]-3,4-dihydro-1(2H)-naphthalenone hydrochloride, for example, BETAGAN® Liquifilm® with C CAP® Compliance Cap available from Allergan); nadolol (such as 1-(tert-butylamino)-3-[(5,6,7,8-tetrahydro-cis-6,7-dihydroxy-1-naphthypoxy]-2-propanol, for example, Nadolol Tablets available from Mylan); practolol (Acetamide, N-[4-[2-hydroxy-3-[1-methylethyl) amino]-propoxy]phenyl]-, CAS RN 6673-35-4, see also U.S. Pat. No. 3,408,387); propranolol hydrochloride (1-(isopropylamino)-3-(1-naphthyloxy)-2-propanol hydrochloride CAS RN 318-98-9); sotalol hydrochloride (such as d,l-N-[4-[1-hydroxy-2-[(1-methylethyl)amino]ethyl]-phenyl]methanesulfonamide monohydrochloride, for example, BETAPACE AF™ Tablets available from Berlex); timoloi (2-Propanol, 1-[(1,1-dimethylethyl)amino]-3-[[4-4(4-morpholinyl)-1,2, 5-thiadiazol-3-yl]oxy]-, hemihydrate, (S)-CAS RN 91524-16-2); timolol maleate (S)-1-[(1,1-dimethylethyl)amino]-3-[[4-(4-morpholinyl)-1,2,5-thiadiazol-3-yl]oxy]-2-propanol (Z)-2-butenedioate (1:1) salt, CAS RN 26921-17-5); bisoprolol (2-Propanol, 1-[4-[[2-(1-methylethoxy)ethoxy]-methyl]phenoxyl]-3-[(1-methylethyl)amino]-, (±), CAS RN 66722-44-9); bisoprolol fumarate (such as (±)-1-[4-[[2-(1-Methylethoxy)ethoxy]methyl]phenoxy]-3-[(1-methylethyl) amino]-2-propanol (E)-2-butenedioate (2:1) (salt), for example, ZEBETA™ Tablets available from Lederle Consumer); nebivalol (2H-1-Benzopyran-2-methanol, αα'-[iminobis(methylene)]bis[6-fluoro-3,4-dihydro-, CAS RN 99200-09-6 see also U.S. Pat. No. 4,654,362); cicloprolol hydrochloride, such 2-Propanol, 1-[4-[2-(cyclopropylmethoxy)ethoxy]phenoxy)-3-[1-methylethyl)amino]-, hydrochloride, A.A.S. RN 63686-79-3); and dexpropranolol hydrochloride (2-Propanol, 1-[1-methylethyl)-amino]-3-(1-naphthalenyloxy)-hydrochloride (CAS RN 13071-11-9); diacetolol hydrochloride (Acetamide, N-[3-acetyl-4-[2-hydroxy-3-[(1-methyl-ethyl)amino]propoxy][phenyl]-, monohydrochloride CAS RN 69796-04-9); dilevalol hydrochloride (Benzamide, 2-hydroxy-5-[1-hydroxy-2-[1-methyl-3-phenylpropyl)amino]ethyl]-, monohydrochloride, CAS RN 75659-08-4); exaprolol hydrochloride (2-Propanol, 1-(2-cyclohexylphenoxy)-3-[(1-methylethyl)amino]-, hydrochloride CAS RN 59333-90-3); flestolol sulfate (Benzoic acid, 2-fluoro-, 3-[[2-[aminocarbonyl)amino]-1-dimethylethyl] amino]-2-hydroxypropyl ester, (±)-sulfate (1:1) (salt), CAS RN 88844-73-9; metaiol hydrochloride (Methanesulfonamide, N-[4-[1-hydroxy-2-(methylamino)propyl]phenyl]-, monohydrochloride CAS RN 7701-65-7); metoprolol 2-Propanol, 1-[4-(2-methoxyethyl)phenoxy]-3-[1-methylethyl) amino]-; CAS RN 37350-58-6); metoprolol tartrate (such as 2-Propanol, 1-[4-(2-methoxyethyl)phenoxy]-3-[(1-methylethyl)amino]-, for example, LOPRESSOR® available from Novartis); pamatolol sulfate (Carbamic acid, [2-[4-[2-hydroxy-3-[(1-methylethyl)amino]propoxyl]phenyl]-ethyl]-, methyl ester, (±) sulfate (salt) (2:1), CAS RN 59954-01-7); penbutolol sulfate (2-Propanol, 1-(2-cyclopentylphenoxy)-3-[1,1-dimethylethyl)amino]1, (S)-, sulfate (2:1) (salt), CAS RN 38363-32-5); practolol (Acetamide, N-[4-[2-hydroxy-3-[(1-methylethyl)amino]-propoxy]phenyl]-, CAS RN 6673-35-4;) tiprenolol hydrochloride (Propanol, 1-[(1-methylethyl)amino]-3-[2-(methylthio)-phenoxy]-, hydrochloride, (±), CAS RN 39832-43-4); tolamolol (Benzamide, 4-[2-[[2-hydroxy-3-(2-methylphenoxy)-propyl]amino]ethoxyl]-, CAS RN 38103-61-6).

Adrenergic receptors which are α-receptor inhibitors act to block vasoconstriction induced by endogenous catecholamines. The resulting fall in peripheral resistance leads to a fall in mean blood pressure. The magnitude of this effect is dependent upon the degree of sympathetic tone at the time the antagonist is administered.

Suitable adrenergic receptors which are α-receptor inhibitors include, but are not limited to, fenspiride hydrochloride (which may be prepared as disclosed in U.S. Pat. No. 3,399, 192 herein incorporated by reference); proroxan (GAS RN 33743-96-3); alfuzosin hydrochloride (CAS RN: 81403-68-1); and labetalol hydrochloride as described above or combinations thereof.

Adrenergic blockers with α and β receptor inhibitor activity which may be used with the present invention include, but are not limited to, bretylium tosylate (CAS RN: 61-75-6); dihydroergtamine mesylate (such as ergotaman-3,6',18-trione,9,-10-dihydro-12'-hydroxy-2'-methyl-5'-(phenylmethyl)-, (5'(alpha))-, monomethanesulfonate, for example, DHE 45® Injection available from Novartis); carvedilol (such as (±)-1-(Carbazol-4-yloxy)-3-[[2-(o-methoxyphenoxy)ethyl]amino]-2-propanol, for example, COREG® Tablets available from SmithKline Beecham); labetalol (such as 5-[1-hydroxy-2-[(1-methyl-3-phenylpropyl)amino]ethyl] salicylamide monohydrochloride, for example, NORMODYNE® Tablets available from Schering); bretylium tosylate (Benzenemethanaminium, 2-bromo-N-ethyl-N,N-dimethyl-, salt with 4-methylbenzenesulfonic acid (1:1) CAS RN 61-75-6); phentolamine mesylate (Phenol, 3-[[(4,5-dihydro-1H-imidazol-2-yl)methyl](4-methylphenyl)amino]-, monomethanesulfonate (salt) CAS RN 65-28-1); solypertine tartrate (5H-1,3-Dioxolo[4,5-f]indole, 7-[2-[4-(2-methoxyphenyl)-1-piperazinyl]ethyl]-, (2R,3R)-2,3-dihydroxybutanedioate (1:1) CAS RN 5591-43-5); zolertine hydrochloride (Piperazine, 1-phenyl-4-[2-(1H-tetrazol-5-yl)ethyl]-, monohydrochloride (8Cl, 9Cl) CAS RN 7241-94-3)

An angiotensin system inhibitor is an agent that interferes with the function, synthesis or catabolism of angiotensin II. These agents which may be used in the present invention include but are not limited to angiotensin-converting enzyme (ACE) inhibitors, angiotensin II antagonists, angiotensin II receptor antagonists, agents that activate the catabolism of angiotensin II and agents that prevent the synthesis of angiotensin I from which angiotensin II is ultimately derived. The renin-angiotensin system is involved in the regulation of hemodynamics and water and electrolyte balance. Factors that lower blood volume, renal profusion, or the concentration of Na+ in plasma tend to activate the system, while factors that increase these parameters tend to suppress its function. Angiotensin I and angiotensin flare synthesized by the enzymatic renin-angiotensin pathway. The synthetic process is initiated when the enzyme renin acts on angiotensinogen, a pseudoglobulin in blood plasma, to produce the cecapeptide angiotensin I. Angiotensin I is converted by angiotensin-converting enzyme (ACE) to angiotensin II. The latter is an active pressor substance which has been implicated as a causative agent in several forms of hypertension in various mammalian species.

Angiotensin II receptor antagonists are compounds which interfere with the activity of angiotensin II by binding to angiotensin it receptors and interfering with its activity, Angiotensin II receptor antagonists which may be used in the present invention are well known and include peptide compounds and non-peptide compounds, Non-limiting examples of angiotensin II receptor antagonists include: candesartan cilexetil (1H-Benzimidazole-7-carboxylic acid, 2-ethoxy-1-[[2'-(1H-tetrazol-5-yl)[1,1'-biphenyl]-4-yl]methyl]-, 1-[[(cyclohexyloxy)carbonyl]oxy]ethyl ester) CAS RN 145040-37-5); telmisartan([1,1'-Biphenyl]-2-carboxylic acid, 4'-[(1,4'-dimethyl-2'-propyl[2,6-bi-1H-benzimidazol]-[1'-yl)methyl]-CAS RN 144701-48-4); candesartan (1H-Benzimidazole-7-carboxylic acid, 2-ethoxy-1-[[2'-(1H-tetrazol-5-yl)[1,1'-biphenyl]-4-yl]methyl]-CAS RN 139481-59-7); losartan potassium (1H-Imidazole-5-methanol, 2-butyl-4-chloro-1-[[2'-(1H-tetrazol-5-yl)[1,1'-biphenyl]-4-yl]methyl]-, monopotassium Irbesartan 1,3-Diazaspiro[4.4]non-1-en-4-one, 2-butyl-3-[[2'-(1H-tetrazol-5-yl)[1,1'-biphenyl]-4-yl]methyl]-CAS RN 138402-11-6).

Angiotensin-converting enzyme (ACE), is an enzyme which catalyzes the conversion of angiotensin I to angiotensin II. ACE inhibitors which may be used in the present invention include amino acids and derivatives thereof, peptides, including di and tri peptides and antibodies to ACE which intervene renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Suitable ACE inhibitors include, but are not limited to, benazepril hydrochloride (such as 3-[[1-(ethoxycarbonyl)-3-phenyl-(1S)-propyl] amino]-2,3,4,5-tetrahydro-2-oxo-1 H-1-(3S)-benzazepine-1-acetic acid monohydrochloride, for example, LOTREL® Capsules available from Novartis); captopril (such as 1-[(2S)-3-mercapto-2-methylpropionyl]-L-proline, for example, CAPTOPRIL Tablets available from Mylan); fosinopril (such as L-proline, 4-cyclohexyl-1-[[[2-methyl-1-(1-oxopropoxy)propoxy](4-phenylbutyl)phosphinyl]acetyl]-, sodium salt, trans-., for example, MONOPRIL® Tablets available from Bristol-Myers Squibb); moexipril hydrochloride (such as [3S-[2[R*(R*)],3R*]]-2-[2-[[1-(Ethoxycarbonyl)-3-phenylpropyl]amino]-1-oxopropyl]-1,2,3,4-tetrahydro-6,7-dimethoxy-3-isoquinolinecarboxylic acid, monohydrochloride, for example, UNIRETIC® Tablets available from Schwarz); perindopril erbumine (such as 2S,3aS,7aS)-1-[(S)—N—[(S)-1-Carboxybutyl]alanyl]hexahydro-2-indolinecarboxylic acid, 1-ethyl ester, compound with tert-butylamine (1:1), for example, ACEON® Tablets available from Solvay); quinapril (such as [3S-[2[R*(R*)],3R*]]-2-[2-[[1-(ethoxycarbonyl)-3-phenylpropyl]amino]-1-oxopropyl]-1,2,3,4-tetrahydro-3-isoquinolinecarboxylic acid, monohydrochloride, for example, ACCURETIC® Tablets available from Parke-Davis); ramipril (such as 2-aza-bicyclo[3.3.0]-octane-3-carboxylic acid derivative, for example, ALTACE® Capsules available from Monarch); enalapril maleate (such as (S)-1-[N-[1-(ethoxycarbonyl)-3-phenylpropyl]-L-alanyl]-L-proline, (Z)-2-butertedioate salt (1:1), for example, VASOTEC® Tablets available from Merck); lisinopril (such as (S)-1-[N 2-(1-carboxy-3-phenylpropyl)-L-lysyl]-L-proline dihydrate, for example, PRINZIDE® Tablets available from Merck); delapril (which may be prepared as disclosed in U.S. Pat. No. 4,385,051); and spirapril (which may be prepared as disclosed in U.S. Pat. No. 4,470,972); benazeprilat (1H-1-Benzazepine-1-acetic acid, 3-[[(1S)-1-carboxy-3-phenylpropyl]amino]-2,3,4,5-tetrahydro-2-oxo-, (3S)-CAS RN 86541-78-8); delapril hydrochloride (Glycine, N-[(1S)-1-(ethoxycarbonyl)-3-phenylpropyl]-L-alanyl-N-(2,3-dihydro-1H-inden-2-yl)-, monohydrochloride CAS RN 83435-67-0); fosinopril sodium (L-Proline, 4-cyclohexyl-1-[[R(R)-[(1S)-2-methyl-1-(1-oxopropoxy)propoxy](4-phenylbutyl)phosphinyl]acetyl]-, sodium salt, (4S)-CAS RN 88889-14-9); libenzapril (1H-1-Benzazepine-1-acetic acid, 3-[[(1S)-5-amino-1-carboxypentyl]amino]-2,3,4,5-tetrahydro-2-oxo-, (3S)-CAS RN 109214-55-3); pentopril (1H-Indole-1-pentanoic acid, 2-carboxy-2,3-dihydro-.alpha., .gamma.-dim ethyl-.delta.-oxo-, .alpha.-ethyl ester, (.alpha.R, .gamma.R,2S)-CAS RN 82924-03-6); perindopril 1H-Indole-2-carboxylic acid, 1-[(2S)-2-[[(1S)-1-(ethoxycarbonyl]butyliamino]-1-oxopropyl]octahydro-, (2S,3aS,7aS)-CAS RN 82834-16-0); quinapril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-, monohydrochloride, (3S)-CAS RN 82586-55-); quinaprilat (3-Isoquinolinecarboxylic acid, 2-[(2S)-2-[[(1S)-1-carboxy-3-phenylpropyl]amino]-1-oxopropyl]-1,2,3,4-tetrahydro-, (3S)-CAS RN 82768-85-2); spirapril hydrochloride (1,4-Dithia-7-azaspiro[4.4]nonane-8-carboxylic acid, 7-[(2S)-2-[[(1S)-1-(ethoxycarbonyl)-3-phenylpropyl]amino]-1-oxopropyl]-, monohydrochloride, (8S)-CAS RN 94841-17-5); spiraprilat 1(4-Dithia-7-azaspiro[4.4]nonane-8-carboxylic acid, 7-[(2S)-2-[[(1S)-1-carboxy-3-phenylpropyl]amino]-1-oxopropyl]-, (8S)-CAS RN 83602-05-5); teprotide (Bradykinin potentiator BPP9a CAS RN 35115-60-7); lisinopril (L-Proline, N2-[(1S)-1-carboxy-3-phenylpropyl]-L-lysyl-CAS RN 76547-98-3); zofenopril (L-Proline, 1-[(2S)-3-(benzoylthio)-2-methyl-1-oxopropyl]-4-(phenylthio)-, calcium salt (2:1), (4S)-CAS RN 81938-43-4).

"Calcium channel blockers" are a chemically diverse class of compounds having important therapeutic value in the control of a variety of diseases including several cardiovascular disorders such as hypertension, angina, and cardiac arrhythmias (Fleckenstein, *Cir. Res. V.* 52 (suppl. 1), p. 13-16 (1983); Fleckenstein, *Experimental Facts and Therapeutic Prospects*, John Wiley, New York (1983); McCall, D., *Curr. Pract Cardiol.*, v. 10, p. 1-11 (1985)). Calcium channel blockers are a heterogeneous group of drugs that prevent or slow the entry of calcium into cells by regulating cellular calcium channels (Remington, *The Science and Practice of Pharmacy*, Nineteenth Edition, Mack Publishing Company, Eaton, Pa., p. 963 (1995)). Calcium channel blockers useful in the present invention include but are not limited to, the besylate salt of amlodipine (such as 3-ethyl-5-methyl-2-(2-aminoethoxymethyl)-4-(2-chlorophenyl)-1,4-dihydro-6-methyl-3,5-pyridinedicarboxylate benzenesulphonate, for example, NORVASC® available from Pfizer); clentiazem maleate (1,5-Benzothiazepin-4(5H)-one, 3-(acetyloxy)-8-chloro-5-[2-(dimethylamino)ethyl]-2,3-dihydro-2-(4-methoxyphenyl)-(2S-cis)-, (Z)-2-butenedioate (1:1), see also U.S. Pat. No. 4,567,195); isradipine (3,5-Pyridinedicarboxylic acid, 4-(4-benzofurazanyl)-1,4-dihydro-2,6-dimethyl-, methyl 1-methylethyl ester, (±)-4(4-benzofurazanyl)-1,4-dihydro-2,6-dimethyl-3,5-pyridinedicarboxylate, see also U.S. Pat. No. 4,466,972); nimodipine (such as is isopropyl (2-methoxyethyl) 1,4-dihydro-2,6-dimethyl-4-(3-nitrophenyl)-3,5-pyridinedicarboxylate, for example, NIMOTOP® available from Bayer); felodipine (such as ethyl methyl 4-(2,3-dichlorophenyl)-1,4-dihydro-2,6-dimethyl-3,5-pyridinedicarboxylate, for example, PLENDIL® Extended-Release Tablets available from AstraZeneca LP); nilvadipine (3,5-Pyridinedicarboxylic acid, 2-cyano-1,4-dihydro-6-methyl-4-(3-nitrophenyl)-, 3-methyl 5-(1-methylethyl)ester, also see U.S. Pat. No. 3,799,934); nifedipine (such as 3,5-pyridinedicarboxylic acid, 1,4-dihydro-2,6-dimethyl-4-(2-nitrophenyl)-, dimethyl ester, for example, PROCARDIA XL® Extended Release Tablets available from Pfizer); diltiazem hydrochloride (such as 1,5-Benzothiazepin-4(5H)-one, 3-(acetyloxy)-5[2-(dimethylamino)ethyl]-2,-3-dihydro-2(4-methoxyphenyl)-, monohydrochloride, (+)-cis., for example, TIAZAC® Capsules available from Forest); verapamil hydrochloride (such as benzeneacetonitrile, (alpha)-[[3-[[2-(3,4-dimethoxyphenyl)ethyl]methylamino]propyl]-3,4-dimethoxy-(alpha)-(1-methylethyl)hydrochloride, for example, ISOPTIN® SR Tablets available from Knoll Labs); teludipine hydrochloride (3,5-Pyridinedicarboxylic acid, 2-[(dimethylamino)methyl]-4-[2-[(1E)-3-(1,1-dimethylethoxy)-3-oxo-1-propenyl]phenyl]-1,4-dihydro-6-methyl-, diethyl ester, monohydrochloride) CAS RN 108700-03-4); belfosdil (Phosphonic acid, [2-(2-phenoxyethyl)-1,3-propanediyl]bis-, tetrabutyl ester CAS RN 103486-79-9); fostedil (Phosphonic acid, [[4-(2-benzothiazolyl)phenyl]methyl]-, diethyl ester CAS RN 75889-62-2).

Cardiovascular agents of the present invention which also act as "anti-anginal agents" are useful in the present invention. Angina includes those symptoms that occur when myocardial oxygen availability is insufficient to meet myocardial oxygen demand. Non-limiting examples of these agents include: ranolazine (hydrochloride1-piperazineacetamide, N-(2,6-dimethylphenyl)-4-[2-hydroxy-3-(2-methoxyphenoxy)propyl]-, dihydrochloride CAS RN 95635-56-6); betaxolol hydrochloride (2-Propanol, 1-[4-[2 (cyclopropylmethoxy)ethyl]phenoxy]-3-[(1-methylethyl)amino]-, hydrochloride CAS RN 63659-19-8); butoprozine hydrochloride (Methanone, [4-[3(dibutylamino)propoxy]phenyl](2-ethyl-3-indolizinyl)-, monohydrochloride CAS RN 62134-34-3); cinepazet maleate1-piperazineacetic acid, 4-[1-oxo-3-(3,4,5-trimethoxyphenyl)-2-propenyl]-, ethyl ester, (2Z)-2-butenedioate (1:1) CAS RN 50679-07-7); tosifen (Benzenesulfonamide, 4-methyl-N-[[[(1S)-1-methyl-2-phenylethyl]amino]carbonyl]-CAS RN 32295-18-4); verapamilhydrochloride (Benzeneacetonitrile, .alpha.[3-[[2-(3,4-dimethoxyphenyl)ethyl]methylamino]propyl]-3,4-dimethoxy-.alpha.-(1-methylethyl)-, monohydrochloride CAS RN 152-11-4); molsidomine (1,2,3-Oxadiazolium, 5-[(ethoxycarbonyl)amino]-3-(4-morpholinyl)-, inner salt CAS RN 25717-80-0); ranolazine hydrochloride (1-Piperazineacetamide, N-(2,6-dimethylphenyl)-4-[2-hydroxy-3-(2-methoxyphenoxy)propyl]-, dihydrochloride CAS RN 95635-56-6); tosifen (Benzenesulfonamide, 4-methyl-N-[[[(1S)-1-methyl-2-phenylethyl]amino]carbonyl]-CAS RN 32295-18-4).

"Coronary vasodilators" may act to reduce angina systems by increasing the oxygen supply to the heart. Coronary vasodilators useful in the present invention include, but are not limited to, diltiazem hydrochloride (such as 1,5-Benzothiazepin-4(5H)-one, 3-(acetyloxy)-5[2-(dimethylamino)ethyl]-2,-3-dihydro-2(4-methoxyphenyl)-, monohydrochloride, (+)-cis, for example, TIAZAC® Capsules available from Forest); isosorbide dinitrate (such as 1,4:3,6-dianhydro-D-glucitol 2,5-dinitrate, for example, ISORDIL® TITRADOSE® Tablets available from Wyeth-Ayerst); sosorbide mononitrate (such as 1,4:3,6-dianhydro-D-glucito,5-nitrate, an organic nitrate, for example, Ismo® Tablets available from Wyeth-Ayerst); nitroglycerin (such as 2,3 propanetriol trinitrate, for example, NITROSTAT® Tablets available from Parke-Davis); verapamil hydrochloride (such as benzeneacetonitrile, (±)-(alpha)[3[[2-(3,4 dimethoxyphenyl)ethyl]methylamino]propyl]-3,4-dimethoxy-(alpha)-(1-methylethyl) hydrochloride, for example, COVERA HS® Extended-Release Tablets available from Searle); chromonar (which may be prepared as disclosed in U.S. Pat. No. 3,282,938); clonitate (Annalen 1870 155); droprenilamine (which may be prepared as disclosed in German Patent No. 2,521,113); lidoflazine (which may be prepared as disclosed in U.S. Pat. No. 3,267,104); prenylamine (which may be prepared as disclosed in U.S. Pat. No. 3,152,173); propatyl nitrate (which may be prepared as disclosed in French Patent No. 1,103, 113); mioflazine hydrochloride (1-Piperazineacetamide, 3-(aminocarbonyl)-4-[4,4-bis(4-fluorophenyl)butyl]-N-(2, 6-dichlorophenyl)-, dihydrochloride CAS RN 83898-67-3); mixidine (Benzeneethanamine, 3,4-dimethoxy-N-(1-methyl-2-pyrrolidinylidene)-Pyrrolidine, 2-[(3,4-dimethoxyphenethyl)imino]-1-methyl-1-Methyl-2-[(3,4-dimethoxyphenethyl)imino]pyrrolidine CAS RN 27737-38-8); molsidomine (1,2,3-Oxadiazolium, 5-[(ethoxycarbonyl)amino]-3-(4-morpholinyl)-, inner salt CAS RN 25717-80-0); isosorbide mononitrate (D-Glucitol, 1,4:3,6-dianhydro-, 5-nitrate CAS RN 16051-77-7); erythrityl tetranitrate (1,2,3, 4-Butanetetrol, tetranitrate, (2R,3S)-rel-CAS RN 7297-25-8); clonitrate(1,2-Propanediol, 3-chloro-, dinitrate (7Cl, 8Cl, 9Cl) CAS RN 2612-33-1); dipyridamole Ethanol, 2,2',2",2'"-[(4,8-di-1-piperidinylpyrimido[5,4-d]pyrimidine-2,6-diyl) dinitrilo]tetrakis-CAS RN 58-32-2); nicorandil (CAS RN 65141-46-03-); pyridinecarboxamide (N-[2-(nitrooxy) ethyl]-Nisoldipine3,5-Pyridinedicarboxylic acid, 1,4-dihydro-2,6-dimethyl-4-(2-nitrophenyl)-, methyl 2-methylpropyl ester CAS RN 63675-72-9); nifedipine3,5-Pyridinedicarboxylic acid, 1,4-dihydro-2,6-dimethyl-4-(2-nitrophenyl)-, dimethyl ester CAS RN 21829-25-4); perhexyline maleate (Piperidine, 2-(2,2-dicyclohexylethyl)-, (2Z)-2-butenedioate (1:1) CAS RN 6724-53-4); oxprenolol hydrochloride2-Propanol, 14(1-methylethyl)amino]-3-[2-(2-propenyloxy)phenoxy]-, hydrochloride CAS RN 6452-73-9); pentrinitrol (1,3-Propanediol, 2,2-bis[(nitrooxy)methyl]-, mononitrate (ester) CAS RN 1607-17-6); verapamil (Benzeneacetonitrile, .alpha.-[3-[[2-(3,4-dimethoxyphenyl)ethyl]methylamino] propyl]-3,4-dimethoxy-.alpha.-(1-methylethyl)-CAS RN 52-53-9).

The term "diuretic" includes compounds that increase the excretion of solutes (mainly NaCl) and water, in general, the primary goal of diuretic therapy is to reduce extracellular fluid volume in order to lower blood pressure or rid the body of excess interstitial fluid (edema). Non-limiting examples of diuretics which may be used within the scope of this invention include althiazide (which may be prepared as disclosed in British Patent No. 902,658); benzthiazide (which may be prepared as disclosed in U.S. Pat. No. 3,108,097); buthiazide (which may be prepared as disclosed in British Patent Nos. 861,367); chlorothiazide (which may be prepared as disclosed in U.S. Pat. No. 2,809,194); spironolactone (CAS Number 52-01-7); and triamterene (CAS Number 396-01-0).

"Adrenergic stimulants" useful as cardiovascular agents in the present invention include, but are not limited to, guanfacine hydrochloride (such as N-amidino-2-(2,6-dichlorophenyl)acetamide hydrochloride, for example, TENEX® Tablets available from Robins); methyldopa-hydrochlorothiazide (such as levo-3-(3,4-dihydroxyphenyl)-2-methylalanine) combined with Hydrochlorothiazide (such as 6-chloro-3,4-dihydro-2 H-1,2,4-benzothiadiazine-7-sulfonamide 1,1-dioxide, for example, the combination as, for example, ALDORIL® Tablets available from Merck); methyldopa-chlorothiazide (such as 6-chloro-2 H-1,2,4-benzothiadiazine-7-sulfonamide 1,1-dioxide and methyldopa as described above, for example, ALDOCLORr® Tablets available from Merck); clonidine hydrochloride (such as 2-(2,6-dichlorophenylamino)-2-imidazoline hydrochloride and chlorthalidone (such as 2-chloro-5-(1-hydroxy-3-oxo-1-isoindolinyl)benzenesulfonamide), for example, COMBIPRES® Tablets available from Boehringer Ingelheim); clonidine hydrochloride (such as 2-(2,6-dichlorophenylamino)-2-imidazoline hydrochloride, for example, CATAPRES® Tablets available from Boehringer Ingelheim); clonidine (1H-Imidazol-2-amine, N-(2,6-dichlorophenyl)-4,5-dihydro-CAS RN 4205-90-7).

The anti-PGSK9 antibodies and antigen-binding fragments thereof and EGF-A polypeptides may also be administered in association with any azetidinone which inhibits intestinal cholesterol absorption. Such azetidinones include ezetimibe

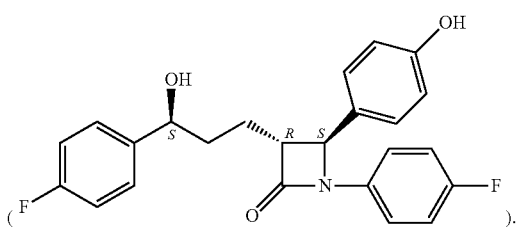

Further chemotherapeutic agents that may be administered in association with an anti-PCSK9 antibody or antigen-binding fragment thereof or EGF-A polypeptide include fish oil, eicosaepenanoic acid, docosahexanoic acid, linoleic acid, niacin, fibrates such as fenofibrate, gemfibrozil and bile acid sequestrants such as cholestyramine, colestipol and colesevelam.

Other chemotherapeutic agents include althiazide (2H-1,2,4-Benzothiadiazine-7-sulfonamide, 6-chloro-3,4-dihydro-3-[(2-propenylthio)methyl]-, 1,1-dioxide CAS RN 5588-16-9); benzthiazide (2H-1,2,4-Benzothiadiazine-7-sulfonamide, 6-chloro-3-[[(phenylmethyl)thio]methyl]-, 1,1-dioxide CAS RN 91-33-8); captopril (L-Proline, 1-[(2S)-3-mercapto-2-methyl-1-oxopropyl]-CAS RN 62571-86-2); carvedilol (2-Propanol, 1-(9H-carbazol-4-yloxy)-3-[[2-(2-methoxyphenoxy)ethyl]amino]-CAS RN 72956-09-3), chlorthiazide (sodium 2-Propanol, 1-(9H-carbazol-4-yloxy)-3-[[2-(2-methoxyphenoxy)ethyl]amino]-CAS RN 72956-09-3); clonidine hydrochloride (1H-Imidazol-2-amine, N-(2,6-dichlorophenyl)-4,5-dihydro-, monohydrochloride CAS RN 4205-91-8); cyclothiazide (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); delapril hydrochloride (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); dilevalol hydrochloride (2H-1,2,4-Benzothiadiazine-7-sulforiamide, 3-bicyclo[2.2.1]kept-5-en-2-yl-6-chloro-3,4-dihydro-, 1,1-dioxide CAS RN 2259-96-3); delapril hydrochloride (Glycine, N-[(1S)-1-(ethoxycarbonyl)-3-phenylpropyl]-L-alanyl-N-(2,3-dihydro-1H-inden-2-yl)-, monohydrochloride CAS RN 83435-67-0); doxazosin mesylate (Piperazine, 1-(4-amino-6,7-dimethoxy-2-quinazolinyl)-4-[(2,3-dihydro-1,4-benzodioxin-2-yl)carbonyl]-, monomethanesulfonate CAS RN 77883-43-3); fosinopril sodium (L-Proline, 4-cyclohexyl-1-[[(R)-[(1S)-2-methyl-1-(1-oxopropoxy)propox]); moexipril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-6,7-dimethoxy-, monohydrochloride, (3S)-CAS RN 82586-52-5); monatepil maleate (1-piperazinebutanamide, N-(6,11-dihydrodibenzo(b,e)thiepin-11-yl)-4-(4-fluorophenyl)-, (±)-, (Z)-2-butenedioate (1:1) (±)-N-(6,11-Dihydrodibenzo(b,e)thiepin-11-yl)-4-(p-fluorophenyl)-1-piperazinebutyramide maleate (1:1) CAS RN 132046-06-1), Metoprolol succinate (Butanedioic acid, compd. with 1-[4-(2-methoxyethyl)phenoxy]-3-[(1-methylethyl)amino]-2-propanol (1:2) CAS RN 98418-47-4); guanfacine hydrochloride (Benzeneacetamide, N-(aminoiminomethyl)-2,6-dichloro-, monohydrochloride CAS RN 29110-48-3; methyldopa (L-Tyrosine, 3-hydroxy-.alpha.-methyl-CAS RN 555-30-6); quinaprilat (3-Isoquinolinecarboxylic acid, 2-[(2S)-2-[[(1S)-1-carboxy-3-phenylpropyl]amino]-1-oxopropyl]-1,2,3,4-tetrahydro-, (3S)-CAS RN 82768-85-2); quinapril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-, monohydrochloride, (3S)-CAS RN 82586-55-8); Primidolol (2,4(1H,3H)-Pyrimidinedione, 1-[2-[[2-hydroxy-3-(2-methylphenoxy)propyl]amino]ethyl]-5-methyl-CAS RN 67227-55-8); prazosin hydrochloride (Piperazine, 1-(4-amino-6,7-dimethoxy-2-quinazolinyl)-4-(2-furanylcarbonyl)-, monohydrochloride CAS RN 19237-84-4); pelanserin hydrochloride 2,4(1H,3H)-Quinazolinedione, 3-[3-(4-phenyl-1-piperazinyl)propyl]-, monohydrochloride CAS RN 42877-18-9); phenoxybenzamine hydrochloride (Benzenemethanamine, N-(2-chloroethyl)-N-(1-methyl-2-phenoxyethyl)-, hydrochloride CAS RN 63-92-3); candesartan cilexetil (1H-Benzimidazole-7-carboxylic acid, 2-ethoxy-1-[[2'-(1H-tetrazol-5-yl)[1,1'-biphenyl]-4-yl]methyl]-, 1-[[(cyclohexyloxy)carbonyl]oxy]ethyl ester CAS RN 145040-37-5); telmisartan (1,1'-Biphenyl]-2-carboxylic acid, 4'-[(1,4'-dimethyl-2'-propyl[2,6'-bi-1H-benzimidazol]-1'-yl)methyl]-CAS RN 144701-48-4); candesartan1H-Benzimidazole-7-carboxylic acid, 2-ethoxy-1-[[2'-(1H-tetrazol-5-yl)[1,1'-biphenyl]-4-yl]methyl]-CAS RN 139481-59-7); amlodipine besylate3,5-Pyridinedicarboxylic acid, 2-[(2-aminoethoxy)methyl]-4-(2-chlorophenyl)-1,4-dihydro-6-methyl-, 3-ethyl 5-methyl ester, monobenzenesulfonate CAS RN 111470-99-6 Amlodipine maleate 3,5-Pyridinedicarboxylic acid, 2-[(2-aminoethoxy)methyl]-4-(2-chlorophenyl)-1,4-dihydro-6-methyl-, 3-ethyl 5-methyl ester, (2Z)-2-butenedioate (1:1) CAS RN 88150-47-4); terazosin hydrochloride (Piperazine, 1-(4-amino-6,7-dim ethoxy-2-quinazolinyl)-4-[(tetrahydro-2-furanyl)carbonyl]-, monohydrochloride CAS RN 63074-08-8); bevantolol hydrochloride (2-Propanol, 1-[[2-(3,4-dimethoxyphenyl)ethyl]amino]-3-(3-methylphenoxy)-, hydrochloride CAS RN 42864-78-8); ramipril (Cyclopenta[b]pyrrole-2-carboxylic acid, 1-[(2S)-2-[[(1S)-1-(ethoxycarbonyl)-3-phenylpropyl]amino]-1-oxopropyl]octahydro-, (2S,3aS,6aS)-CAS RN 87333-19-5).

Screening Assays

The present invention further provides a method for identifying a substance which is a PCSK9 inhibitor or an inhibitor of PCSK9/LDL receptor binding or an inhibitor of PCSK9/EGF-A domain binding; or a substance which reduces total cholesterol level, low density lipoprotein cholesterol level, apolipoprotein B level, total cholesterol/high density lipoprotein ratio or low density lipoprotein/high density lipoprotein ratio; or a substance which treats or prevents hypercholesterolemia, hyperlipidemia, hypertriglyceridaemia, sitosterolemia, atherosclerosis, arteriosclerosis, coronary heart disease, vascular inflammation or xanthoma in a subject comprising contacting PCSK9 polypeptide or a functional fragment thereof and a polypeptide comprising LDL receptor EGF-A domain (e.g., SEC) ID NO: 3) and a sample to be tested for the presence of said substance; wherein said substance is identified if less binding of PCSK9 and the polypeptide comprising LDL receptor EGF-A domain is observed in the presence of the sample than in the absence of the sample. Any such substance identified in such an assay also forms part of the present invention.

An embodiment of the invention further comprises a negative-control assay wherein said PCSK9 and EGF-A polypeptides are contacted with a substance known not to inhibit binding of PCSK9 and LDL receptor or EGF-A domain thereof wherein the assay is determined to be operating properly if more binding of the PCSK9 and LDL receptor or EGF-A domain thereof is observed than in the present of an inhibitor of said binding.

An embodiment of the invention further comprises a positive-control assay wherein said PCSK9 and EGF-A polypeptides are contacted with a substance known to inhibit binding of PCSK9 and LDL receptor or EGF-A domain thereof wherein the assay is determined to be operating properly if less binding of the PCSK9 and LDL receptor or EGF-A domain thereof is observed than in the present of an inhibitor of said binding.

Binding of the substance can be determined using any of several methods known in the art.

EXAMPLES

The following information is provided for more clearly describing the present invention and should not be construed to limit the present invention. Any and all of the compositions and methods described below fail within the scope of the present invention.

Example 1

Soluble EGF-A Domain of the LDL Receptor or Anti-PCSK9 Antibody Blocks the LDLR-PCSK9 Interaction In this example, a soluble peptide encoding the EGF-A domain of the human LDL receptor as well as various anti-PCSK9 antibodies are shown to block interactions between PCSK9 and the receptor.

The following are the AlphaScreen methods and materials for the antibody and EGF-A inhibition of PCSK9-LDLR interaction experiments:

Purified PCSK9 carrying a C-terminal FLAG tag was purified from HEK293 cells stably expressing PCSK9. Purity was estimated, by silver staining, at greater than >90%. Anti-PCSK9-catalytic domain antibody was purchased from Cayman Chemical (Rabbit anti-murine-PCSK9 polyclonal antibody, Cayman Chemical; Ann Arbor, Mich.; Cat.#10008811). This rabbit anti-mouse/human PCSK9-catalytic domain antibody recognizes an epitope with the following amino acid sequence: VFAQSIPWNLER (SEQ ID NO: 8). A rabbit anti-human PCSK9 C-terminal domain antibody (which binds specifically to SRSGKRRGERMEA (amino acids 490-502 of SEQ ID NO: 4)) and a rabbit anti-human PCSK9 whole protein antibody were also used.

Soluble EGF-A domain peptide was synthetically generated using standard methods. 2.5 ng of purified, C-terminally FLAG tagged PCSK9 (2.5 ng/2.5 ul/well of a ProxiPlate-384 Plus (Perkin-Elmer; Waltham, Mass) in 2.5 microliters of buffer (25 mM HEPES, 0.1M NaCl, 0.1% BSA, pH 7.5) was pre-incubated with 2.5 microliters of either anti-PCSK9 antibody or EGF-A domain peptide at the indicated concentrations for 30 minutes at room temperature. Next, 5 ul buffer containing 2.5 ng purified HiS-tagged soluble LDLR (R&D Systems; Minneapolis, Minn.; Cat# 2148-LD/CF; SEQ ID NO: 2) and 5 ng biotinylated anti-FLAG antibody (BioM2 monoclonal antibody, Sigma; St, Louis, Mo.; Gat.# F 9291), and the mixture, was incubated at room temperature for a further 30 minutes. Finally, under low light conditions, 5 ul of a donor/acceptor bead mixture (AlphaScreen Histidine Detection Kit, Perkin-Elmer; Waltham, Mass.; Cat.#6760619C) was added and alphaScreen signal was detected using the 2103 EnVision Multilabel Plate Reader (Perkin-Elmer; Waltham, Mass). The donor/acceptor bead mixture was prepared in dark conditions by adding 10 ul Nickel-Acceptor bead and 10 ul SA-Donor bead to 2.2 ml buffer for one 384-well plate and incubated in dark at room temperature for at least 2 hours.

The data generated in these experiments is set forth below in Tables 1-3.

TABLE 1

Inhibition of PCSK9-LDLR interaction by soluble LDLR-EGF-A domain in the presence or absence of added calcium*.
Values are the mean of three replicates.

| log[EGFA]uM | No calcium (mean counts) | 2 mM Calcium (mean counts) |
|---|---|---|
| 2.30103 | 8476 | 4098.333 |
| 1.823909 | 25291 | 6320.667 |
| 1.346787 | 74404.33 | 27519 |
| 0.869666 | 132192.7 | 80542.67 |
| 0.392545 | 182225.3 | 143204.7 |
| −0.08458 | 205094.7 | 202404.3 |
| −0.5617 | 214258 | 234140.3 |
| −1.03882 | 219281 | 246093.7 |
| −1.51594 | 221429 | 240820.7 |
| −1.99306 | 220878 | 257794 |
| −2.47018 | 206909.3 | 254980.3 |

*A lower number of counts represents less observed PCSK9/LDL receptor binding.

These data indicate that the PCSK9-LDLR interaction is inhibited by soluble EGF-A domain in the presence or absence of calcium. A slightly greater level of inhibition was observed in the presence of calcium than in the absence of calcium. In the presence of calcium, the IC50 was about 3 micromolar and in the absence of calcium the IC50 was about 12 micromolar.

TABLE 2

Inhibition of PCSK9-LDLR interaction by anti-PCSK9 antibodies (catalytic domain (Cat) and C-terminal domain (CT))

| log[antibody]ug/ml | Control IgG | Anti-PCSK9 (Cat) | Anti-PCSK9 (CT) |
|---|---|---|---|
| 1.826075 | 113607.7 | 6840 | 37878 |
| 1.348954 | 135127.7 | 25815 | 87575.33 |
| 0.871832 | 139744.7 | 55616 | 108605.7 |
| 0.394711 | 135829.3 | 93545.67 | 119019.3 |
| −0.08241 | 140328.3 | 94768 | 127197 |
| −0.55953 | 139224.7 | 128021.3 | 127770.3 |
| −1.03665 | 127405.7 | 124136.7 | 129751.7 |
| −1.51377 | 133565.3 | 126417.7 | 131044.3 |
| −1.9909 | 135194.7 | 129937.3 | 131160.7 |
| −2.46802 | 140051.7 | 131985.3 | 128822.3 |

These data demonstrate that an anti-PCSK9 catalytic domain antibody and an anti-PCSK9 C-terminal domain antibody inhibits the interaction between PCSK9 and LDL receptor. The anti-PCSK9 raised against a C-terminal domain was less effective at inhibiting the interaction. A non-specific IgG control was ineffective at inhibiting the interaction and is shown for comparison. Values in this table are the mean of three replicates.

TABLE 3

Inhibition of PCSK9-LDLR interaction by anti-PCSK9 antibodies (catalytic domain (Cat) and whole protein (whole))

| log[antibody]ug/ml | Control IgG | Anti-PCSK9 (Cat) | Anti-PCSK9 (whole) |
|---|---|---|---|
| 1.826075 | 61920.67 | 2101.33 | 1005.33 |
| 1.348954 | 74394.33 | 12259.00 | 1435.00 |
| 0.871832 | 79625.67 | 33347.33 | 14236.67 |
| 0.394711 | 79552.00 | 60074.00 | 52994.00 |
| −0.08241 | 82751.00 | 70040.00 | 75020.33 |
| −0.55953 | 88110.00 | 77438.00 | 85241.00 |
| −1.03665 | 84421.00 | 79789.00 | 82679.00 |
| −1.51377 | 83144.67 | 85603.67 | 87349.33 |
| −1.9909 | 80747.33 | 81462.67 | 80731.67 |
| −2.46802 | 78151.33 | 80556.33 | 83171.00 |
| −2.94514 | 82101.00 | 85405.33 | 80429.00 |

These data demonstrate that the PCSK9-LDLR interaction is inhibited by antibodies that bind the PCSK9 catalytic domain peptide and antibodies raised against the whole PCSK9 protein. A non-specific IgG control was ineffective at inhibiting the interaction and is shown for comparison. These values are mean of three replicates.

Example 2

Anti-PCSK9 Antibody Treatment of Cells Leads to Enhanced LDL Uptake

Incubation of cells with soluble PCSK9 leads to a decrease in the ability of the cells to absorb and clear low density lipoprotein (LDL) from the medium. This example demonstrates that inhibition of PCSK9 with an anti-PCSK9 antibody antagonizes this effect of PCSK9 and leads to increased levels of LDL uptake and clearance.

The uptake assays were performed as follows: HepG2 cells at 10,000 cells/well in 384 Collagen I coated plate were seeded and grown overnight. On the next day, a serial dilution of bacu-PCSK9-WT in MEM-1% BSA was made, mixing with a fixed concentration of anti-mouse-cat domain PCSK9 polyclonal antibody (Cayman Chemical; Ann Arbor, Mich.; cat# 10008811; raised against mouse PCSK9 antigen VFAQ-SIPWNLER (SEQ ID NO: 8) and cross reacts with human PCSK9) or anti-human PCSK9 polyclonal antibody (R&D Systems, Minneapolis, Minn.; cat# AF3888) at a final concentration of 100 ug/ml respectively. These mixtures were incubated for 1 hour at 4° C., then medium was aspirated out from the HepG2 cells and 25 ul/well of the mixtures was added to HepG2 cells in 384 plate and incubated for 6 hours and 18 hours, respectively. After the indicated incubation time, the mixture was removed from the HepG2 cells, washed 1× with PBS, then Dil-LDL (DII label is 1,1'-dioctadecyl-3, 3,3',3'-tetramethylindocarbocyanine perchlorate) was added at 10 ug/ml in MEM-1% BSA to the cells, then incubation followed at room temperature for 90 minutes. Dil-LDL was removed afterwards, the cells were fixed with Prefer fixative (glyoxal, ethanol, buffer; Anatech LTD.; Hayward, Calif.; cat# 414) for 20 minutes, then the cells were washed with PBS two times and Dil-LDL uptake into the cells was read using a fluorescence intensity reader Analyst. The data generated in these assays are set forth below in Table 4.

TABLE 4

LDL uptake in the presence of PCSK9 and anti-PCSK9 antibodies.

| [PCSK9] ug/ml | control | anti-CAT | anti-all |
|---|---|---|---|
| 6 hour incubation | | | |
| 15 | 20675218 | 22419420 | 18606777 |
| 5 | 21873226 | 25617426 | 31744993 |
| 1.67 | 23647886 | 29483684 | 30994715 |
| 0 | 29824887 | 28736616 | 30124921 |
| 18 hour incubation | | | |
| 15 | 20163100 | 21843043 | 17106209 |
| 5 | 24214957 | 25921384 | 27741479 |
| 1.67 | 27777510 | 32019111 | 29054521 |
| 0 | 31232393 | 32526668 | 28127286 |

Table 4 shows uptake of dil-labeled LDL by human HepG2 liver cells treated with the indicated amounts of purified, recombinant PCSK9 (control) or PCSK9 in the presence of either polyclonal antibody raised against the catalytic domain peptide (anti-CAT) or antibody raised against the whole protein (anti-all). PCSK9-dependent uptake of LDL by the cells increased in a manner dependent upon the presence of anti-PCSK9 antibody in the mixture. Higher numbers indicated greater LDL uptake and preservation of LDLR despite the presence of PCSK9.

Example 3

Characterization of Anti-PCSK9 Antibodies

The 75B9, 77D10, 11B5, 22D11, 1F11/1G11 and 29C10 anti-PCSK9 antibodies were characterized. The antibodies were found to effectively inhibit interaction between PCSK9 and the LDL receptor as well as inhibit PCSK9-mediated LDL receptor degradation. In vivo, the antibodies were found to inhibit PCSK9 and, thereby increase the levels of LDL receptor present. Moreover, the antibodies neutralized the in vivo cholesterol increase observed when exogenous PCSK9 was added.

Inhibition of PCSK9-Mediated LDLR Degradation with anti-PCSK9 Antibodies,

The 75B9, 77D10, 11B5, 22D11, 1F11/1G11 and 29C10 antibodies were evaluated in an in-cell western assay for their ability to inhibit the degradation of the LDL receptor by PCSK9 in HepG2 cells.

In-cell western was performed to quantitate anti-PCSK9 antibody inhibition of PCSK9-mediated LDLR degradation. HepG2 cells were seeded in 384-well collagen I coated plates and treated with anti-PCSK9 antibody and/or PCSK9 (100 nM) for 18 hours. Detection of LDLR and β-actin was performed according to the manufacturer's protocol (Li-Cor Biosciences; Lincoln, Nebr.) using the antibodies described above in conjunction with IRDye 800CW goat anti-rabbit (Li-Cor) and IRDye 680 goat anti-mouse (Li-Cor). The assay was read on an Odyssey infrared imaging system (Li-Cor) and the signal for LDLR protein in each well normalized to β-actin content. The data from these experiments are set forth below in Table 5.

TABLE 5

Level of inhibition of each anti-PCSK9 antibody observed in in-cell western assay

| Treatment | Relative level of inhibition of LDLR degradation observed* |
|---|---|
| 75B9 anti-PCSK9 antibody (IgG2a) | ++ |
| 77D10 anti-PCSK9 antibody (IgG2b) | ++ |
| 11B5 anti-PCSK9 antibody (IgG2a) | ++ |
| 22D11 anti-PCSK9 antibody (IgG1) | + |
| 1F11/1G11 anti-PCSK9 antibody (IgG2a) | +++ |
| 29C10 anti-PCSK9 antibody (IgG2a) | + |
| No PCSK9 control | 100% |
| +PCSK9/no antibody control | 0% |

*Greater number of + symbols indicates a greater level of inhibition relative to other treatments.
Relative to the "+PCSK9/no antibody" control, the antibodies tested inhibited PCSK9-mediated degradation of LDL receptor with various potencies in the HepG2 cells.

Alphascreen Binding Assays

An Amplified Luminescent Proximity Homogeneous Assay (ALPHA, Perkin-Elmer; Waltham, Mass.) capable of directly determining the interaction between PCSK9-FLAG and a putative binding partner was used to determine the effect of anti-PCSK9 antibodies on this interaction. This technique required that "donor" and "acceptor" beads be brought into proximity via protein-protein interaction, resulting in increased luminescence (Ullman et al., Proc. Nat. Acad. Sci. (1994) 91:5426-5430). In the basic assay, LDL receptor binding to PCSK9 was determined as follows: 5 µl of recombinant receptor at the appropriate concentrations was incubated with 2.5 µl PCSK9-FLAG (1.4 µg/ml, 30 min). About 2.5 µl of biotinylated anti-Flag-M2 antibody (1.8 µg/ml) was added and the mixture incubated for 1 hour. Afterward 5 µl of streptavidin donor bead and nickel chelate acceptor bead (1:1 mixture) was added and the assay incubated overnight. AlphaScreen signal (counts per second) was analyzed using an EnVision microplate reader (Perkin-Elmer). All data points were determined in triplicate. Assays were carried out at 23° C. in buffer containing 25 mM HEPES, 0.1 M NaCl, pH 7.4, 0.1% BSA. The inhibition assays were determined similarly with slight adjustments to assay volumes and protein concentrations. Briefly, 5 µl of 1.25 µg/ml of PCSK9-Flag and 1.25 µg/ml of His-tagged LDL receptor was incubated with 2.5 µl of antibody at the appropriate concentrations for 30 minutes followed by the addition of 2.5 µl of anti-Flag-BioM2 (1.8 µg/ml) and a 1 hour incubation. The data from these assays are set forth below in Table 6.

TABLE 6

Level of anti-PCSK9 antibody mediated inhibition of PCSK9/LDLR interaction

| Treatment | $IC_{50}$ (nM) | % inhibition at 450 nM of antibody |
|---|---|---|
| 75B9 anti-PCSK9 antibody (IgG2a) | 0.5 | 100 |
| 77D10 anti-PCSK9 antibody (IgG2b) | 38 | 62 |
| 11B5 anti-PCSK9 antibody (IgG2a) | 0.4 | 100 |
| 22D11 anti-PCSK9 antibody (IgG1) | ND | ND |
| 1F11/1G11 anti-PCSK9 antibody (IgG2a) | 0.049* | 88* |
| 29C10 anti-PCSK9 antibody (IgG2a) | 13 | 71 |

*Average of two measurements.
The antibodies tested inhibited PCSK9/LDL receptor interaction with various potencies (expressed in terms of $IC_{50}$ and % inhibition relative to the assay performed with no antibody added).

Effect of Anti-PCSK9 on in vivo Inhibition of LDLR Degradation and Plasma Cholesterol The ability of an anti-PCSK9 antibody (1F11/1G11) to inhibit LDL receptor degration in mice was evaluated in these assays along with the ability of the antibodies to modulate cholesterol levels.

In vivo Procedure:

Time-0: Male C57BL16j mice were injected, intraperitoneal, with 400 µg of anti-human PCSK9 Antibody, 1F11/1G11.

Time-2 hours: Mice were then injected, intravenously, with 10 µg of human PCSK9 Protein.

Time-4 hours: Mice were terminated and plasma and liver samples were collected.

Analysis:

Plasma lipoprotein profiles of individual mice (0.1 mL plasma) were determined by fast protein liquid chromatography (FPLC) with a Pharmacia Superose 6 column. FPLC fraction cholesterol levels were determined using Wako Cholesterol Enzymatic colorimetric method.

Protein levels of Liver LDL Receptor were determined by Western Blot. 40 µg of each liver homogenate was separated on an Invitrogen 4-12% NuPAGE gel, transferred to PVDF membrane and incubated with goat anti-mouse LDL receptor antibody (rabbit anti-GAPDH antibody was used as a control for equal loading). Membranes were then incubated with corresponding HRP-linked antibodies and visualization was accomplished with high performance chemiluminescence film. Band intensities were quantified using ImageQuant 5.2 software.

LDL receptor levels were expressed in Arbitrary Units (AU) as a ratio of LDL receptor band intensity to GAPDH band intensity. The results of the LDL receptor measurements are set forth in tables 7 and 8 below. Two separate analyses of the data are presented,

TABLE 7

Lightest exposure of both LDLR panel vs. GAPDH panel

| Mouse | LDLR | GAPDH | LDLR/GAPDH | Mean | % Change |
|---|---|---|---|---|---|
| 107 | 13714 | 50469 | 0.272 | 0.235 | −48.0 |
| 108 | 13766 | 49467 | 0.278 | (Antibody | |
| 109 | 12508 | 47790 | 0.262 | and PCSK9) | |
| 110 | 5977 | 46744 | 0.128 | | |
| 111 | 1724 | 46456 | 0.037 | 0.081 | −82.0 |
| 112 | 912 | 44130 | 0.021 | (Saline and | |
| 113 | 2631 | 51367 | 0.051 | PCSK9) | |
| 114 | 10217 | 47345 | 0.216 | | |
| 115 | 23237 | 48860 | 0.476 | 0.452 | Control |
| 116 | 18589 | 47694 | 0.390 | (Saline only) | |
| 117 | 16577 | 47554 | 0.349 | | |
| 118 | 27116 | 45755 | 0.593 | | |

TABLE 8

Darker exposure of LDLR panel vs. lightest GAPDH panel.

| Mouse | LDLR | GAPDH | LDLR/GAPDH | Mean | % Change |
|---|---|---|---|---|---|
| 107 | 19883 | 45242 | 0.439 | 0.377 | −35.2 |
| 108 | 18057 | 45634 | 0.396 | (Antibody | |
| 109 | 18642 | 43767 | 0.426 | and PCSK9) | |
| 110 | 10669 | 42898 | 0.249 | | |

TABLE 8-continued

Darker exposure of LDLR panel vs. lightest GAPDH panel.

| Mouse | LDLR | GAPDH | LDLR/GAPDH | Mean | % Change |
|---|---|---|---|---|---|
| 111 | 2817 | 43967 | 0.064 | 0.123 | −78.8 |
| 112 | 1204 | 43206 | 0.028 | (Saline and | |
| 113 | 4252 | 47846 | 0.089 | PCSK9) | |
| 114 | 13848 | 44288 | 0.313 | | |
| 115 | 27675 | 44510 | 0.622 | 0.582 | Control |
| 116 | 23016 | 45090 | 0.510 | Saline only) | |
| 117 | 19837 | 44526 | 0.446 | | |
| 118 | 32897 | 43792 | 0.751 | | |

The 1F11/1G11 antibody reduced the levels of PCSK9 mediated LDL receptor degration in the mice tested.

TABLE 9

Plasma cholesterol levels in mice tested under indicated conditions.

| Treatment | Plasma total cholesterol level (mg/dl) |
|---|---|
| Anti-PCSK9 and PCSK9 | 72.05 |
| Saline and PCSK9 | 83.28 |
| Saline only | 74.88 |

The 1F11/1G11 antibody reduced the level of PCSK9-mediated cholesterol increase in the mice tested.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. An isolated antibody or antigen binding fragment thereof, which binds to a PCSK9 protein, comprising:
   (a) CDR-H1 (SEQ ID NO: 51), CDR-H2 (SEQ ID NO: 52) and CDR-H3 (SEQ ID NO: 53) of an immunoglobulin heavy chain variable region which comprises the amino acid sequence of SEQ ID NO: 50; and
   (b) CDR-L1 (SEQ ID NO: 55), CDR-L2 (SEQ ID NO: 56) and CDR-L3 (SEQ ID NO: 57) of an immunoglobulin light chain variable region which comprises the amino acid sequence of SEQ ID NO: 54.

2. The antibody or antigen-binding fragment thereof of claim 1, wherein the antibody is selected from the group consisting of: a monoclonal antibody, a labeled antibody, a bivalent antibody, a bispecific antibody, a chimeric antibody, a recombinant antibody, a humanized antibody or a bispecific antibody.

3. The antibody or antigen binding fragment thereof of claim 1, wherein the antigen binding fragment is selected from the group consisting of: an scfv, an scfv dimer, a dsfv, a (dsfv)2, a dsFv-dsfv', a bispecific ds diabody, an Fv, an Fab', an Fab', and an F(ab')2.

4. The antigen binding fragment of claim 1 which is linked to an immunoglobulin constant region polypeptide.

5. The polypeptide of claim 4 wherein the constant region polypeptide is a κ light chain, γ1 heavy chain, γ2 heavy chain, γ3 heavy chain or γ4 heavy chain.

6. A composition comprising the antibody or antigen binding fragment of claim 1 in association with a chemotherapeutic agent.

7. The composition of claim 6, wherein the chemotherapeutic agent is selected from the group consisting of: a cardiovascular agent, an adrenergic blocker, an antihypertensive agent, an angiotensin system inhibitor, an angiotensin-converting enzyme inhibitor, a coronary vasodilator, a diuretic, an adrenergic stimulant, and an HMG-CoA reductase inhibitor.

8. The composition of claim 7, wherein the chemotherapeutic agent a cardiovascular agent.

9. The composition of claim 6, wherein the chemotherapeutic agent is selected from the group consisting of ezetimibe and simvastatin.

* * * * *

```
                      SEQUENCE LISTING

<160> NUMBER OF SEQ ID NOS: 57

<210> SEQ ID NO 1
<211> LENGTH: 860
<212> TYPE: PRT
<213> ORGANISM: Homo sapiens

<400> SEQUENCE: 1

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
                20                  25                  30

Gln Cys Gln Asp Gly Lys Cys Ile Ser Tyr Lys Trp Val Cys Asp Gly
            35                  40                  45

Ser Ala Glu Cys Gln Asp Gly Ser Asp Glu Ser Gln Glu Thr Cys Leu
        50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
```

```
                225                 230                 235                 240

Phe Gln Cys Ser Asp Gly Asn Cys Ile His Gly Ser Arg Gln Cys Asp
                            245                 250                 255

Arg Glu Tyr Asp Cys Lys Asp Met Ser Asp Glu Val Gly Cys Val Asn
                            260                 265                 270

Val Thr Leu Cys Glu Gly Pro Asn Lys Phe Lys Cys His Ser Gly Glu
                            275                 280                 285

Cys Ile Thr Leu Asp Lys Val Cys Asn Met Ala Arg Asp Cys Arg Asp
                            290                 295                 300

Trp Ser Asp Glu Pro Ile Lys Glu Cys Gly Thr Asn Glu Cys Leu Asp
        305                 310                 315                 320

Asn Asn Gly Gly Cys Ser His Val Cys Asn Asp Leu Lys Ile Gly Tyr
                            325                 330                 335

Glu Cys Leu Cys Pro Asp Gly Phe Gln Leu Val Ala Gln Arg Arg Cys
                            340                 345                 350

Glu Asp Ile Asp Glu Cys Gln Asp Pro Asp Thr Cys Ser Gln Leu Cys
                            355                 360                 365

Val Asn Leu Glu Gly Gly Tyr Lys Cys Gln Cys Glu Glu Gly Phe Gln
                            370                 375                 380

Leu Asp Pro His Thr Lys Ala Cys Lys Ala Val Gly Ser Ile Ala Tyr
        385                 390                 395                 400

Leu Phe Phe Thr Asn Arg His Glu Val Arg Lys Met Thr Leu Asp Arg
                            405                 410                 415

Ser Glu Tyr Thr Ser Leu Ile Pro Asn Leu Arg Asn Val Val Ala Leu
                            420                 425                 430

Asp Thr Glu Val Ala Ser Asn Arg Ile Tyr Trp Ser Asp Leu Ser Gln
                            435                 440                 445

Arg Met Ile Cys Ser Thr Gln Leu Asp Arg Ala His Gly Val Ser Ser
                            450                 455                 460

Tyr Asp Thr Val Ile Ser Arg Asp Ile Gln Ala Pro Asp Gly Leu Ala
        465                 470                 475                 480

Val Asp Trp Ile His Ser Asn Ile Tyr Trp Thr Asp Ser Val Leu Gly
                            485                 490                 495

Thr Val Ser Val Ala Asp Thr Lys Gly Val Lys Arg Lys Thr Leu Phe
                            500                 505                 510

Arg Glu Asn Gly Ser Lys Pro Arg Ala Ile Val Val Asp Pro Val His
                            515                 520                 525

Gly Phe Met Tyr Trp Thr Asp Trp Gly Thr Pro Ala Lys Ile Lys Lys
                            530                 535                 540

Gly Gly Leu Asn Gly Val Asp Ile Tyr Ser Leu Val Thr Glu Asn Ile
        545                 550                 555                 560

Gln Trp Pro Asn Gly Ile Thr Leu Asp Leu Leu Ser Gly Arg Leu Tyr
                            565                 570                 575

Trp Val Asp Ser Lys Leu His Ser Ile Ser Ser Ile Asp Val Asn Gly
                            580                 585                 590

Gly Asn Arg Lys Thr Ile Leu Glu Asp Glu Lys Arg Leu Ala His Pro
                            595                 600                 605

Phe Ser Leu Ala Val Phe Glu Asp Lys Val Phe Trp Thr Asp Ile Ile
                            610                 615                 620

Asn Glu Ala Ile Phe Ser Ala Asn Arg Leu Thr Gly Ser Asp Val Asn
        625                 630                 635                 640

Leu Leu Ala Glu Asn Leu Leu Ser Pro Glu Asp Met Val Leu Phe His
                            645                 650                 655
```

```
Asn Leu Thr Gln Pro Arg Gly Val Asn Trp Cys Glu Arg Thr Thr Leu
            660                 665                 670
Ser Asn Gly Gly Cys Gln Tyr Leu Cys Leu Pro Ala Pro Gln Ile Asn
        675                 680                 685
Pro His Ser Pro Lys Phe Thr Cys Ala Cys Pro Asp Gly Met Leu Leu
    690                 695                 700
Ala Arg Asp Met Arg Ser Cys Leu Thr Glu Ala Glu Ala Val Ala
705                 710                 715                 720
Thr Gln Glu Thr Ser Thr Val Arg Leu Lys Val Ser Thr Ala Val
            725                 730                 735
Arg Thr Gln His Thr Thr Thr Arg Pro Val Pro Asp Thr Ser Arg Leu
            740                 745                 750
Pro Gly Ala Thr Pro Gly Leu Thr Thr Val Glu Ile Val Thr Met Ser
        755                 760                 765
His Gln Ala Leu Gly Asp Val Ala Gly Arg Gly Asn Glu Lys Lys Pro
    770                 775                 780
Ser Ser Val Arg Ala Leu Ser Ile Val Leu Pro Ile Val Leu Leu Val
785                 790                 795                 800
Phe Leu Cys Leu Gly Val Phe Leu Leu Trp Lys Asn Trp Arg Leu Lys
            805                 810                 815
Asn Ile Asn Ser Ile Asn Phe Asp Asn Pro Val Tyr Gln Lys Thr Thr
            820                 825                 830
Glu Asp Glu Val His Ile Cys His Asn Gln Asp Gly Tyr Ser Tyr Pro
        835                 840                 845
Ser Arg Gln Met Val Ser Leu Glu Asp Val Ala
    850                 855                 860

<210> SEQ ID NO 2
<211> LENGTH: 767
<212> TYPE: PRT
<213> ORGANISM: Homo sapiens

<400> SEQUENCE: 2

Ala Val Gly Asp Arg Cys Glu Arg Asn Glu Phe Gln Cys Gln Asp Gly
1               5                   10                  15
Lys Cys Ile Ser Tyr Lys Trp Val Cys Asp Gly Ser Ala Glu Cys Gln
            20                  25                  30
Asp Gly Ser Asp Glu Ser Gln Glu Thr Cys Leu Ser Val Thr Cys Lys
        35                  40                  45
Ser Gly Asp Phe Ser Cys Gly Gly Arg Val Asn Arg Cys Ile Pro Gln
    50                  55                  60
Phe Trp Arg Cys Asp Gly Gln Val Asp Cys Asp Asn Gly Ser Asp Glu
65              70                  75                  80
Gln Gly Cys Pro Pro Lys Thr Cys Ser Gln Asp Glu Phe Arg Cys His
            85                  90                  95
Asp Gly Lys Cys Ile Ser Arg Gln Phe Val Cys Asp Ser Asp Arg Asp
        100                 105                 110
Cys Leu Asp Gly Ser Asp Glu Ala Ser Cys Pro Val Leu Thr Cys Gly
    115                 120                 125
Pro Ala Ser Phe Gln Cys Asn Ser Ser Thr Cys Ile Pro Gln Leu Trp
    130                 135                 140
Ala Cys Asp Asn Asp Pro Asp Cys Glu Asp Gly Ser Asp Glu Trp Pro
145                 150                 155                 160
Gln Arg Cys Arg Gly Leu Tyr Val Phe Gln Gly Asp Ser Ser Pro Cys
            165                 170                 175
```

-continued

```
Ser Ala Phe Glu Phe His Cys Leu Ser Gly Glu Cys Ile His Ser Ser
            180                 185                 190

Trp Arg Cys Asp Gly Gly Pro Asp Cys Lys Asp Lys Ser Asp Glu Glu
        195                 200                 205

Asn Cys Ala Val Ala Thr Cys Arg Pro Asp Glu Phe Gln Cys Ser Asp
    210                 215                 220

Gly Asn Cys Ile His Gly Ser Arg Gln Cys Asp Arg Glu Tyr Asp Cys
225                 230                 235                 240

Lys Asp Met Ser Asp Glu Val Gly Cys Val Asn Val Thr Leu Cys Glu
                245                 250                 255

Gly Pro Asn Lys Phe Lys Cys His Ser Gly Glu Cys Ile Thr Leu Asp
            260                 265                 270

Lys Val Cys Asn Met Ala Arg Asp Cys Arg Asp Trp Ser Asp Glu Pro
        275                 280                 285

Ile Lys Glu Cys Gly Thr Asn Glu Cys Leu Asp Asn Asn Gly Gly Cys
    290                 295                 300

Ser His Val Cys Asn Asp Leu Lys Ile Gly Tyr Glu Cys Leu Cys Pro
305                 310                 315                 320

Asp Gly Phe Gln Leu Val Ala Gln Arg Arg Cys Glu Asp Ile Asp Glu
                325                 330                 335

Cys Gln Asp Pro Asp Thr Cys Ser Gln Leu Cys Val Asn Leu Glu Gly
            340                 345                 350

Gly Tyr Lys Cys Gln Cys Glu Glu Gly Phe Gln Leu Asp Pro His Thr
        355                 360                 365

Lys Ala Cys Lys Ala Val Gly Ser Ile Ala Tyr Leu Phe Phe Thr Asn
    370                 375                 380

Arg His Glu Val Arg Lys Met Thr Leu Asp Arg Ser Glu Tyr Thr Ser
385                 390                 395                 400

Leu Ile Pro Asn Leu Arg Asn Val Val Ala Leu Asp Thr Glu Val Ala
                405                 410                 415

Ser Asn Arg Ile Tyr Trp Ser Asp Leu Ser Gln Arg Met Ile Cys Ser
            420                 425                 430

Thr Gln Leu Asp Arg Ala His Gly Val Ser Ser Tyr Asp Thr Val Ile
        435                 440                 445

Ser Arg Asp Ile Gln Ala Pro Asp Gly Leu Ala Val Asp Trp Ile His
    450                 455                 460

Ser Asn Ile Tyr Trp Thr Asp Ser Val Leu Gly Thr Val Ser Val Ala
465                 470                 475                 480

Asp Thr Lys Gly Val Lys Arg Lys Thr Leu Phe Arg Glu Asn Gly Ser
                485                 490                 495

Lys Pro Arg Ala Ile Val Val Asp Pro Val His Gly Phe Met Tyr Trp
            500                 505                 510

Thr Asp Trp Gly Thr Pro Ala Lys Ile Lys Lys Gly Gly Leu Asn Gly
        515                 520                 525

Val Asp Ile Tyr Ser Leu Val Thr Glu Asn Ile Gln Trp Pro Asn Gly
    530                 535                 540

Ile Thr Leu Asp Leu Leu Ser Gly Arg Leu Tyr Trp Val Asp Ser Lys
545                 550                 555                 560

Leu His Ser Ile Ser Ser Ile Asp Val Asn Gly Gly Asn Arg Lys Thr
                565                 570                 575

Ile Leu Glu Asp Glu Lys Arg Leu Ala His Pro Phe Ser Leu Ala Val
            580                 585                 590

Phe Glu Asp Lys Val Phe Trp Thr Asp Ile Ile Asn Glu Ala Ile Phe
        595                 600                 605
```

```
Ser Ala Asn Arg Leu Thr Gly Ser Asp Val Asn Leu Leu Ala Glu Asn
    610                 615                 620

Leu Leu Ser Pro Glu Asp Met Val Leu Phe His Asn Leu Thr Gln Pro
625                 630                 635                 640

Arg Gly Val Asn Trp Cys Glu Arg Thr Thr Leu Ser Asn Gly Gly Cys
                645                 650                 655

Gln Tyr Leu Cys Leu Pro Ala Pro Gln Ile Asn Pro His Ser Pro Lys
            660                 665                 670

Phe Thr Cys Ala Cys Pro Asp Gly Met Leu Leu Ala Arg Asp Met Arg
        675                 680                 685

Ser Cys Leu Thr Glu Ala Glu Ala Val Ala Thr Gln Glu Thr Ser
    690                 695                 700

Thr Val Arg Leu Lys Val Ser Thr Ala Val Arg Thr Gln His Thr
705                 710                 715                 720

Thr Thr Arg Pro Val Pro Asp Thr Ser Arg Leu Pro Gly Ala Thr Pro
                725                 730                 735

Gly Leu Thr Thr Val Glu Ile Val Thr Met Ser His Gln Ala Leu Gly
            740                 745                 750

Asp Val Ala Gly Arg Gly Asn Glu Lys Lys Pro Ser Ser Val Arg
    755                 760                 765

<210> SEQ ID NO 3
<211> LENGTH: 42
<212> TYPE: PRT
<213> ORGANISM: Homo sapiens

<400> SEQUENCE: 3

Gly Thr Asn Glu Cys Leu Asp Asn Asn Gly Gly Cys Ser His Val Cys
1               5                   10                  15

Asn Asp Leu Lys Ile Gly Tyr Glu Cys Leu Cys Pro Asp Gly Phe Gln
            20                  25                  30

Leu Val Ala Gln Arg Arg Cys Glu Asp Ile
        35                  40

<210> SEQ ID NO 4
<211> LENGTH: 692
<212> TYPE: PRT
<213> ORGANISM: Homo sapiens

<400> SEQUENCE: 4

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125
```

```
Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560
```

```
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
        595                 600                 605
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Gly Ala Val
            660                 665                 670
Thr Ala Val Ala Ile Cys Cys Arg Ser Arg His Leu Ala Gln Ala Ser
        675                 680                 685
Gln Glu Leu Gln
    690

<210> SEQ ID NO 5
<211> LENGTH: 677
<212> TYPE: PRT
<213> ORGANISM: Pan troglodytes

<400> SEQUENCE: 5

Met Gly Thr Val Ser Ser Arg Arg Ser Trp Trp Pro Leu Pro Leu Leu
1               5                   10                  15
Leu Leu Leu Leu Leu Leu Leu Gly Pro Ala Gly Ala Arg Ala Gln Glu
            20                  25                  30
Asp Glu Asp Gly Leu Ala Glu Ala Pro Glu His Gly Thr Thr Ala Thr
        35                  40                  45
Phe His Arg Cys Ala Lys Asp Pro Trp Arg Leu Pro Gly Thr Tyr Val
    50                  55                  60
Val Val Leu Lys Glu Glu Thr His Leu Ser Gln Ser Glu Arg Thr Ala
65                  70                  75                  80
Arg Arg Leu Gln Ala Gln Ala Ala Arg Arg Gly Tyr Leu Thr Lys Ile
                85                  90                  95
Leu His Val Phe His Gly Leu Leu Pro Gly Phe Leu Val Lys Met Ser
            100                 105                 110
Gly Asp Leu Leu Glu Leu Ala Leu Lys Leu Pro His Val Asp Tyr Ile
        115                 120                 125
Glu Glu Asp Ser Ser Val Phe Ala Gln Ser Ile Pro Trp Asn Leu Glu
    130                 135                 140
Arg Ile Thr Pro Pro Arg Tyr Arg Ala Asp Glu Tyr Gln Pro Pro Asp
145                 150                 155                 160
Gly Gly Ser Leu Val Glu Val Tyr Leu Leu Asp Thr Ser Ile Gln Ser
                165                 170                 175
Asp His Arg Glu Ile Glu Gly Arg Val Met Val Thr Asp Phe Glu Asn
            180                 185                 190
Val Pro Glu Glu Asp Gly Thr Arg Phe His Arg Gln Ala Ser Lys Cys
        195                 200                 205
Asp Ser His Gly Thr His Leu Ala Gly Val Val Ser Gly Arg Asp Ala
    210                 215                 220
Gly Val Ala Lys Gly Ala Ser Met Arg Ser Leu Arg Val Leu Asn Cys
225                 230                 235                 240
```

```
Gln Gly Lys Gly Thr Val Ser Gly Thr Leu Ile Gly Leu Glu Phe Ile
            245                 250                 255
Arg Lys Ser Gln Leu Val Gln Pro Val Gly Pro Leu Val Val Leu Leu
        260                 265                 270
Pro Leu Ala Gly Gly Tyr Ser Arg Val Leu Asn Ala Ala Cys Gln Arg
            275                 280                 285
Leu Ala Arg Ala Gly Val Val Leu Val Thr Ala Ala Gly Asn Phe Arg
        290                 295                 300
Asp Asp Ala Cys Leu Tyr Ser Pro Ala Ser Ala Pro Glu Val Ile Thr
305                 310                 315                 320
Val Gly Ala Thr Asn Ala Gln Asp Gln Pro Val Thr Leu Gly Thr Leu
                325                 330                 335
Gly Thr Asn Phe Gly Arg Cys Val Asp Leu Phe Ala Pro Gly Glu Asp
                340                 345                 350
Ile Ile Gly Ala Ser Ser Asp Cys Ser Thr Cys Phe Val Ser Gln Ser
            355                 360                 365
Gly Thr Ser Gln Ala Ala Ala His Val Ala Gly Ile Ala Ala Met Met
        370                 375                 380
Leu Ser Ala Glu Pro Glu Leu Thr Leu Ala Glu Leu Arg Gln Arg Leu
385                 390                 395                 400
Ile His Phe Ser Ala Lys Asp Val Ile Asn Glu Ala Trp Phe Pro Glu
                405                 410                 415
Asp Gln Arg Val Leu Thr Pro Asn Leu Val Ala Ala Leu Pro Pro Ser
            420                 425                 430
Thr His Gly Ala Gly Trp Gln Leu Phe Cys Arg Thr Val Trp Ser Ala
        435                 440                 445
His Ser Gly Pro Thr Arg Met Ala Thr Ala Val Ala Arg Cys Ala Pro
        450                 455                 460
Asp Glu Glu Leu Leu Ser Cys Ser Ser Phe Ser Arg Ser Gly Lys Arg
465                 470                 475                 480
Arg Gly Glu Arg Met Glu Ala Gln Gly Gly Lys Leu Val Cys Arg Ala
                485                 490                 495
His Asn Ala Phe Gly Gly Glu Gly Val Tyr Ala Ile Ala Arg Cys Cys
            500                 505                 510
Leu Leu Pro Gln Ala Asn Cys Ser Ile His Thr Ala Pro Pro Ala Glu
            515                 520                 525
Ala Gly Met Gly Thr Arg Val His Cys His Gln Gln Gly His Val Leu
        530                 535                 540
Thr Gly Cys Ser Ser His Trp Glu Val Glu Asp Leu Gly Thr His Lys
545                 550                 555                 560
Pro Pro Met Leu Arg Pro Arg Gly Gln Pro Asn Gln Cys Val Gly His
                565                 570                 575
Arg Glu Ala Ser Ile His Ala Ser Cys Cys Arg Ala Pro Gly Leu Glu
            580                 585                 590
Cys Lys Val Lys Glu His Gly Ile Pro Ala Pro Gln Glu Gln Val Thr
        595                 600                 605
Val Ala Cys Glu Glu Gly Trp Thr Leu Thr Gly Cys Ser Ala Leu Pro
        610                 615                 620
Gly Thr Ser His Val Leu Gly Ala Tyr Ala Val Asp Asn Thr Cys Val
625                 630                 635                 640
Val Arg Ser Arg Asp Val Ser Thr Ala Gly Ser Thr Ser Glu Glu Ala
                645                 650                 655
Val Ala Ala Val Ala Ile Cys Cys Arg Ser Arg His Leu Ala Gln Ala
```

Ser Gln Glu Leu Gln
        675

<210> SEQ ID NO 6
<211> LENGTH: 694
<212> TYPE: PRT
<213> ORGANISM: Mus musculus

<400> SEQUENCE: 6

Met Gly Thr His Cys Ser Ala Trp Leu Arg Trp Pro Leu Leu Pro Leu
1               5                   10                  15

Leu Pro Pro Leu Leu Leu Leu Leu Leu Cys Pro Thr Gly Ala
            20                  25                  30

Gly Ala Gln Asp Glu Asp Gly Asp Tyr Glu Glu Leu Met Leu Ala Leu
            35                  40                  45

Pro Ser Gln Glu Asp Gly Leu Ala Asp Glu Ala Ala His Val Ala Thr
50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Gly Tyr Val Ile
                100                 105                 110

Lys Val Leu His Ile Phe Tyr Asp Leu Phe Pro Gly Phe Leu Val Lys
            115                 120                 125

Met Ser Ser Asp Leu Leu Gly Leu Ala Leu Lys Leu Pro His Val Glu
            130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
                165                 170                 175

Pro Asp Gly Ser Ser Gln Val Glu Val Tyr Leu Leu Asp Thr Ser Ile
            180                 185                 190

Gln Gly Ala His Arg Glu Ile Glu Gly Arg Val Thr Ile Thr Asp Phe
            195                 200                 205

Asn Ser Val Pro Glu Glu Asp Gly Thr Arg Phe His Arg Gln Ala Ser
210                 215                 220

Lys Cys Asp Ser His Gly Thr His Leu Ala Gly Val Val Ser Gly Arg
225                 230                 235                 240

Asp Ala Gly Val Ala Lys Gly Thr Ser Leu His Ser Leu Arg Val Leu
                245                 250                 255

Asn Cys Gln Gly Lys Gly Thr Val Ser Gly Thr Leu Ile Gly Leu Glu
            260                 265                 270

Phe Ile Arg Lys Ser Gln Leu Ile Gln Pro Ser Gly Pro Leu Val Val
            275                 280                 285

Leu Leu Pro Leu Ala Gly Gly Tyr Ser Arg Ile Leu Asn Ala Ala Cys
290                 295                 300

Arg His Leu Ala Arg Thr Gly Val Val Leu Val Ala Ala Ala Gly Asn
305                 310                 315                 320

Phe Arg Asp Asp Ala Cys Leu Tyr Ser Pro Ala Ser Ala Pro Glu Val
                325                 330                 335

Ile Thr Val Gly Ala Thr Asn Ala Gln Asp Gln Pro Val Thr Leu Gly
            340                 345                 350

Thr Leu Gly Thr Asn Phe Gly Arg Cys Val Asp Leu Phe Ala Pro Gly

```
            355                 360                 365
Lys Asp Ile Ile Gly Ala Ser Ser Asp Cys Ser Thr Cys Phe Met Ser
370                 375                 380

Gln Ser Gly Thr Ser Gln Ala Ala His Val Ala Gly Ile Val Ala
385                 390                 395                 400

Arg Met Leu Ser Arg Glu Pro Thr Leu Thr Leu Ala Glu Leu Arg Gln
            405                 410                 415

Arg Leu Ile His Phe Ser Thr Lys Asp Val Ile Asn Met Ala Trp Phe
            420                 425                 430

Pro Glu Asp Gln Gln Val Leu Thr Pro Asn Leu Val Ala Thr Leu Pro
            435                 440                 445

Pro Ser Thr His Glu Thr Gly Gly Gln Leu Leu Cys Arg Thr Val Trp
450                 455                 460

Ser Ala His Ser Gly Pro Thr Arg Thr Ala Thr Ala Thr Ala Arg Cys
465                 470                 475                 480

Ala Pro Glu Glu Glu Leu Leu Ser Cys Ser Ser Phe Ser Arg Ser Gly
                485                 490                 495

Arg Arg Arg Gly Asp Trp Ile Glu Ala Ile Gly Gly Gln Gln Val Cys
                500                 505                 510

Lys Ala Leu Asn Ala Phe Gly Gly Glu Gly Val Tyr Ala Val Ala Arg
            515                 520                 525

Cys Cys Leu Val Pro Arg Ala Asn Cys Ser Ile His Asn Thr Pro Ala
530                 535                 540

Ala Arg Ala Gly Leu Glu Thr His Val His Cys His Gln Lys Asp His
545                 550                 555                 560

Val Leu Thr Gly Cys Ser Phe His Trp Glu Val Glu Asp Leu Ser Val
                565                 570                 575

Arg Arg Gln Pro Ala Leu Arg Ser Arg Arg Gln Pro Gly Gln Cys Val
            580                 585                 590

Gly His Gln Ala Ala Ser Val Tyr Ala Ser Cys Cys His Ala Pro Gly
            595                 600                 605

Leu Glu Cys Lys Ile Lys Glu His Gly Ile Ser Gly Pro Ser Glu Gln
            610                 615                 620

Val Thr Val Ala Cys Glu Ala Gly Trp Thr Leu Thr Gly Cys Asn Val
625                 630                 635                 640

Leu Pro Gly Ala Ser Leu Thr Leu Gly Ala Tyr Ser Val Asp Asn Leu
                645                 650                 655

Cys Val Ala Arg Val His Asp Thr Ala Arg Ala Asp Arg Thr Ser Gly
            660                 665                 670

Glu Ala Thr Val Ala Ala Ile Cys Cys Arg Ser Arg Pro Ser Ala
            675                 680                 685

Lys Ala Ser Trp Val Gln
    690

<210> SEQ ID NO 7
<211> LENGTH: 691
<212> TYPE: PRT
<213> ORGANISM: Rattus norvegicus

<400> SEQUENCE: 7

Met Gly Ile Arg Cys Ser Thr Trp Leu Arg Trp Pro Leu Ser Pro Gln
1               5                   10                  15

Leu Leu Leu Leu Leu Leu Cys Pro Thr Gly Ser Arg Ala Gln Asp
            20                  25                  30

Glu Asp Gly Asp Tyr Glu Glu Leu Met Leu Ala Leu Pro Ser Gln Glu
```

```
            35                  40                  45
Asp Ser Leu Val Asp Glu Ala Ser His Val Ala Thr Ala Thr Phe Arg
 50                  55                  60
Arg Cys Ser Lys Glu Ala Trp Arg Leu Pro Gly Thr Tyr Val Val
 65                  70                  75                  80
Leu Met Glu Glu Thr Gln Arg Leu Gln Val Glu Gln Thr Ala His Arg
                     85                  90                  95
Leu Gln Thr Trp Ala Ala Arg Arg Gly Tyr Val Ile Lys Val Leu His
                100                 105                 110
Val Phe Tyr Asp Leu Phe Pro Gly Phe Leu Val Lys Met Ser Ser Asp
                115                 120                 125
Leu Leu Gly Leu Ala Leu Lys Leu Pro His Val Glu Tyr Ile Glu Glu
                130                 135                 140
Asp Ser Leu Val Phe Ala Gln Ser Ile Pro Trp Asn Leu Glu Arg Ile
145                 150                 155                 160
Ile Pro Ala Trp Gln Gln Thr Glu Glu Asp Ser Ser Pro Asp Gly Ser
                    165                 170                 175
Ser Gln Val Glu Val Tyr Leu Leu Asp Thr Ser Ile Gln Ser Gly His
                180                 185                 190
Arg Glu Ile Glu Gly Arg Val Thr Ile Thr Asp Phe Asn Ser Val Pro
                195                 200                 205
Glu Glu Asp Gly Thr Arg Phe His Arg Gln Ala Ser Lys Cys Asp Ser
210                 215                 220
His Gly Thr His Leu Ala Gly Val Val Ser Gly Arg Asp Ala Gly Val
225                 230                 235                 240
Ala Lys Gly Thr Ser Leu His Ser Leu Arg Val Leu Asn Cys Gln Gly
                    245                 250                 255
Lys Gly Thr Val Ser Gly Thr Leu Ile Gly Leu Glu Phe Ile Arg Lys
                260                 265                 270
Ser Gln Leu Ile Gln Pro Ser Gly Pro Leu Val Val Leu Leu Pro Leu
                275                 280                 285
Ala Gly Gly Tyr Ser Arg Ile Leu Asn Thr Ala Cys Gln Arg Leu Ala
290                 295                 300
Arg Thr Gly Val Val Leu Val Ala Ala Ala Gly Asn Phe Arg Asp Asp
305                 310                 315                 320
Ala Cys Leu Tyr Ser Pro Ala Ser Ala Pro Glu Val Ile Thr Val Gly
                325                 330                 335
Ala Thr Asn Ala Gln Asp Gln Pro Val Thr Leu Gly Thr Leu Gly Thr
                340                 345                 350
Asn Phe Gly Arg Cys Val Asp Leu Phe Ala Pro Gly Lys Asp Ile Ile
                355                 360                 365
Gly Ala Ser Ser Asp Cys Ser Thr Cys Tyr Met Ser Gln Ser Gly Thr
370                 375                 380
Ser Gln Ala Ala Ala His Val Ala Gly Ile Val Ala Met Met Leu Asn
385                 390                 395                 400
Arg Asp Pro Ala Leu Thr Leu Ala Glu Leu Arg Gln Arg Leu Ile Leu
                405                 410                 415
Phe Ser Thr Lys Asp Val Ile Asn Met Ala Trp Phe Pro Glu Asp Gln
                420                 425                 430
Arg Val Leu Thr Pro Asn Arg Val Ala Thr Leu Pro Pro Ser Thr Gln
                435                 440                 445
Glu Thr Gly Gly Gln Leu Leu Cys Arg Thr Val Trp Ser Ala His Ser
450                 455                 460
```

Gly Pro Thr Arg Thr Ala Thr Ala Thr Ala Arg Cys Ala Pro Glu Glu
465                 470                 475                 480

Glu Leu Leu Ser Cys Ser Ser Phe Ser Arg Ser Gly Arg Arg Arg Gly
            485                 490                 495

Asp Arg Ile Glu Ala Ile Gly Gly Gln Gln Val Cys Lys Ala Leu Asn
        500                 505                 510

Ala Phe Gly Gly Glu Gly Val Tyr Ala Val Ala Arg Cys Cys Leu Leu
    515                 520                 525

Pro Arg Val Asn Cys Ser Ile His Asn Thr Pro Ala Ala Arg Ala Gly
530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Gln Pro
                565                 570                 575

Leu Leu Arg Ser Arg His Gln Pro Gly Gln Cys Val Gly His Gln Glu
            580                 585                 590

Ala Ser Val His Ala Ser Cys Cys His Ala Pro Gly Leu Glu Cys Lys
        595                 600                 605

Ile Lys Glu His Gly Ile Ala Gly Pro Ala Gln Val Thr Val Ala
    610                 615                 620

Cys Glu Ala Gly Trp Thr Leu Thr Gly Cys Asn Val Leu Pro Gly Ala
625                 630                 635                 640

Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
            660                 665                 670

Ala Ala Ala Ile Cys Cys Arg Ser Arg Pro Ser Ala Lys Ala Ser Trp
        675                 680                 685

Val His Gln
    690

<210> SEQ ID NO 8
<211> LENGTH: 12
<212> TYPE: PRT
<213> ORGANISM: Homo sapiens

<400> SEQUENCE: 8

Val Phe Ala Gln Ser Ile Pro Trp Asn Leu Glu Arg
1               5                   10

<210> SEQ ID NO 9
<211> LENGTH: 13
<212> TYPE: PRT
<213> ORGANISM: Homo sapiens

<400> SEQUENCE: 9

Ser Arg Ser Gly Lys Arg Gly Glu Arg Met Glu Ala
1               5                   10

<210> SEQ ID NO 10
<211> LENGTH: 118
<212> TYPE: PRT
<213> ORGANISM: Mus musculus

<400> SEQUENCE: 10

Glu Val Gln Leu Gln Gln Ser Gly Ala Glu Leu Val Lys Pro Gly Ala
1               5                   10                  15

Ser Val Thr Leu Ser Cys Thr Ala Ser Gly Phe Asn Ile Lys Asp Thr
            20                  25                  30

Tyr Met His Trp Val Asn Gln Arg Pro Glu Gln Gly Leu Val Trp Ile
         35                  40                  45

Gly Arg Ile Asp Pro Ala Asn Gly His Thr Glu Tyr Asp Pro Lys Phe
     50                  55                  60

Gln Asp Lys Ala Thr Ile Thr Thr Asp Thr Ser Asn Thr Ala Tyr
 65                  70                  75                  80

Leu His Leu Ser Ser Leu Thr Ser Gly Asp Thr Ala Val Tyr Tyr Cys
                 85                  90                  95

Ala Arg Ser Tyr Phe Gly Ser Ile Phe Ala Tyr Trp Gly Gln Gly Thr
            100                 105                 110

Leu Val Thr Val Ser Ala
            115

<210> SEQ ID NO 11
<211> LENGTH: 10
<212> TYPE: PRT
<213> ORGANISM: Mus musculus

<400> SEQUENCE: 11

Gly Phe Asn Ile Lys Asp Thr Tyr Met His
 1               5                  10

<210> SEQ ID NO 12
<211> LENGTH: 17
<212> TYPE: PRT
<213> ORGANISM: Mus musculus

<400> SEQUENCE: 12

Arg Ile Asp Pro Ala Asn Gly His Thr Glu Tyr Asp Pro Lys Phe Gln
 1               5                  10                  15

Asp

<210> SEQ ID NO 13
<211> LENGTH: 9
<212> TYPE: PRT
<213> ORGANISM: Mus musculus

<400> SEQUENCE: 13

Ser Tyr Phe Gly Ser Ile Phe Ala Tyr
 1               5

<210> SEQ ID NO 14
<211> LENGTH: 108
<212> TYPE: PRT
<213> ORGANISM: Mus musculus

<400> SEQUENCE: 14

Gln Ile Val Leu Thr Gln Ser Pro Ala Ile Met Ser Ala Ser Pro Gly
 1               5                  10                  15

Glu Lys Val Thr Ile Ser Cys Ser Ala Ser Ser Ser Val Ser Tyr Leu
             20                  25                  30

Tyr Trp Tyr Gln Gln Lys Pro Gly Ser Ser Pro Lys Pro Trp Ile Phe
         35                  40                  45

Arg Ser Ser His Arg Ala Ser Gly Val Pro Ala Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys His Gln Tyr Gln Ser Pro Pro Thr
                 85                  90                  95

```
Phe Gly Gly Gly Thr Lys Leu Glu Ile Lys Arg Ala
                100                 105

<210> SEQ ID NO 15
<211> LENGTH: 10
<212> TYPE: PRT
<213> ORGANISM: Mus musculus

<400> SEQUENCE: 15

Ser Ala Ser Ser Ser Val Ser Tyr Leu Tyr
1               5                   10

<210> SEQ ID NO 16
<211> LENGTH: 7
<212> TYPE: PRT
<213> ORGANISM: Mus musculus

<400> SEQUENCE: 16

Arg Ser Ser His Arg Ala Ser
1               5

<210> SEQ ID NO 17
<211> LENGTH: 9
<212> TYPE: PRT
<213> ORGANISM: Mus musculus

<400> SEQUENCE: 17

His Gln Tyr Gln Ser Tyr Pro Pro Thr
1               5

<210> SEQ ID NO 18
<211> LENGTH: 118
<212> TYPE: PRT
<213> ORGANISM: Mus musculus

<400> SEQUENCE: 18

Glu Val Gln Leu Gln Gln Ser Gly Ala Asp Leu Val Lys Pro Gly Ala
1               5                   10                  15

Ser Val Lys Leu Ser Cys Thr Ala Ser Gly Phe Asn Ile Lys Asp Thr
                20                  25                  30

Tyr Ile His Trp Val Lys Gln Arg Pro Glu Gln Gly Leu Glu Trp Ile
            35                  40                  45

Gly Arg Ile Asp Pro Ala Asn Gly His Thr Glu Tyr Asp Pro Lys Phe
        50                  55                  60

Gln Gly Arg Ala Thr Leu Thr Thr Asp Thr Ser Ser Asn Thr Ala Tyr
65                  70                  75                  80

Leu Gln Leu Phe Ser Leu Thr Ser Glu Asp Ser Ala Val Tyr Phe Cys
                85                  90                  95

Ala Arg Ser Tyr Tyr Gly Ser Ile Phe Ala Tyr Trp Gly Gln Gly Thr
                100                 105                 110

Leu Val Thr Val Ser Ala
            115

<210> SEQ ID NO 19
<211> LENGTH: 10
<212> TYPE: PRT
<213> ORGANISM: Mus musculus

<400> SEQUENCE: 19

Gly Phe Asn Ile Lys Asp Thr Tyr Ile His
1               5                   10
```

```
<210> SEQ ID NO 20
<211> LENGTH: 17
<212> TYPE: PRT
<213> ORGANISM: Mus musculus

<400> SEQUENCE: 20

Arg Ile Asp Pro Ala Asn Gly His Thr Glu Tyr Asp Pro Lys Phe Gln
1               5                   10                  15

Gly

<210> SEQ ID NO 21
<211> LENGTH: 9
<212> TYPE: PRT
<213> ORGANISM: Mus musculus

<400> SEQUENCE: 21

Ser Tyr Tyr Gly Ser Ile Phe Ala Tyr
1               5

<210> SEQ ID NO 22
<211> LENGTH: 108
<212> TYPE: PRT
<213> ORGANISM: Mus musculus

<400> SEQUENCE: 22

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Leu
                20                  25                  30

Phe Trp Tyr Gln Gln Lys Pro Gly Ser Ser Pro Lys Pro Trp Ile Phe
            35                  40                  45

Arg Thr Ser Tyr Leu Ala Ser Gly Val Pro Ala Arg Phe Ser Gly Ser
        50                  55                  60

Gly Ser Gly Thr Ser Phe Ser Leu Thr Ile Ser Ser Met Glu Ala Glu
65                  70                  75                  80

Asp Ala Ala Thr Tyr Tyr Cys His Gln Tyr His Thr Tyr Pro Pro Thr
                85                  90                  95

Phe Gly Gly Gly Thr Lys Leu Glu Ile Lys Arg Ala
            100                 105

<210> SEQ ID NO 23
<211> LENGTH: 10
<212> TYPE: PRT
<213> ORGANISM: Mus musculus

<400> SEQUENCE: 23

Ser Ala Ser Ser Ser Val Ser Tyr Leu Phe
1               5                   10

<210> SEQ ID NO 24
<211> LENGTH: 7
<212> TYPE: PRT
<213> ORGANISM: Mus musculus

<400> SEQUENCE: 24

Arg Thr Ser Tyr Leu Ala Ser
1               5

<210> SEQ ID NO 25
<211> LENGTH: 9
<212> TYPE: PRT
<213> ORGANISM: Mus musculus
```

```
<400> SEQUENCE: 25

His Gln Tyr His Thr Tyr Pro Pro Thr
1               5

<210> SEQ ID NO 26
<211> LENGTH: 121
<212> TYPE: PRT
<213> ORGANISM: Mus musculus

<400> SEQUENCE: 26

Glu Val Gln Leu Gln Gln Ser Gly Ala Glu Leu Val Arg Ser Gly Ala
1               5                   10                  15

Ser Val Lys Leu Ser Cys Thr Thr Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Ala Asp Thr Ala Val Tyr Tyr Cys
                85                  90                  95

Asn Ala Tyr Tyr Arg Tyr Asp Asp Gly Thr Trp Phe Pro Tyr Trp Gly
            100                 105                 110

Gln Gly Thr Leu Val Thr Val Ser Ala
        115                 120

<210> SEQ ID NO 27
<211> LENGTH: 10
<212> TYPE: PRT
<213> ORGANISM: Mus musculus

<400> SEQUENCE: 27

Gly Phe Asn Ile Lys Asp Tyr Tyr Ile His
1               5                   10

<210> SEQ ID NO 28
<211> LENGTH: 17
<212> TYPE: PRT
<213> ORGANISM: Mus musculus

<400> SEQUENCE: 28

Trp Ile Asp Pro Glu Asn Gly Asp Thr Glu Tyr Ala Pro Lys Phe Gln
1               5                   10                  15

Gly

<210> SEQ ID NO 29
<211> LENGTH: 12
<212> TYPE: PRT
<213> ORGANISM: Mus musculus

<400> SEQUENCE: 29

Tyr Tyr Arg Tyr Asp Asp Gly Thr Trp Phe Pro Tyr
1               5                   10

<210> SEQ ID NO 30
<211> LENGTH: 109
<212> TYPE: PRT
<213> ORGANISM: Mus musculus

<400> SEQUENCE: 30
```

```
Asp Ile Gln Leu Thr Gln Ser Pro Ala Ser Leu Ser Ala Ser Val Gly
1               5                   10                  15

Glu Thr Val Thr Ile Thr Cys Arg Ala Ser Gly Asn Ile His Ser Tyr
            20                  25                  30

Leu Ala Trp Tyr Gln Gln Lys Gln Gly Lys Ser Pro Gln Phe Leu Val
        35                  40                  45

Asp Asn Ala Lys Thr Leu Pro Asp Gly Val Pro Ser Arg Phe Ser Val
    50                  55                  60

Ser Gly Ser Gly Thr Gln Tyr Ser Leu Lys Ile Asn Ser Leu Gln Pro
65              70                  75                  80

Glu Asp Phe Gly Thr Tyr Tyr Cys Gln His Phe Trp Asn Thr Pro Trp
            85                  90                  95

Thr Phe Gly Gly Gly Thr Lys Leu Glu Ile Lys Arg Ala
            100                 105
```

<210> SEQ ID NO 31
<211> LENGTH: 11
<212> TYPE: PRT
<213> ORGANISM: Mus musculus

<400> SEQUENCE: 31

```
Arg Ala Ser Gly Asn Ile His Ser Tyr Leu Ala
1               5                   10
```

<210> SEQ ID NO 32
<211> LENGTH: 7
<212> TYPE: PRT
<213> ORGANISM: Mus musculus

<400> SEQUENCE: 32

```
Asn Ala Lys Thr Leu Pro Asp
1               5
```

<210> SEQ ID NO 33
<211> LENGTH: 9
<212> TYPE: PRT
<213> ORGANISM: Mus musculus

<400> SEQUENCE: 33

```
Gln His Phe Trp Asn Thr Pro Trp Thr
1               5
```

<210> SEQ ID NO 34
<211> LENGTH: 119
<212> TYPE: PRT
<213> ORGANISM: Mus musculus

<400> SEQUENCE: 34

```
Glu Val Leu Leu Gln Gln Ser Val Ala Glu Leu Val Arg Pro Gly Ala
1               5                   10                  15

Ser Val Arg Leu Ser Cys Thr Ala Ser Gly Phe Asn Ile Lys Asp Thr
            20                  25                  30

Tyr Ile His Trp Val Arg Gln Arg Pro Glu Gln Gly Leu Glu Trp Phe
        35                  40                  45

Gly Trp Ile Asp Pro Ala Asn Gly Tyr Thr Lys Tyr Ala Pro Asn Phe
    50                  55                  60

Gln Gly Lys Ala Thr Leu Thr Thr Asp Thr Ser Ser Asn Thr Ala Tyr
65              70                  75                  80

Leu His Leu Ser Ser Leu Thr Ser Glu Asp Ser Ala Ile Tyr Tyr Cys
            85                  90                  95
```

Ala Arg Gly Tyr Tyr Arg Tyr Ser Leu Asp Tyr Trp Gly Gln Gly
            100                 105                 110

Thr Ser Val Thr Val Ser Ser
        115

<210> SEQ ID NO 35
<211> LENGTH: 10
<212> TYPE: PRT
<213> ORGANISM: Mus musculus

<400> SEQUENCE: 35

Gly Phe Asn Ile Lys Asp Thr Tyr Ile His
1               5                   10

<210> SEQ ID NO 36
<211> LENGTH: 17
<212> TYPE: PRT
<213> ORGANISM: Mus musculus

<400> SEQUENCE: 36

Trp Ile Asp Pro Ala Asn Gly Tyr Thr Lys Tyr Ala Pro Asn Phe Gln
1               5                   10                  15

Gly

<210> SEQ ID NO 37
<211> LENGTH: 10
<212> TYPE: PRT
<213> ORGANISM: Mus musculus

<400> SEQUENCE: 37

Gly Tyr Tyr Arg Tyr Tyr Ser Leu Asp Tyr
1               5                   10

<210> SEQ ID NO 38
<211> LENGTH: 109
<212> TYPE: PRT
<213> ORGANISM: Mus musculus

<400> SEQUENCE: 38

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Ser Ser Arg Leu His Ser Gly Val Pro Ser Arg Phe Ser Gly
    50                  55                  60

Arg Gly Ser Gly Thr Asp Tyr Ser Leu Thr Ile Ser Thr Leu Glu Gln
65                  70                  75                  80

Glu Asp Ile Ala Thr Tyr Phe Cys Gln Gln Gly Lys Thr Leu Pro Leu
                85                  90                  95

Thr Phe Gly Ala Gly Thr Lys Leu Glu Leu Lys Arg Ala
            100                 105

<210> SEQ ID NO 39
<211> LENGTH: 11
<212> TYPE: PRT
<213> ORGANISM: Mus musculus

<400> SEQUENCE: 39

Arg Ala Ser Gln Asp Ile Ser Asn Tyr Leu Asn
1               5                   10

<210> SEQ ID NO 40
<211> LENGTH: 7
<212> TYPE: PRT
<213> ORGANISM: Mus musculus

<400> SEQUENCE: 40

Tyr Ser Ser Arg Leu His Ser
1               5

<210> SEQ ID NO 41
<211> LENGTH: 9
<212> TYPE: PRT
<213> ORGANISM: Mus musculus

<400> SEQUENCE: 41

Gln Gln Gly Lys Thr Leu Pro Leu Thr
1               5

<210> SEQ ID NO 42
<211> LENGTH: 126
<212> TYPE: PRT
<213> ORGANISM: Mus musculus

<400> SEQUENCE: 42

Glu Val Gln Leu Val Asp Ser Gly Gly Gly Leu Val Gln Pro Gly Arg
1               5                   10                  15

Ser Leu Lys Leu Ser Cys Ala Ala Ser Gly Phe Thr Phe Ser Asn His
            20                  25                  30

Asp Met Ala Trp Val Arg Gln Ala Pro Thr Lys Gly Leu Glu Trp Val
        35                  40                  45

Ala Ser Ile Thr Pro Ser Gly Gly Thr Thr Tyr Tyr Arg Asp Ser Val
    50                  55                  60

Glu Gly Arg Phe Thr Val Ser Arg Asp Asn Val Lys Ser Ser Leu His
65                  70                  75                  80

Leu Gln Met Asp Ser Leu Thr Ser Glu Asp Thr Ala Thr Tyr Tyr Cys
                85                  90                  95

Ala Arg Gln Asn Tyr Tyr Asp Gly Ser Tyr Tyr Tyr Gly Leu Tyr Tyr
            100                 105                 110

Phe Asp Tyr Trp Gly Gln Gly Val Met Val Thr Val Ser Ser
        115                 120                 125

<210> SEQ ID NO 43
<211> LENGTH: 10
<212> TYPE: PRT
<213> ORGANISM: Mus musculus

<400> SEQUENCE: 43

Gly Phe Thr Phe Ser Asn His Asp Met Ala
1               5                   10

<210> SEQ ID NO 44
<211> LENGTH: 17
<212> TYPE: PRT
<213> ORGANISM: Mus musculus

<400> SEQUENCE: 44

Ser Ile Thr Pro Ser Gly Gly Thr Thr Tyr Tyr Arg Asp Ser Val Glu
1               5                   10                  15

Gly

```
<210> SEQ ID NO 45
<211> LENGTH: 17
<212> TYPE: PRT
<213> ORGANISM: Mus musculus

<400> SEQUENCE: 45

Gln Asn Tyr Tyr Asp Gly Ser Tyr Tyr Gly Leu Tyr Tyr Phe Asp
1               5                   10                  15

Tyr

<210> SEQ ID NO 46
<211> LENGTH: 114
<212> TYPE: PRT
<213> ORGANISM: Mus musculus

<400> SEQUENCE: 46

Asp Val Leu Met Thr Gln Thr Pro Val Ser Leu Pro Val Ser Leu Gly
1               5                   10                  15

Gly Gln Val Ser Ile Ser Cys Arg Ser Ser Gln Ser Leu Val Tyr Ser
                20                  25                  30

Asp Gly Asn Thr Tyr Leu His Trp Tyr Leu Gln Lys Pro Gly Gln Ser
            35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Leu Gly Leu Tyr Tyr Cys Leu Gln Ser
                85                  90                  95

Thr His Phe Pro Pro Thr Phe Gly Ser Gly Thr Lys Leu Glu Ile Lys
            100                 105                 110

Arg Ala

<210> SEQ ID NO 47
<211> LENGTH: 16
<212> TYPE: PRT
<213> ORGANISM: Mus musculus

<400> SEQUENCE: 47

Arg Ser Ser Gln Ser Leu Val Tyr Ser Asp Gly Asn Thr Tyr Leu His
1               5                   10                  15

<210> SEQ ID NO 48
<211> LENGTH: 7
<212> TYPE: PRT
<213> ORGANISM: Mus musculus

<400> SEQUENCE: 48

Arg Val Ser Asn Arg Phe Ser
1               5

<210> SEQ ID NO 49
<211> LENGTH: 9
<212> TYPE: PRT
<213> ORGANISM: Mus musculus

<400> SEQUENCE: 49

Leu Gln Ser Thr His Phe Pro Pro Thr
1               5

<210> SEQ ID NO 50
<211> LENGTH: 119
<212> TYPE: PRT
```

<213> ORGANISM: Mus musculus

<400> SEQUENCE: 50

```
Glu Val Gln Leu Gln Gln Ser Gly Pro Glu Leu Val Lys Pro Gly Ala
1               5                   10                  15

Ser Val Lys Ile Ser Cys Lys Val Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Ala Ile Tyr Asn Gln Lys Phe
    50                  55                  60

Lys Gly Lys Ala Thr Leu Thr Val Asp Lys Ser Ser Ile Ala Tyr
65                  70                  75                  80

Met Glu Leu Arg Ser Leu Thr Ser Glu Asp Ser Ala Val Tyr Tyr Cys
                85                  90                  95

Thr Ser Gly Ile Ile Thr Glu Ile Ala Glu Asp Phe Trp Gly Gln Gly
                100                 105                 110

Thr Thr Leu Thr Val Ser Ser
            115
```

<210> SEQ ID NO 51
<211> LENGTH: 10
<212> TYPE: PRT
<213> ORGANISM: Mus musculus

<400> SEQUENCE: 51

```
Gly Tyr Thr Phe Thr Asp Tyr Tyr Met Asn
1               5                   10
```

<210> SEQ ID NO 52
<211> LENGTH: 17
<212> TYPE: PRT
<213> ORGANISM: Mus musculus

<400> SEQUENCE: 52

```
Asp Ile Asn Pro Asn Asn Gly Gly Ala Ile Tyr Asn Gln Lys Phe Lys
1               5                   10                  15

Gly
```

<210> SEQ ID NO 53
<211> LENGTH: 10
<212> TYPE: PRT
<213> ORGANISM: Mus musculus

<400> SEQUENCE: 53

```
Gly Ile Ile Thr Glu Ile Ala Glu Asp Phe
1               5                   10
```

<210> SEQ ID NO 54
<211> LENGTH: 109
<212> TYPE: PRT
<213> ORGANISM: Mus musculus

<400> SEQUENCE: 54

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Val Trp Tyr Gln Gln Lys Pro Gly Gln Ser Pro Lys Ala Leu Ile
        35                  40                  45
```

```
His Ser Ala Ser Tyr Arg Tyr Ser Gly Val Pro Asp Arg Phe Lys Gly
    50                  55                  60

Ser Gly Ser Gly Thr Asp Phe Thr Leu Thr Ile Thr Asn Val Gln Ser
65              70                  75                  80

Glu Asp Leu Ala Gly Phe Phe Cys Gln Gln Tyr Lys Thr Tyr Pro Tyr
                85              90                  95

Thr Phe Gly Gly Gly Thr Gln Leu Glu Ile Lys Arg Ala
            100             105

<210> SEQ ID NO 55
<211> LENGTH: 11
<212> TYPE: PRT
<213> ORGANISM: Mus musculus

<400> SEQUENCE: 55

Lys Ala Ser Gln Asn Val Gly Thr Asn Val Val
1               5                   10

<210> SEQ ID NO 56
<211> LENGTH: 7
<212> TYPE: PRT
<213> ORGANISM: Mus musculus

<400> SEQUENCE: 56

Ser Ala Ser Tyr Arg Tyr Ser
1               5

<210> SEQ ID NO 57
<211> LENGTH: 9
<212> TYPE: PRT
<213> ORGANISM: Mus musculus

<400> SEQUENCE: 57

Gln Gln Tyr Lys Thr Tyr Pro Tyr Thr
1               5
```